United States Patent
Manoharan et al.

(10) Patent No.: US 10,131,908 B2
(45) Date of Patent: *Nov. 20, 2018

(54) 5' PHOSPHATE MIMICS

(71) Applicant: Alnylam Pharmaceuticals, Inc., Cambridge, MA (US)

(72) Inventors: Muthiah Manoharan, Cambridge, MA (US); Kallanthottathil G. Rajeev, Cambridge, MA (US); Marija Prhavc, Cambridge, MA (US); Ivan Zlatev, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 14/551,714

(22) Filed: Nov. 24, 2014

(65) Prior Publication Data

US 2015/0080457 A1    Mar. 19, 2015

Related U.S. Application Data

(63) Continuation of application No. 13/382,346, filed as application No. PCT/US2010/041209 on Jul. 7, 2010, now Pat. No. 8,927,513.

(60) Provisional application No. 61/223,674, filed on Jul. 7, 2009.

(51) Int. Cl.
| | |
|---|---|
| C12N 15/115 | (2010.01) |
| C07H 19/11 | (2006.01) |
| C12N 15/113 | (2010.01) |
| C07H 19/213 | (2006.01) |
| C07H 19/10 | (2006.01) |
| C07H 19/20 | (2006.01) |

(52) U.S. Cl.
CPC .......... *C12N 15/113* (2013.01); *C07H 19/10* (2013.01); *C07H 19/11* (2013.01); *C07H 19/20* (2013.01); *C07H 19/213* (2013.01); *C12N 2310/11* (2013.01)

(58) Field of Classification Search
CPC combination set(s) only.
See application file for complete search history.

(56) References Cited

U.S. PATENT DOCUMENTS

| | | | |
|---|---|---|---|
| 5,874,552 A | 2/1999 | Jones et al. | |
| 6,271,370 B1 * | 8/2001 | Scott ............... | C07H 19/04 |
| | | | 536/124 |
| 2003/0143732 A1 | 7/2003 | Fosnaugh et al. | |
| 2005/0266422 A1 | 12/2005 | Vagle et al. | |

FOREIGN PATENT DOCUMENTS

| | | |
|---|---|---|
| WO | 1996040705 A1 | 12/1996 |
| WO | 2003073989 A2 | 9/2003 |

OTHER PUBLICATIONS

Bookser et al., "High-Throughput Synthesis of HepDirect Prodrugs of Necleoside Monophosphates," J. Comb. Chem. 10(4):567-572 (2008).

* cited by examiner

*Primary Examiner* — Jennifer Pitrak McDonald
(74) *Attorney, Agent, or Firm* — Jeffrey N. Townes; Cozen O'Connor

(57) ABSTRACT

The present invention provides nucleosides and oligonucleotides comprising a 5' phosphate mimics of formula (IVc) or (Vc),

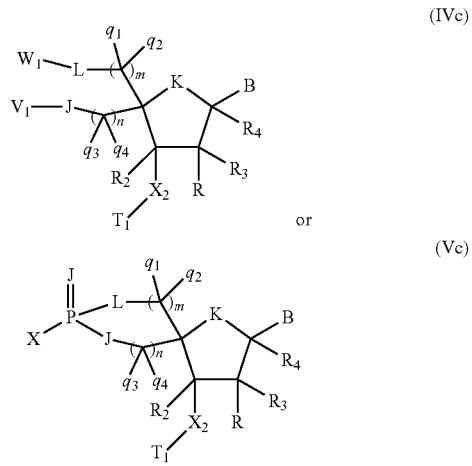

One aspect of the present invention relates to modified nucleosides and oligonucleotides comprising such dinucleotide of formula (Ia). Another aspect of the invention relates to a method of inhibiting the expression of a gene in call, the method comprising (a) contacting an oligonucleotide of the invention with the cell; and (b) maintaining the cell from step (a) for a time sufficient to obtain degradation of the mRNA of the target gene.

17 Claims, No Drawings

5' PHOSPHATE MIMICS

PRIORITY

This application is a continuation of U.S. patent application Ser. No. 13/382,346, filed Mar. 6, 2012, which claims priority to PCT Application No. PCT/US2010/041209, filed Jul. 7, 2010, which claims benefit of priority to U.S. Provisional Application No. 61/223,674, filed Jul. 7, 2009, all of which are herein incorporated by reference in their entirety.

TECHNICAL FIELD

Provided herein are modified nucleosides and oligonucleotides prepared therefrom. More particularly, the invention provides oligonucleotides comprising a 5' phosphate mimic.

BACKGROUND

Oligonucleotides and their analogs have been developed for various uses in molecular biology, including use as probes, primers, linkers, adapters, and gene fragments. In a number of these applications, the oligonucleotides specifically hybridize to a target nucleic acid sequence. Hybridization is the sequence specific hydrogen bonding of oligonucleotides via Watson-Crick and/or Hoogsteen base pairs to RNA or DNA. The bases of such base pairs are said to be complementary to one another.

Double-stranded RNA molecules (dsRNA) can block gene expression by virtue of a highly conserved regulatory mechanism known as RNA interference (RNAi). Briefly, the RNA III Dicer enzyme processes dsRNA into small interfering RNA (also sometimes called short interfering RNA or siRNA) of approximately 22 nucleotides. One strand of the siRNA (the "antisense strand") then serves as a guide sequence to induce cleavage of messenger RNAs (mRNAs) including a nucleotide sequence which is at least partially complementary to the sequence of the antisense strand by an RNA-induced silencing complex, RISC. The antisense strand is not cleaved or otherwise degraded in this process, and the RISC including the antisense strand can subsequently affect the cleavage of further mRNAs.

It is desirable that oligonucleotides be able to be synthesized to have customized properties that are tailored for desired uses. Thus a number of chemical modifications have been introduced into oligonucleotides to increase their usefulness in diagnostics, as research reagents and as therapeutic entities. Such modifications include those designed to increase binding to a target strand (i.e., increase their melting temperatures, $T_m$), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Even given the advances that have already been made in the art, there remains an ongoing need for new modifications designed to, for example, increase binding to a target strand (i.e., increase their melting temperatures, $T_m$), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

SUMMARY

In one aspect the invention provides nucleosides comprising phosphate and phosphate mimics at the 5'-position and oligonucleotides prepared therefrom. The said modified oligonucleotides can be single stranded siRNA (ss siRNA), double stranded siRNA (ds siRNA), micro RNA, antimicroRNA, supermir, aptamer antisense oligonucleotide, decoy oligonucleotide, ribozymes, immunostimulatory oligonucleotide, RNAa activator or U1 adaptor, containing a motif selected from the modifications described herein and combinations of modifications thereof. The modified oligonucleotide may be one of the strands or constitute both strands of a double stranded oligonucleotide such as ds siRNA. In one occurrence the modified oligonucleotide is the guide or antisense strand and in another occurrence the modified oligonucleotide is sense or passenger strand of the double stranded siRNA or in another occurrence both the strands of ds siRNA bear modified oligonucleotides.

Another aspect of the invention relates to a method of inhibiting the expression of a gene in a cell, the method comprising (a) contacting an oligonucleotide of the invention with the cell; and (b) maintaining the cell from step (a) for a time sufficient to obtain degradation of the mRNA of the target gene.

DETAILED DESCRIPTION

In one embodiment, the invention provides a nucleoside of formula (I), or isomers thereof:

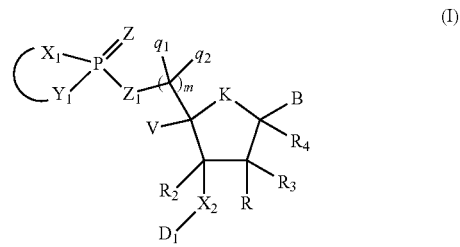

(I)

wherein $D_1$ is H, a hydroxyl protecting group, a solid support, or a reactive phosphorus group;

K is O, S, NR' or optionally substituted alkyl;

B is selected from the group consisting of hydrogen, aliphatic, substituted aliphatic, natural nucleobase, modified nucleobase and universal nucleobase;

V is independently selected from the group consisting of hydrogen, straight- or branched-, optionally substituted alkyl, optionally substituted alkenyl, optionally substituted alkynyl, which one or more methylenes can be interrupted by O, S, S(O), $SO_2$, N(R'), C(O), phosphorus containing linkage, aryl, heteroaryl, heterocyclic, or cycloalkyl; R' is hydrogen, acyl, aliphatic or substituted aliphatic;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$X_2$ is O, NH, or S;

Z is O, S or NR';

$X_1$, $Y_1$ and $Z_1$ are each independently O, S, NR' or alkylene;

q1 and q2 are each independently selected from H, OH, SH, halogen, and aliphatic;

$R_2$, $R_3$, and $R_4$ are each independently selected from H, halogen, OH, C1-C6 alkyl, C1-C6 haloalkyl; alternatively, two of R, $R_2$, $R_3$, $R_4$ and V can be taken together to form a 5-8 membered ring, wherein the ring can be substituted or unsubstituted and can optionally contain a heteroatom; and

is an optionally substituted C2-C8 alkyl. In certain embodiments, K is O or S.

In one embodiment, the invention provides oligonucleotides comprising a nucleoside of formula (Ia), or isomers thereof:

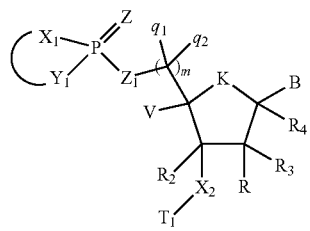

(Ia)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is O, S, NR' or optionally substituted alkyl;

B is selected from the group consisting of hydrogen, aliphatic, substituted aliphatic, natural nucleobase, modified nucleobase and universal nucleobase;

V is independently selected from the group consisting of hydrogen, straight- or branched-, optionally substituted alkyl, optionally substituted alkenyl, optionally substituted alkynyl, which one or more methylenes can be interrupted by O, S, S(O), $SO_2$, N(R'), C(O), phosphorus containing linkage, aryl, heteroaryl, heterocyclic, or cycloalkyl; R' is hydrogen, acyl, aliphatic or substituted aliphatic;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$X_2$ is O, NH, or S;

Z is O, S or NR';

$X_1$, $Y_1$ and $Z_1$ are each independently O, S, NR' or alkylene;

q1 and q2 are each independently selected from H, OH, SH, halogen, and aliphatic;

$R_2$, $R_3$, and $R_4$ are each independently selected from H, halogen, OH, C1-C6 alkyl, C1-C6 haloalkyl; alternatively, two of R, $R_2$, $R_3$, $R_4$ and V can be taken together to form a 5-8 membered ring, wherein the ring can be substituted or unsubstituted and can optionally contain a hetroatom; and

is an optionally substituted C2-C8 alkyl. In one example K is O or S.

In one embodiment, the invention provides a nucleoside of formula (II), or isomers thereof:

(II)

wherein $D_1$ is H, a hydroxyl protecting group, a solid support, or a reactive phosphorus group;

K is O, S, NR' or optionally substituted alkyl;

B is selected from the group consisting of hydrogen, aliphatic, substituted aliphatic, natural nucleobase, modified nucleobase and universal nucleobase;

V is selected from the group consisting of hydrogen, straight- or branched-, optionally substituted alkyl, optionally substituted alkenyl, optionally substituted alkynyl, which one or more methylenes can be interrupted by O, S, S(O), $SO_2$, N(R'), C(O), phosphorous containing linkage, aryl, heteroaryl, heterocyclic, or cycloalkyl; R' is hydrogen, acyl, aliphatic or substituted aliphatic;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$L_{10}$ is absent or selected from the group consisting of S, O, NR', alkylene, alkenylene, and alkynylene;

$W_1$ is independently $OR_{10}$, $OCO_2R_{10}$, $NR_{20}R_{30}$, $OCON R_{20}R_{30}$, $OSO_2R_{10}$, and optionally substituted heterocyclic, a boronic group ($B(OH)_2$), or

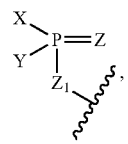

wherein $R_{20}$ and $R_{30}$ are each independently hydrogen, acyl, aliphatic or substituted aliphatic, aryl, heteroaryl, heterocyclic or $R_{20}$ and $R_{30}$ taken together to form a heterocyclic ring; $R_{10}$ is hydrogen, aliphatic, substituted aliphatic, aryl, heteroaryl, heterocyclic;

Z is O, S or NR';

$Z_1$ is O or S;

X and Y are each independently selected from the group consisting of H, OH, SH, SM, OM, borane ($BH_3$), optionally substituted alkyl, optionally substituted alkoxy, optionally substituted alkylthio, optionally substituted alkylamino, optionally substituted dialkylamino, or X and Y taken together with the atoms they are attached to form

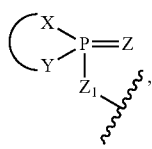

where

is an optionally substituted C2-C8 alkyl and M is a metal counter ion such as an alkali metal or a transition metal with an overall charge of +1; and provided that when V is hydrogen, $W_1$ is not OH,

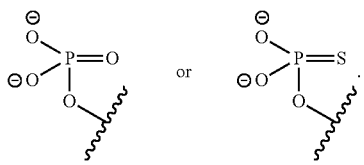 [SMILES: *OP(=O)([O-])[O-] ; *OP([O-])([O-])=S]

In certain embodiments, K is O or S.

In one embodiment, the invention provides oligonucleotides comprising a nucleoside of formula (IIa), and isomers thereof:

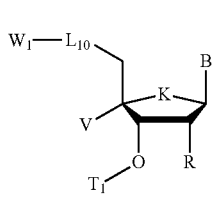

(IIa)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is independently for each occurrence O, S, NR' or optionally substituted alkyl; each B is selected independently from the group consisting of hydrogen, aliphatic, substituted aliphatic, natural nucleobase, modified nucleobase and universal nucleobase;

V is selected from the group consisting of hydrogen, straight- or branched-, optionally substituted alkyl, optionally substituted alkenyl, optionally substituted alkynyl, which one or more methylenes can be interrupted by O, S, S(O), $SO_2$, N(R'), C(O), phosphorous containing linkage, aryl, heteroaryl, heterocyclic, or cycloalkyl; R' is hydrogen, acyl, aliphatic or substituted aliphatic;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$L_{10}$ is absent or selected from the group consisting of S, O, NR', optionally substituted alkylene, optionally substituted alkenylene, and optionally substituted alkynylene;

$W_1$ is independently selected from the group consisting of $OR_{10}$, $OCO_2R_{10}$, $NR_{20}R_{30}$, $OCON\ R_{20}R_{30}$, $OSO_2R_{10}$, and optionally substituted heterocyclic, boronic group ($B(OH)_2$), and

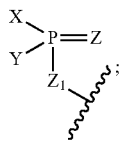

$R_{20}$ and $R_{30}$ are each independently hydrogen, acyl, aliphatic or substituted aliphatic, aryl, heteroaryl, heterocyclic or $R_{20}$ and $R_{30}$ taken together form a heterocyclic ring; $R_{10}$ is hydrogen, aliphatic, substituted aliphatic, aryl, heteroaryl, or heterocyclic;

Z is O, S or NR';

$Z_1$ is O or S;

X and Y are each independently selected from the group consisting of H, OH, SH, SM, OM, borane ($BH_3$), optionally substituted alkyl, optionally substituted alkoxy, optionally substituted alkylthio, optionally substituted alkylamino, optionally substituted dialkylamino, or X and Y taken together with the atoms they are attached to form

wherein

is an optionally substituted C2-C8 alkyl and M is a metal counter ion such as an alkali metal or a transition metal with an overall charge of +1, and provided that when V is hydrogen, $W_1$ is not OH,

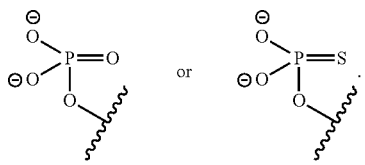 [SMILES: *OP(=O)([O-])[O-] ; *OP([O-])([O-])=S]

In one embodiment K is O or S.

In one embodiment, the invention provides a nucleoside of formula (III), or isomers thereof:

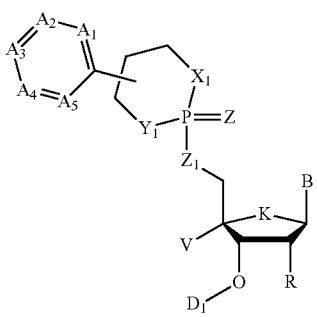

(III)

wherein $D_1$ is H, a hydroxyl protecting group, a solid support, or a reactive phosphorus group;

K is O, S, NR' or optionally substituted alkyl;

B is selected from the group consisting of hydrogen, aliphatic, substituted aliphatic, natural nucleobase, modified nucleobase and universal nucleobase;

V is selected from hydrogen, straight- or branched-, optionally substituted alkyl, optionally substituted alkenyl, optionally substituted alkynyl, which one or more methylenes can be interrupted by O, S, S(O), SO$_2$, N(R'), C(O), phosphorous containing linkage, aryl, heteroaryl, heterocyclic, or cycloalkyl;

R' is hydrogen, acyl, aliphatic or substituted aliphatic;

Z is O, S or NR'; $X_1$, $Y_1$ and $Z_1$ are each independently O, S, NR' or alkylene;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino; and $A_1$-$A_5$ are each independently $CR_{21}$ or N; $R_{21}$ is independently in each occurrence selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, optionally substituted alkoxy, optionally substituted alkylamino, optionally substituted dialkylamino, optionally substituted alkylthio, optionally substituted alkylsulfonyl, CF$_3$, NO$_2$, CN, N$_3$, substituted carbonyl, sulfonyl, acyl, aryl, substituted aryl, heteroaryl, substituted heteroaryl, heterocyclic, substituted heterocyclic, cycloalkyl, or substituted cycloalkyl.

In one embodiment, the invention provides oligonucleotides comprising a nucleoside of formula (IIIa), and isomers thereof:

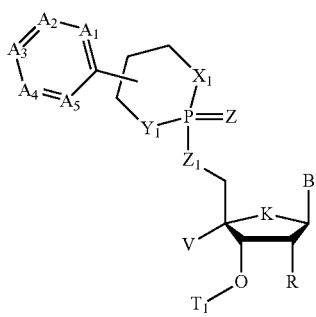

(IIIa)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is independently for each occurrence O, S, NR' or optionally substituted alkyl;

each B is selected independently from the group consisting of hydrogen, aliphatic, substituted aliphatic, natural nucleobase, modified nucleobase and universal nucleobase;

V is selected from the group consisting of hydrogen, straight- or branched-, optionally substituted alkyl, optionally substituted alkenyl, optionally substituted alkynyl, which one or more methylenes can be interrupted by O, S, S(O), SO$_2$, N(R'), C(O), phosphorus containing linkage, aryl, heteroaryl, heterocyclic, or cycloalkyl; R' is hydrogen, acyl, aliphatic or substituted aliphatic;

X is H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

Z is O, S or NR'; $X_1$, $Y_1$ and $Z_1$ are each independently O, S, NR' or alkylene;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino; and $A_1$-$A_5$ are each independently $CR_{21}$ or N; $R_{21}$ is independently in each occurrence selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, optionally substituted alkoxy, optionally substituted alkylamino, optionally substituted dialkylamino, optionally substituted alkylthio, optionally substituted alkylsulfonyl, CF$_3$, NO$_2$, CN, N$_3$, substituted carbonyl, sulfonyl, acyl, aryl, substituted aryl, heteroaryl, substituted heteroaryl, heterocyclic, substituted heterocyclic, cycloalkyl, or substituted cycloalkyl;

In one embodiment, the invention provides oligonucleotides comprising a dinucleotide of formula (IIIb), and isomers thereof:

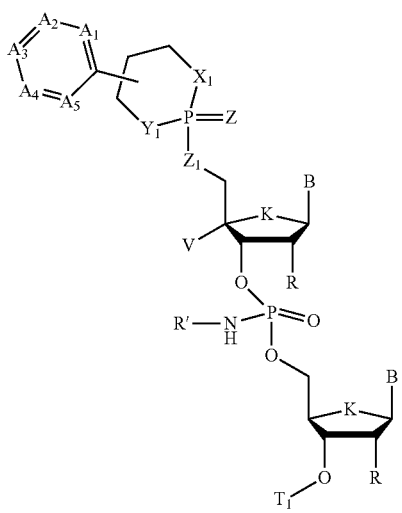

(IIIb)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is independently O, S, NR', optionally substituted alkyl in each occurrence;

B is independently selected from hydrogen, aliphatic, substituted aliphatic, natural nucleobase, modified nucleobase and universal nucleobase;

V is selected from hydrogen, straight- or branched-, substituted or unsubstituted alkyl, substituted or unsubstituted alkenyl, substituted or unsubstituted alkynyl, which one or more methylenes can be interrupted by O, S, S(O), $SO_2$, N(R'), C(O), phosphorous containing linkage, aryl, heteroaryl, heterocyclic, or cycloalkyl, where R' is hydrogen, acyl, aliphatic or substituted aliphatic;

$X_1$, $Y_1$ and $Z_1$ are each independently O, S, NR' or alkylene;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino; and $A_1$-$A_5$ are independently $CR_{21}$ or N; $R_{21}$ is independently in each occurrence selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl.

In one embodiment, the invention provides a nucleoside of formula (IV), or isomers thereof:

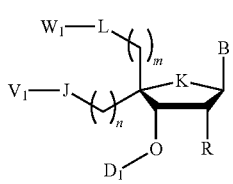
(IV)

wherein $D_1$ is H, a hydroxyl protecting group, a solid support, or a reactive phosphorus group;

K is O, S, NR' or optionally substituted alkyl; B is selected from the group consisting of hydrogen, aliphatic, substituted aliphatic, natural nucleobase, modified nucleobase and universal nucleobase;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

L and J are each independently absent or independently selected from the group consisting of S, O, NR', optionally substituted alkylene, optionally substituted alkenylene, and optionally substituted alkynylene;

$W_1$ and $V_1$ are each independently selected from the group consisting of $OR_{10}$, $OCO_2R_{10}$, $NR_{20}R_{30}$, $OCONR_{20}R_{30}$, $OSO_2R_{10}$, optionally substituted heterocyclic, boronic group $(B(OH)_2)$ and

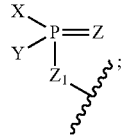

$R_{20}$ and $R_{30}$ are each independently hydrogen, acyl, aliphatic or substituted aliphatic, aryl, heteroaryl, heterocyclic, or $R_{20}$ and $R_{30}$ taken together form a heterocyclic ring; $R_{10}$ is hydrogen, aliphatic, substituted aliphatic, aryl, heteroaryl, or heterocyclic;

Z is O, S or NR';

$Z_1$ is O or S;

X and Y are each independently selected from the group consisting of H, OH, SH, SM, OM, borane ($BH_3$), optionally substituted alkyl, optionally substituted alkoxy, optionally substituted alkylthio, optionally substituted alkylamino, optionally substituted dialkylamino, or X and Y taken together with the atoms they are attached to form

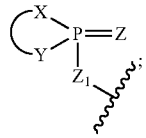

wherein

is an optionally substituted C2-C8 alkyl and M is a metal counter ion such as an alkali metal or a transition metal with an overall charge of +1; and m and n are independently 0-10.

In one embodiment, the invention provides oligonucleotides comprising a nucleoside of formula (IVa),

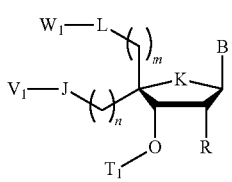
(IVa)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is independently for each occurrence O, S, NR' or optionally substituted alkyl;

each B is independently selected from the group consisting of hydrogen, aliphatic, substituted aliphatic, natural nucleobase, modified nucleobase and universal nucleobase;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

L and J are each independently absent or independently selected from the group consisting of S, O, NR', optionally substituted alkylene, optionally substituted alkenylene, and optionally substituted alkynylene;

$W_1$ and $V_1$ are independently selected from the group consisting of $OR_{10}$, $OCO_2R_{10}$, $NR_{20}R_{30}$, $OCON\ R_{20}R_{30}$, $OSO_2R_{10}$, optionally substituted heterocyclic, a boronic group $(B(OH)_2)$ and

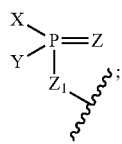

$R_{20}$ and $R_{30}$ are independently hydrogen, acyl, aliphatic or substituted aliphatic, aryl, heteroaryl, heterocyclic, or $R^{20}$ and $R^{30}$ taken together form a heterocyclic ring; $R_{10}$ is hydrogen, aliphatic, substituted aliphatic, aryl, heteroaryl, or heterocyclic;

Z is O, S or NR';

$Z_1$ is O or S;

X and Y are each independently selected from the group consisting of H, OH, SH, SM, OM, borane ($BH_3$), optionally substituted alkyl, optionally substituted alkoxy, optionally substituted alkylamino, optionally substituted dialkylamino, or X and Y taken together with the atoms they are attached to form

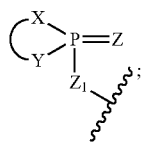

wherein ( is an optionally substituted C2-C8 alkyl and M is a metal counter ion such as an alkali metal or a transition metal with an overall charge of +1; and m and n are independently 0-10. In one embodiment, the invention provides a nucleoside of formula (IVb), or isomers thereof:

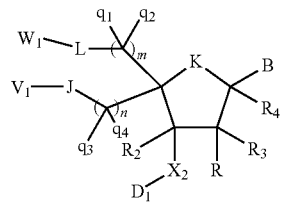

(IVb)

wherein $D_1$ is H, a hydroxyl protecting group, a solid support, or a reactive phosphorus group;

K is O, S, NR' or optionally substituted alkyl;

B is selected from the group consisting of hydrogen, aliphatic, substituted aliphatic, natural nucleobase, modified nucleobase and universal nucleobase;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$X_2$ is O, NH, or S;

Z is O, S or NR';

$X_1$, $Y_1$ and $Z_1$ are each independently O, S, NR' or alkylene, where R' is hydrogen, acyl, aliphatic or substituted aliphatic;

q1, q2, q3 and q4 are each independently H, OH, SH, halogen, and aliphatic;

$R_2$, $R_3$, $R_4$ and are each independently selected from H, halogen, OH, C1-C6 alkyl, C1-C6 haloalkyl; alternatively, two of R, $R_2$, $R_3$, $R_4$, $W_1$ and $V_1$ can be taken together to form a 5-8 membered ring, wherein the ring can be substituted or unsubstituted and can optionally contain a hetroatom;

L and J are each independently absent or independently selected from the group consisting of S, O, NR', optionally substituted alkylene, optionally substituted alkenylene, and optionally substituted alkynylene;

$W_1$ and $V_1$ are independently selected from the group consisting of $OR_{10}$, $OCO_2R_{10}$, $NR_{20}R_{30}$, $OCON\ R_{20}R_{30}$, $OSO_2R_{10}$, optionally substituted heterocyclic, a boronic group $(B(OH)_2)$ and

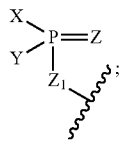

$R_{20}$ and $R_{30}$ are independently hydrogen, acyl, aliphatic or substituted aliphatic, aryl, heteroaryl, heterocyclic, or $R^{20}$ and $R^{30}$ taken together form a heterocyclic ring; $R_{10}$ is hydrogen, aliphatic, substituted aliphatic, aryl, heteroaryl, or heterocyclic;

Z is O, S or NR';

$Z_1$ is O or S;

X and Y are each independently selected from the group consisting of H, OH, SH, SM, OM, borane ($BH_3$), optionally substituted alkyl, optionally substituted alkoxy, optionally substituted alkylamino, optionally substituted dialkylamino, or X and Y taken together with the atoms they are attached to form

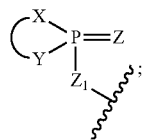

wherein

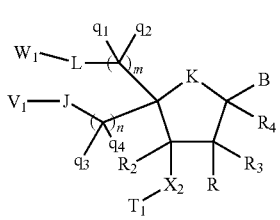

is an optionally substituted C2-C8 alkyl and M is a metal counter ion such as an alkali metal or a transition metal with an overall charge of +1; and m and n are independently 0-10.

In one embodiment, the invention provides oligonucleotides comprising a nucleoside of formula (IVc), or isomers thereof:

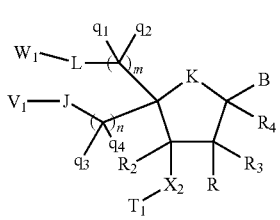
(IVc)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is O, S, NR' or optionally substituted alkyl;

B is selected from the group consisting of hydrogen, aliphatic, substituted aliphatic, natural nucleobase, modified nucleobase and universal nucleobase;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$X_2$ is O, NH, or S;

Z is O, S or NR';

$X_1$, $Y_1$ and $Z_1$ are each independently O, S, NR' or alkylene, where R' is hydrogen, acyl, aliphatic or substituted aliphatic;

q1, q2, q3 and q4 are each independently H, OH, SH, halogen, and aliphatic;

$R_2$, $R_3$, and $R_4$ are each independently selected from H, halogen, OH, C1-C6 alkyl, C1-C6 haloalkyl; alternatively, two of R, $R_2$, $R_3$, $R_4$, $W_1$ and $V_1$ can be taken together to form a 5-8 membered ring, wherein the ring can be substituted or unsubstituted and can optionally contain a hetroatom;

L and J are each independently absent or independently selected from the group consisting of S, O, NR', optionally substituted alkylene, optionally substituted alkenylene, and optionally substituted alkynylene;

$W_1$ and $V_1$ are independently selected from the group consisting of $OR_{10}$, $OCO_2R_{10}$, $NR_{20}R_{30}$, $OCON R_{20}R_{30}$, $OSO_2R_{10}$, optionally substituted heterocyclic, a boronic group $(B(OH)_2)$ and

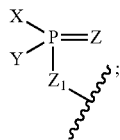

$R_{20}$ and $R_{30}$ are independently hydrogen, acyl, aliphatic or substituted aliphatic, aryl, heteroaryl, heterocyclic, or $R^{20}$ and $R^{30}$ taken together form a heterocyclic ring; $R_{10}$ is hydrogen, aliphatic, substituted aliphatic, aryl, heteroaryl, or heterocyclic;

Z is O, S or NR';

$Z_1$ is O or S;

X and Y are each independently selected from the group consisting of H, OH, SH, SM, OM, borane ($BH_3$), optionally substituted alkyl, optionally substituted alkoxy, optionally substituted alkylamino, optionally substituted dialkylamino, or X and Y taken together with the atoms they are attached to form

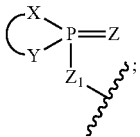

wherein

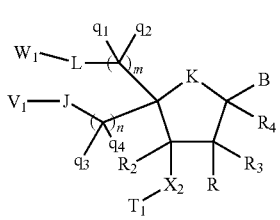

is an optionally substituted C2-C8 alkyl and M is a metal counter ion such as an alkali metal or a transition metal with an overall charge of +1; and m and n are independently 0-10.

In one embodiment, V and W can be taken with the atoms they attached to in formula (IV) to form a nucleoside of formula (V), or isomers thereof:

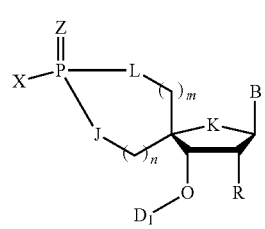
(V)

wherein $D_1$ is H, a hydroxyl protecting group, a solid support, or a reactive phosphorus group;

K is O, S, NR' or optionally substituted alkyl; B is selected from the group consisting of hydrogen, aliphatic, substituted aliphatic, natural nucleobase, modified nucleobase and universal nucleobase;

X is H, OH, OM, SH, SM, optionally substituted alkyl, optionally substituted alkoxy, optionally substituted alkylthio, optionally substituted alkylamino, optionally substituted dialkylamino, where M is a metal counter ion such as an alkali metal or a transition metal with an overall charge of +1;

Z is O, S or NR';

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino, R' is hydrogen, acyl, aliphatic or substituted aliphatic;

L and J are each independently absent or independently selected from the group consisting of S, O, NR', alkylene, alkenylene, and alkynylene; and m and n are independently 0-10. In one embodiment, V and W are taken together with the atom they attached in formula (IVa) to form a cyclic moiety represented by formula (Va):

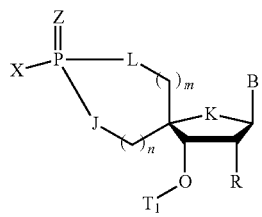

(Va)

wherein $T_1$ and R are each, independently, hydroxyl, a protected hydroxyl, a linked conjugate group or an internucleoside linking group attaching the nucleoside to the oligonucleotide wherein at least one of $T_1$ and R is au internucleoside linking group attaching the nucleoside to the oligonucleotide;

K is independently for each occurrence O, S, NR' or optionally substituted alkyl;

each B is independently selected from the group consisting of hydrogen, aliphatic, substituted aliphatic, natural nucleobase, modified nucleobase and universal nucleobase;

X is H, OH, OM, SH, SM, optionally substituted alkyl, optionally substituted alkoxy, optionally substituted alkylthio, optionally substituted alkylamino, optionally substituted dialkylamino, where M is a metal counter ion such as an alkali metal or a transition metal with an overall charge of +1;

Z is O, S or NR';

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino, R' is hydrogen, acyl, aliphatic or substituted aliphatic;

L and J are each independently absent or independently selected from the group consisting of S, O, NR', alkylene, alkenylene, and alkynylene; and m and n are independently 0-10.

In one embodiment, the invention provides a nucleoside of formula (IVb), or isomers thereof:

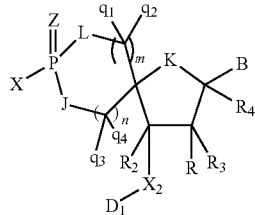

(Vb)

wherein $D_1$ is H, a hydroxyl protecting group, a solid support, or a reactive phosphorus group;

K is O, S, NR' or optionally substituted alkyl;

B is selected from the group consisting of hydrogen, aliphatic, substituted aliphatic, natural nucleobase, modified nucleobase and universal nucleobase;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$X_2$ is O, NH, or S;

Z is O, S or NR';

q1, q2, q3 and q4 are each independently H, OH, SH, halogen, and aliphatic;

$R_2$, $R_3$, and $R_4$ are each independently selected from H, halogen, OH, C1-C6 alkyl, C1-C6 haloalkyl; alternatively, two of R, $R_2$, $R_3$ and $R_4$ can be taken together to form a 5-8 membered ring, wherein the ring can be substituted or unsubstituted and can optionally contain a hetroatom;

L and J are each independently absent or independently selected from the group consisting of S, O, NR', optionally substituted alkylene, optionally substituted alkenylene, and optionally substituted alkynylene;

X is each independently selected from the group consisting of H, OH, SH, SM, OM, borane ($BH_3$), optionally substituted alkyl, optionally substituted alkoxy, optionally substituted alkylamino, optionally substituted dialkylamino, wherein M is a metal counter ion such as an alkali metal or a transition metal with an overall charge of +1; and m and n are independently 0-10.

In one embodiment, the invention provides a nucleoside of formula (IVc), or isomers thereof:

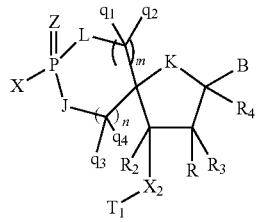

(Vc)

wherein $T_1$ and R are each, independently, hydroxyl, a protected hydroxyl, a linked conjugate group or an internucleoside linking group attaching the nucleoside to the oligonucleotide wherein at least one of $T_1$ and R is an internucleoside linking group attaching the nucleoside to the oligonucleotide;

K is O, S, NR' or optionally substituted alkyl;

B is selected from the group consisting of hydrogen, aliphatic, substituted aliphatic, natural nucleobase, modified nucleobase and universal nucleobase;

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

$X_2$ is O, NH, or S;

Z is O, S or NR';

q1, q2, q3 and q4 are each independently H, OH, SH, halogen, and aliphatic;

$R_2$, $R_3$, and $R_4$ are each independently selected from H, halogen, OH, C1-C6 alkyl, C1-C6 haloalkyl; alternatively, two of R, $R_2$, $R_3$ and $R_4$ can be taken together to form a 5-8 membered ring, wherein the ring can be substituted or unsubstituted and can optionally contain a hetroatom;

L and J are each independently absent or independently selected from the group consisting of S, O, NR', optionally substituted alkylene, optionally substituted alkenylene, and optionally substituted alkynylene;

X is each independently selected from the group consisting of H, OH, SH, SM, OM, borane ($BH_3$), optionally substituted alkyl, optionally substituted alkoxy, optionally substituted alkylamino, optionally substituted dialkylamino, wherein M is a metal counter ion such as an alkali metal or a transition metal with an overall charge of +1; and m and n are independently 0-10.

In one embodiment, the nucleosides provided herein are useful for modifying of oligonucleotides at one or more positions. Such modified oligonucleotides can be described as having a particular motif. In one embodiment, the motifs include without limitation, a gapped motif, a hemimer motif, a blockmer motif, a uniformly fully modified motif, a positionally modified motif and an alternating motif. In conjunction with these motifs a wide variety of internucleoside linkages can also be used including but not limited to phosphodiester and phosphorothioate internucleoside linkages which can be incorporated uniformly or in combinations. In one embodiment, altering the base sequence provides the targeting component for the oligonucleotides provided herein.

In one embodiment, $D_1$ is a reactive phosphorus group comprising a diisopropylcyanoethoxy phosphoramidite group. In a preferred embodiment, $D_1$ comprises a diisopropylcyanoethoxy phosphoramidite group.

In one embodiment, B is uracil, 5-methyluracil, 5-methylcytosine, 5-thiazolo-uracil, 5-thiazolo-cytosine, adenine, guanine, 2,6-diaminopurine, cytosine, 6-oxopurine, pseudouridine, $N^1$ substituted pseudouridine, xanthine, 2-aminopurine, or 7-deazapurine.

In one embodiment, each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) or 9-(p-methoxyphenyl)xanthine-9-yl (MOX). In a preferred embodiment, each of the hydroxyl protecting groups is, independently, acetyl, benzyl, t-butyldimethylsilyl, t-butyldiphenylsilyl or 4,4'-dimethoxytrityl.

Representative dinucleotides or further embodiments according to the invention are those selected from the Table A below or its geometric isomers, enantiomers, diastereomers, and racemates thereof:

TABLE A

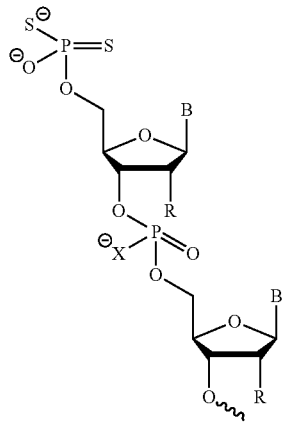

5'-Dithiophosphate

TABLE A-continued
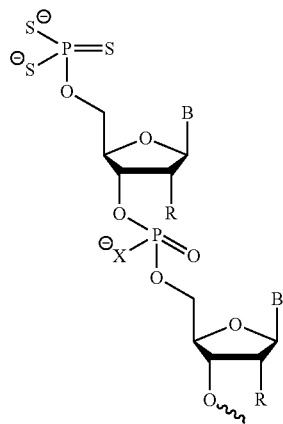
5'-Trithiophosphate
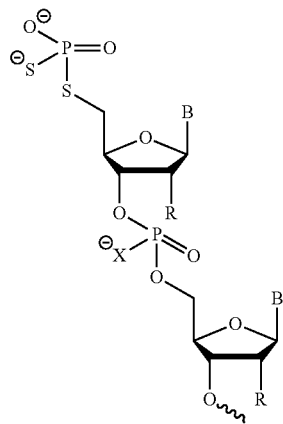
5'-C-Dithiophosphate
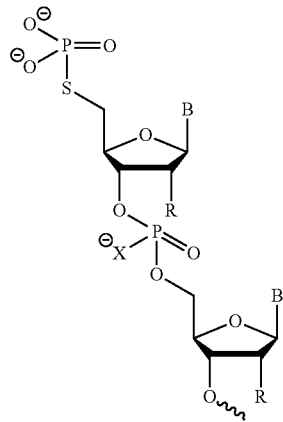
5'-C-Trithiophosphate TABLE A-continued
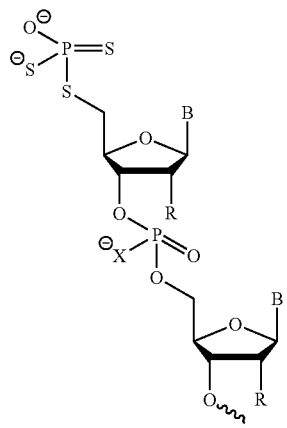
5'-C-Trithiophosphate
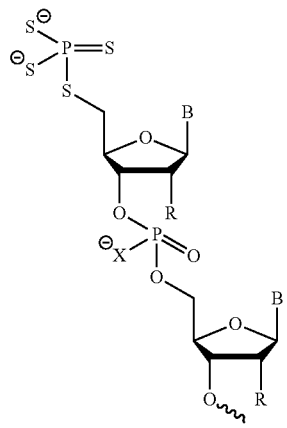
5'-C-Tetrathiophosphate
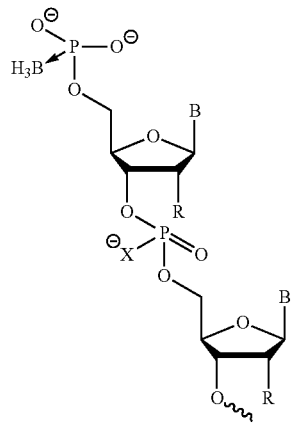
5'Boranophosphate TABLE A-continued
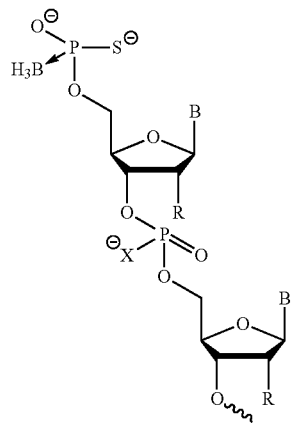
5'Borano-thiophosphate
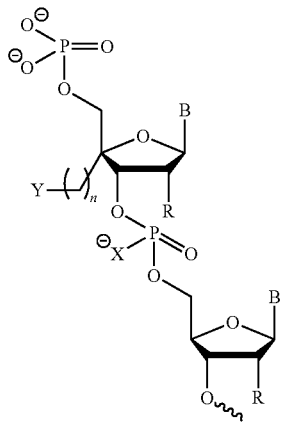
Y = R, OH, $NH_3^+$, OMe
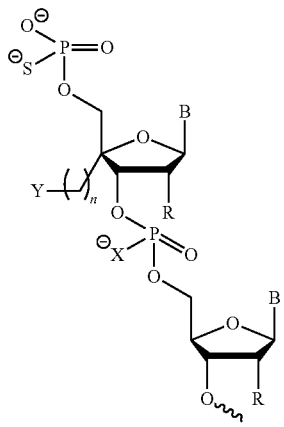
Y = R, OH, $NH_3^+$, OMe TABLE A-continued
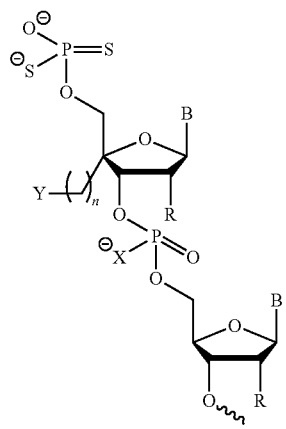
Y = R, OH, NH$_3^+$, OMe
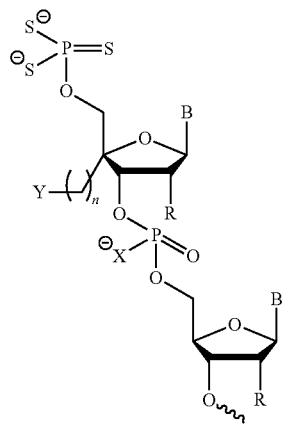
Y = R, OH, NH$_3^+$, OMe
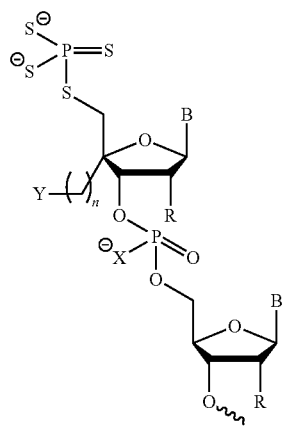
Y = R, OH, NH$_3^+$, OMe TABLE A-continued
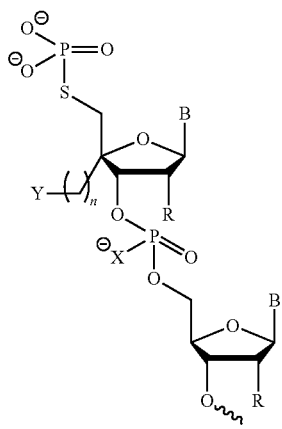
Y = R, OH, NH$_3^+$, OMe
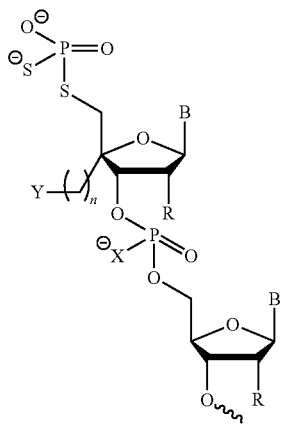
Y = R, OH, NH$_3^+$, OMe
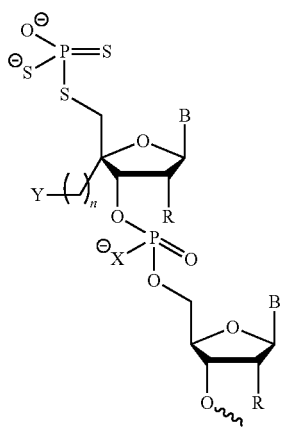
Y = R, OH, NH$_3^+$, OMe TABLE A-continued
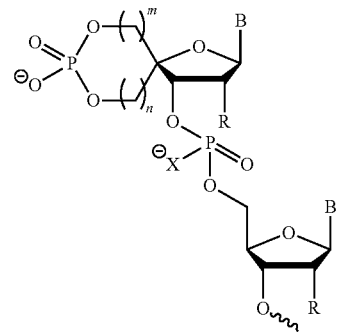
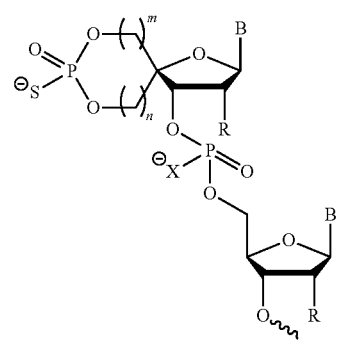
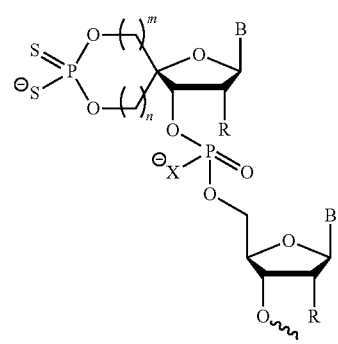
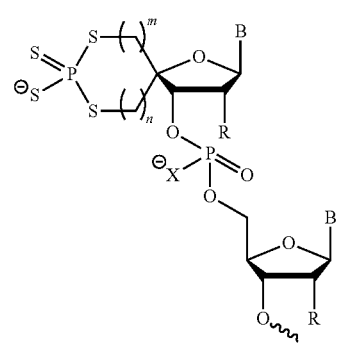

TABLE A-continued
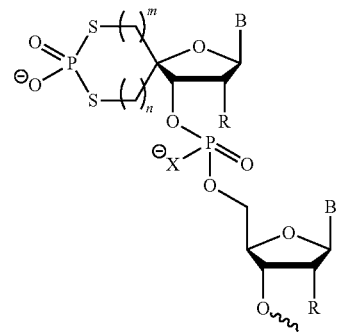
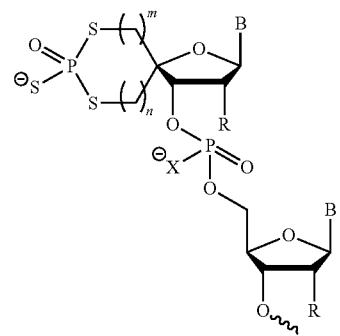
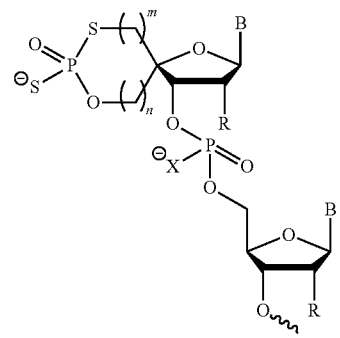
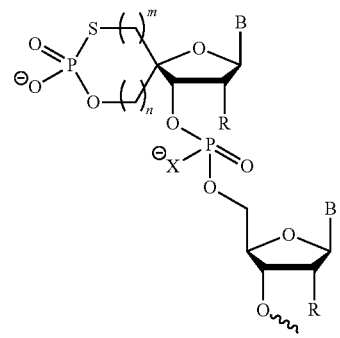

TABLE A-continued
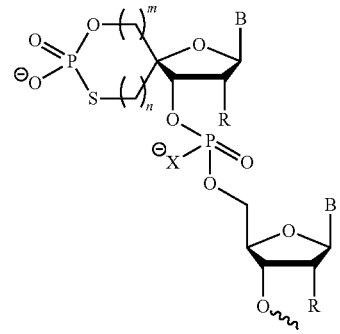
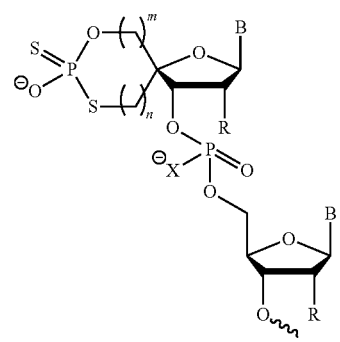
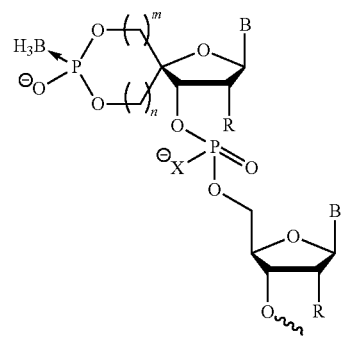
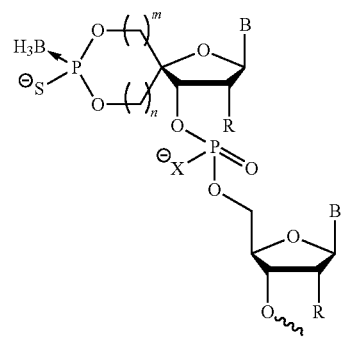

TABLE A-continued
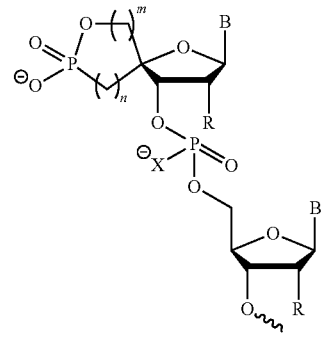
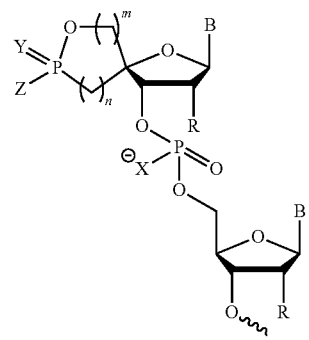
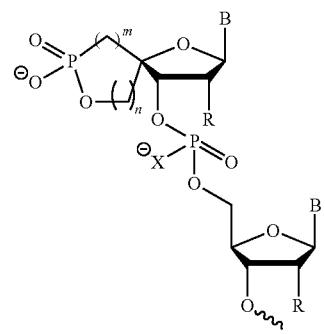
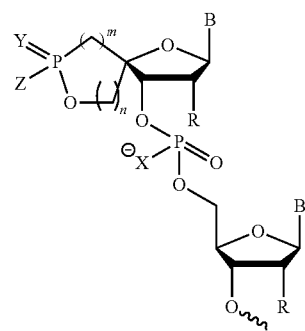

TABLE A-continued

[Structure diagram of nucleotide with branched phosphate groups, labeled with X, Y, Z, B, R, m, n]

X = O, Y = O and Z = O
X = O, Y = O and Z = S
X = O, Y = O and Z = BH$_3$
X = S, Y = O and Z = O
X = S, Y = O and Z = S
X = S, Y = O and Z = BH$_3$
X = O, Y = S and Z = O
X = O, Y = S and Z = S
X = O, Y = S and Z = BH$_3$
X = S, Y = S and Z = O
X = S, Y = S and Z = S
X = S, Y = S and Z = BH$_3$

[Structure diagram of nucleotide with branched phosphate groups, labeled with X, Y, Z, B, R, m, n]

X = O, Y = O and Z = O
X = O, Y = O and Z = S
X = O, Y = O and Z = BH$_3$
X = S, Y = O and Z = O
X = S, Y = O and Z = S
X = S, Y = O and Z = BH$_3$
X = O, Y = S and Z = O
X = O, Y = S and Z = S
X = O, Y = S and Z = BH$_3$
X = S, Y = S and Z = O
X = S, Y = S and Z = S
X = S, Y = S and Z = BH$_3$ TABLE A-continued

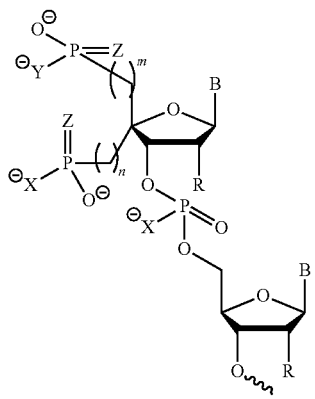

X = O, Y = O and Z = O
X = O, Y = O and Z = S
X = O, Y = O and Z = BH$_3$
X = S, Y = O and Z = O
X = S, Y = O and Z = S
X = S, Y = O and Z = BH$_3$
X = O, Y = S and Z = O
X = O, Y = S and Z = S
X = O, Y = S and Z = BH$_3$
X = S, Y = S and Z = O
X = S, Y = S and Z = S
X = S, Y = S and Z = BH$_3$

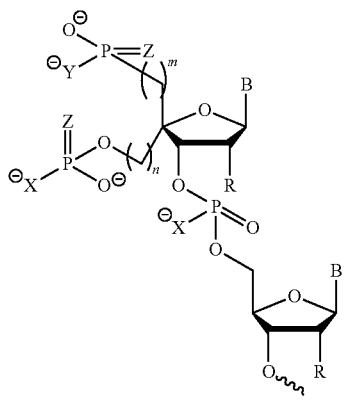

X = O, Y = O and Z = O
X = O, Y = O and Z = S
X = O, Y = O and Z = BH$_3$
X = S, Y = O and Z = O
X = S, Y = O and Z = S
X = S, Y = O and Z = BH$_3$
X = O, Y = S and Z = O
X = O, Y = S and Z = S
X = O, Y = S and Z = BH$_3$
X = S, Y = S and Z = O
X = S, Y = S and Z = S
X = S, Y = S and Z = BH$_3$

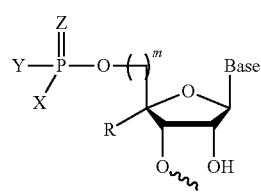

R = alkyl

TABLE A-continued

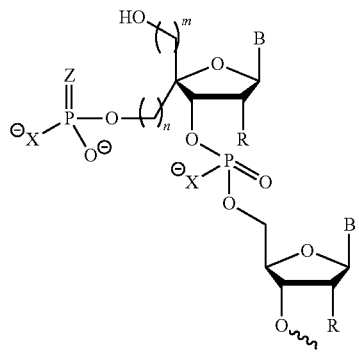

X = O, Y = O and Z = O
X = O, Y = O and Z = S
X = O, Y = O and Z = BH₃
X = S, Y = O and Z = O
X = S, Y = O and Z = S
X = S, Y = O and Z = BH₃
X = O, Y = S and Z = O
X = O, Y = S and Z = S
X = O, Y = S and Z = BH₃
X = S, Y = S and Z = O
X = S, Y = S and Z = S
X = S, Y = S and Z = BH₃

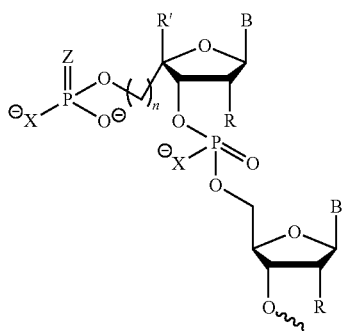

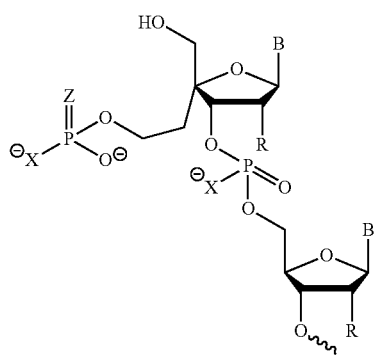

X = O, Y = O and Z = O
X = O, Y = O and Z = S
X = O, Y = O and Z = BH₃
X = S, Y = O and Z = O
X = S, Y = O and Z = S
X = S, Y = O and Z = BH₃
X = O, Y = S and Z = O
X = O, Y = S and Z = S
X = O, Y = S and Z = BH₃
X = S, Y = S and Z = O
X = S, Y = S and Z = S
X = S, Y = S and Z = BH₃

TABLE A-continued
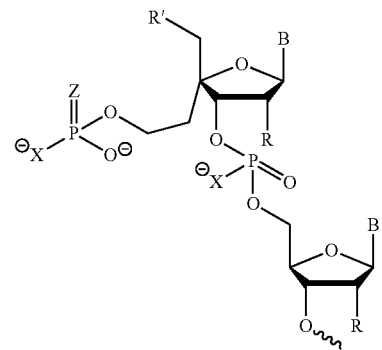
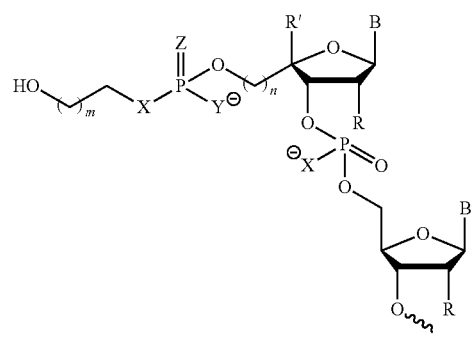
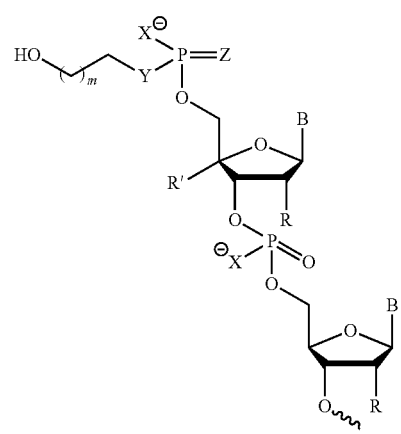
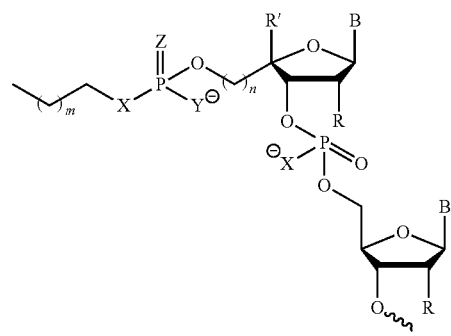

TABLE A-continued
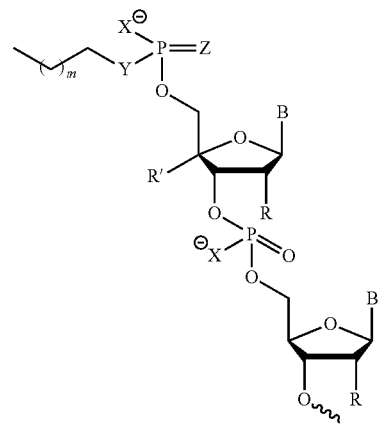
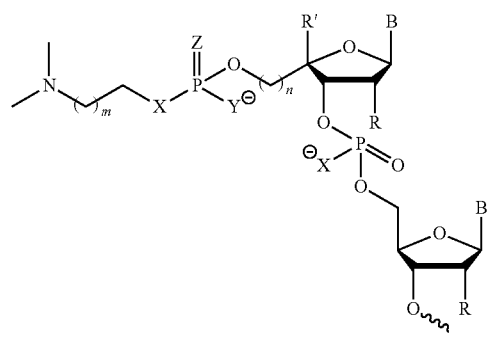
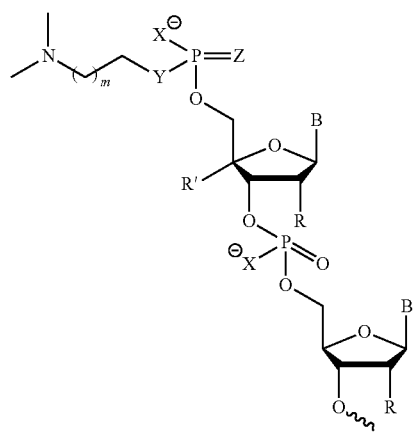
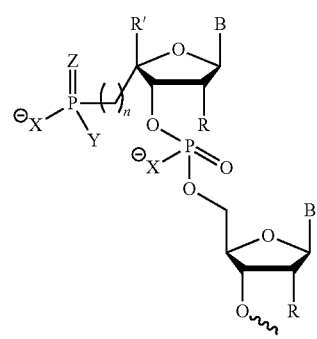

TABLE A-continued
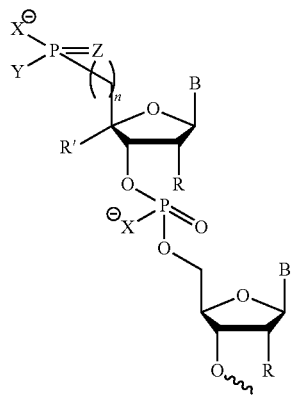
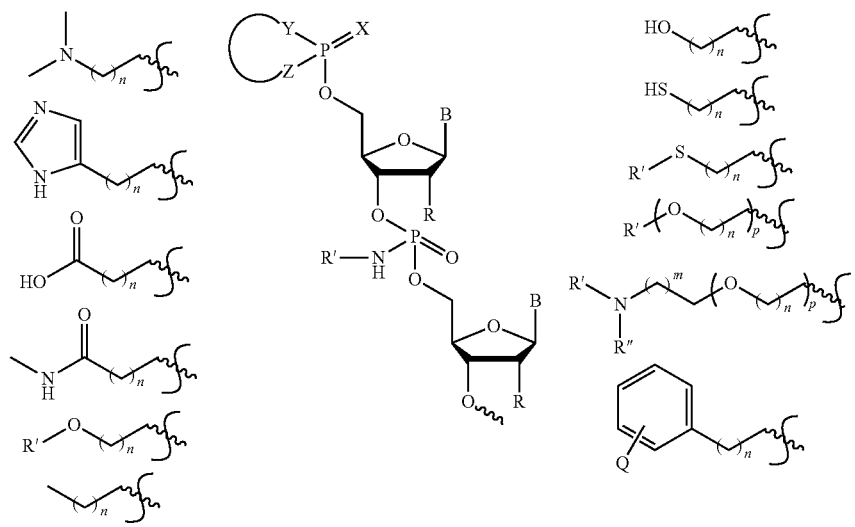
Phosphate bridge mimics between position 1 and 2 (5'-end)
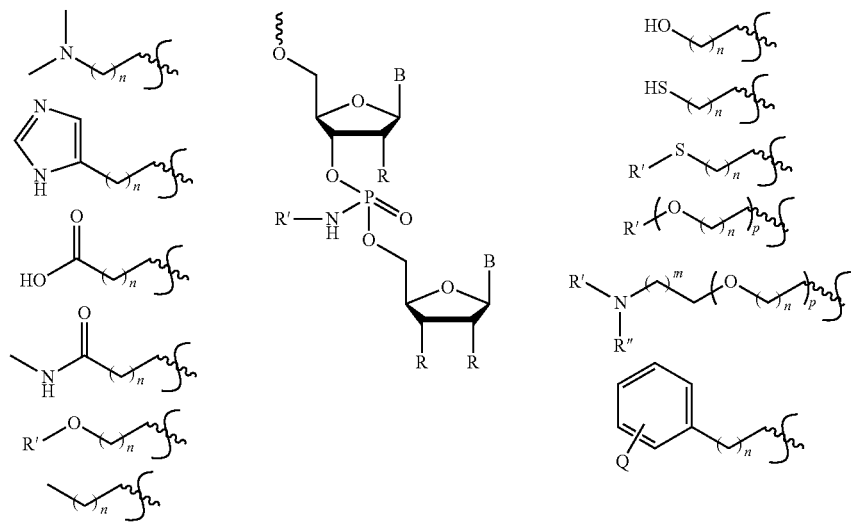
Phosphate bridge mimics between the last two nucleosides at the 3'-end.

TABLE A-continued
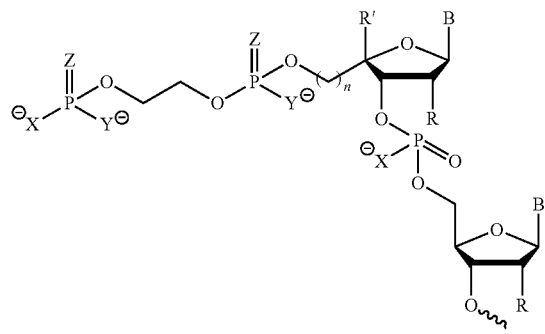
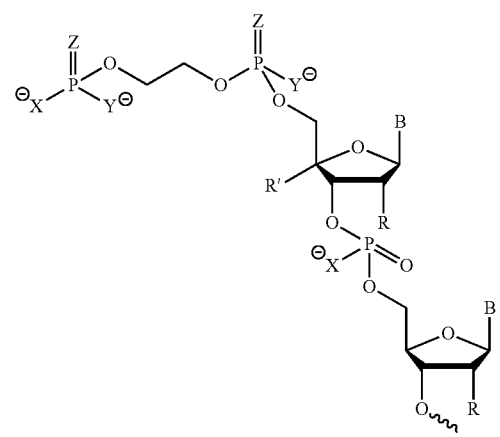
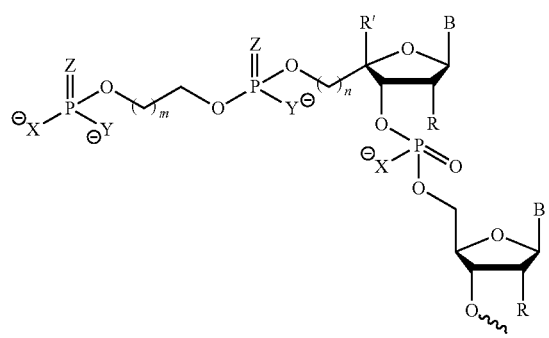
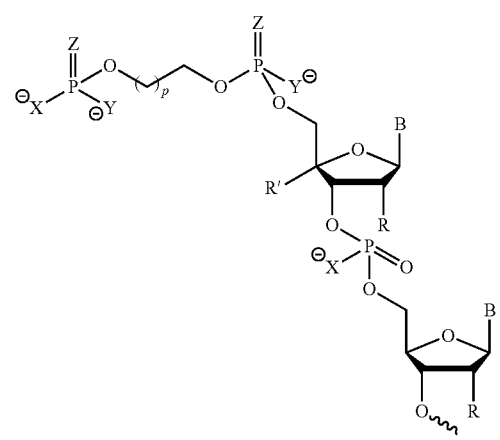

TABLE A-continued
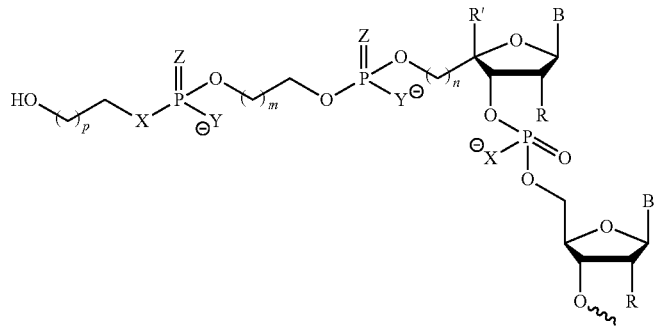
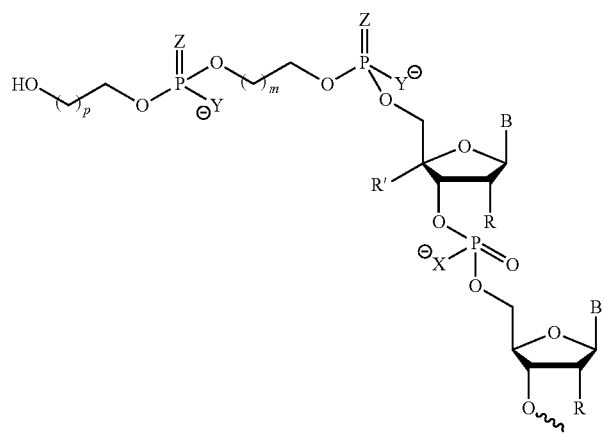
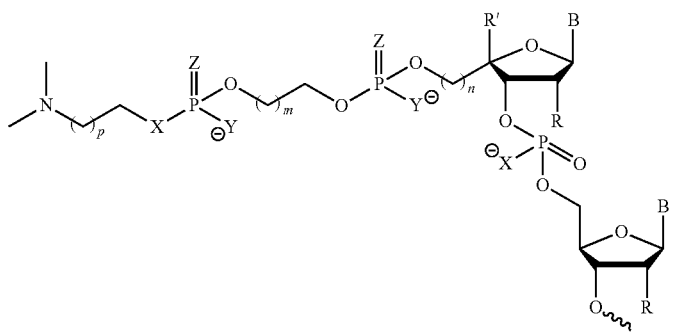
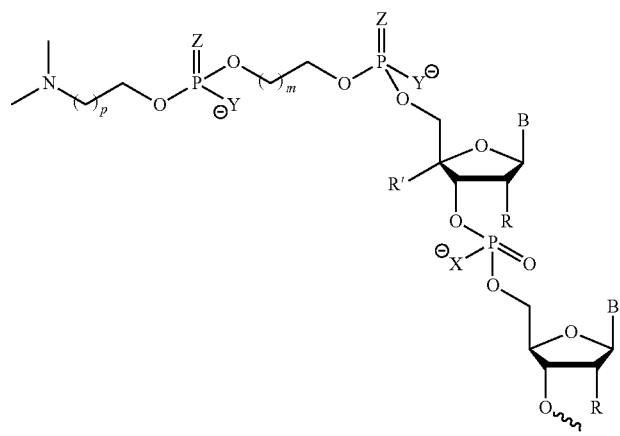

TABLE A-continued
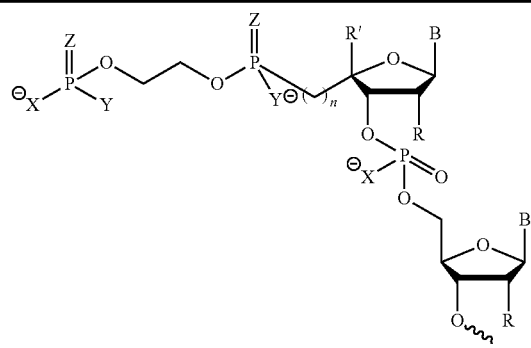
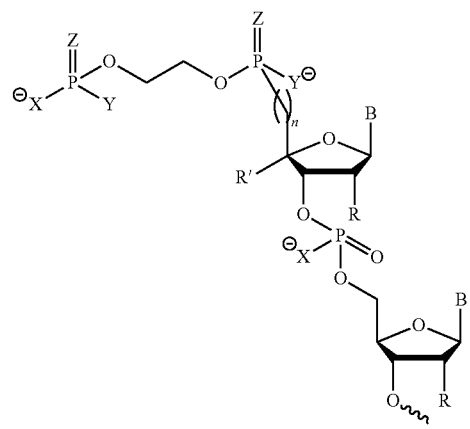
X: O, S
Y: S, $BH_3^-$, F, Me, $CF_3$, H, NHR
Z: O, $CH_2$, CHF, $CF_2$, OCH(Me)—
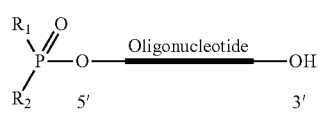
a) Aryl amidates: McGuigan
   $R_1$ = OAr
   $R_2$ = AA ester
b) HepDirect esters:
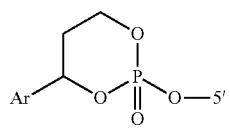
c) Lipid esters:
   $R_1$ = O—$(CH_2)_{17}CH_3$
   $R_2$ = OH
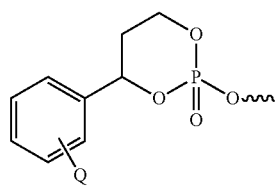
Substituted aryl with Q for anchoring other ligands TABLE A-continued

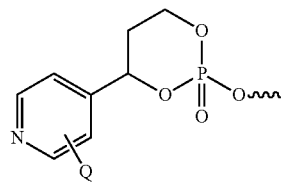

In one embodiment, the oligonucleotides of the invention comprise internucleoside linkages selected from phosphorus and non-phosphorus containing internucleoside. In one example, the phosphorus containing internucleoside includes, but not limited to, phosphodiester, phosphorothioates, chiral phosphorothioates, phosphorodithioates, phosphotriesters, aminoalkylphosphotriesters, methyl and other alkyl phospho-nates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In one embodiment, oligonucleotides of the invention comprise one or more internucleoside linkages that don't contain a phosphorus atom. Such oligonucleotides include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above non-phosphorus containing internucleoside linking group include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In one embodiment, oligonucleotides of the invention comprise one or more neutral internucleoside linkage that are non-ionic. Suitable neutral internucleoside linkages include but are not limited to phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-0-$CH_2$—O-5'), and thioformacetal (3'-S—$CH_2$—O-5'); nonionic linkages containing siloxane (dialkylsiloxane), carboxylate ester, carboxamide, sulfide, sulfonate ester and/or amides (See for example: Carbohydrate Modifications in Antisense Research; Y. S. Sanghvi and P. D. Cook Eds. ACS Symposium Series 580; Chapters 3 and 4, (pp. 40-65)); and nonionic linkages containing mixed N, O, S and $CH_2$ component parts.

In one embodiment, the non-phosphodiester backbone linkage is selected from a group consisting of phosphorothioate, phosphorodithioate, alkyl-phosphonate and phosphoramidate backbone linkages.

In one aspect, the present invention provides an oligonucleotide comprising at least one modified nucleoside of formula selected from (Ia), (IIa), (IIIa), (IIIb) (IVa), (Va), (IVc) and (Vc) optionally in combination with a natural base (and derivatives thereof) or modified nucleobase. See the U.S. Provisional Application entitled "Nucleic Acid Modifications," by Manoharan et al., filed Jul. 7, 2009, for examples of different nucleobase modifications. For instance, the modified base includes high affinity modification such as G-clamp and its analogs; phenoxazines and their analogs; and bi- and tricyclic non-natural nucleoside bases. The invention further provides modified oligonucleotides with 3', 5' or both 3' and 5' terminal phosphate or phosphate mimics. The phosphate or phosphate mimics includes α- and/or β-configuration with respect to the sugar ring or combinations thereof. The phosphate or phosphate mimics include but not limited to: natural phosphate, phosphorothioate, phosphorodithioate, borano phosphate, borano thiophospahte, phosphonate, halogen substituted phosphoantes, phosphoramidates, phosphodiester, phosphotriester, thiophosphodiester, thiophosphotriester, diphosphates and triphosphates. The invention also provides sugar-modified purine dimers at 3' and 5'-terminals (i.e. 5'/3'-GG, AA, AG, GA, GI, IA etc.), where the purine bases are natural or chemically modified preferably at the 2, 6, 7, and 8 positions; $N^2$ and $N^6$ exocyclic amine positions of the base or combinations thereof. The nucleoside at position 1 (5'-end) may contain a 2' and/or 4'-sugar modified natural and modified nucleobase, purine or pyrimidine nucleobase mimics or combinations thereof. The modified oligonucleotides may be single stranded siRNA (ss siRNA), double stranded siRNA (ds siRNA), micro RNA, antimicroRNA, supermir, aptamer, antisense oligonucleotide, decoy oligonucleotide, ribozymes, immunostimulatory oligonucleotide, RNAa activator or U1 adaptor, containing a motif selected from the modifications described herein and combinations of modifications thereof. The invention provides that said modified oligonucleotide is one of the strands or constitutes for both strands of a double strands oligonucleotide such as ds siRNA. In one embodiment, the modified oligonucleotide is the guide or antisense strand. In another embodiment, the modified oligonucleotide is sense or passenger strand of the double stranded siRNA. In still another embodiments, both strands of ds siRNA bear modified oligoncleotides.

Another aspect of the invention relates to the oligonucleotides disclosed in this application modified with a nucleosidic end cap. Oligonucleotides modified in this manner can be used in methods for improving nuclease stability. Representative nuclesidic end caps may be found in U.S. Provisional Application No. 61/223,665, entitled "Oligonucleotide End Caps" by Manoharan et al., filed Jul. 7, 2009.

In one embodiment, the oligonucleotide comprises at least one ligand conjugate.

In one embodiment, the oligonucleotide comprises two or more ligand conjugates.

In one embodiment, the oligonucleotide is a double-stranded oligonucleotide.

In one embodiment, only one strand comprises the modified nucleoside.

In one embodiment, both strands comprise the modified nucleoside.

In one embodiment, the modified nucleoside is the same in the two strands.

In one embodiment, the modified nucleoside is different in the two strands.

In one embodiment, the oligonucleotide is a single-stranded oligonucleotide.

In one embodiment, the oligonucleotide has a hairpin structure.

In one embodiment, the oligonucleotide is an RNAi agent, an antisense, an antagomir, a microRNA, a pre-microRNA, an antimir, a ribozyme, a decoy oligonucleotide, an immunostimulatory oligonucleotide, RNAa activator, U1 adaptor or an aptamer oligonucleotide.

In one embodiment, the oligonucleotide is a single-stranded siRNA.

In one embodiment, the RNAi agent is double stranded and only the sense strand comprises the modified nucleoside.

In one embodiment, the RNAi agent is double stranded and only the antisense strand comprises the modified nucleoside.

In one embodiment, the RNAi agent is double-stranded and both the sense and the antisenss strands comprise at least one modified nucleoside.

In one embodiment, the modified nucleoside is the same in both the sense and the antisenss strands.

In one embodiment, the sense and the antisense strands comprise different modified nucleosides.

The nucleoside and oligonucleotides described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In general, the term "oligomeric compound" refers to a contiguous sequence of linked monomelic subunits. In general each linked monomelic subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups.

Oligonucleotides

In the context of this invention, the term "oligonucleotide" refers to a polymer or oligomer of nucleotide or nucleoside monomers consisting of naturally occurring bases, sugars and intersugar (backbone) linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The nucleic acids used herein can be single-stranded or double-stranded. A single stranded oligonucleotide may have double stranded regions and a double stranded oligonucleotide may have regions of single-stranded regions. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNAs, aptamers, antagomirs, triplex-forming oligonucleotides, decoy oligonucleotides, immunostimulatory oligonucleotides, RNA activators, U1 adaptors and single-stranded RNAi agents.

Oligonucleotides of the present invention may be of various lengths. In particular embodiments, oligonucleotides may range from about 10 to 100 nucleotides in length. In various related embodiments, oligonucleotides, single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

The oligonucleotides of the invention may comprise any oligonucleotide modification described herein and below. In certain instances, it may be desirable to modify one or both strands of a dsRNA. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, oligonucleotides of the invention comprises 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Double-Stranded Oligonucleotides

In one embodiment, the invention provides double-stranded ribonucleic acid (dsRNA) molecules for inhibiting the expression of the target gene (alone or in combination with a second dsRNA for inhibiting the expression of a second target gene) in a cell or mammal, where the dsRNA comprises an antisense strand comprising a region of complementarity which is complementary to at least a part of an mRNA formed in the expression of the target gene, and where the region of complementarity is less than 30 nucleotides in length, generally 19-24 nucleotides in length, and where the dsRNA, upon contact with a cell expressing said target gene, inhibits the expression of the target gene. The dsRNA comprises two RNA strands that are sufficiently complementary to hybridize to form a duplex structure. Generally, the duplex structure is between 15 and 30, more generally between 18 and 25, yet more generally between 19 and 24, and most generally between 19 and 21 base pairs in length. In one embodiment, longer dsRNAs of between 25 and 30 base pairs in length are preferred. In one embodiment, shorter dsRNAs of between 10 and 15 base pairs in length are preferred. In another embodiment, the dsRNA is at least 21 nucleotides long and includes a sense RNA strand and an antisense RNA strand, where the antisense RNA strand is 25 or fewer nucleotides in length, and the duplex region of the dsRNA is 18-25 nucleotides in length, e.g., 19-24 nucleotides in length.

In certain embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, or 30 nucleotide pairs in length.

In certain embodiments, the antisense strand of a double-stranded oligonucleotide is equal to or at least 14, 15, 16, 17, 18, 19, 20, 21, 22, 23, 23, 24, 25, 26, 27, 28, 29, or 30 nucleotides in length.

In certain embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, or 30 nucleotides in length.

Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s).

In a preferred embodiment, the target gene is a human target gene. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, and combinations thereof.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above the dsRNAs of the invention can comprise at least one strand of a length of minimally 21 nt. It can be reasonably expected that shorter dsRNAs comprising a known sequence minus only a few nucleotides on one or both ends may be similarly effective as compared to the dsRNAs of the lengths described above. Hence, dsRNAs comprising a partial sequence of at least 15, 16, 17, 18, 19, 20, or more contiguous nucleotides, and differing in their ability to inhibit the expression of the target gene by not more than 5, 10, 15, 20, 25, or 30% inhibition from a dsRNA comprising the full sequence, are contemplated by the invention. Further dsRNAs that cleave within the target sequence can readily be made using the target gene sequence and the target sequence provided.

Double-stranded and single-stranded oligonucleotides that are effective in inducing RNA interference are also referred to as siRNA, RNAi agent and/or iRNA agent. These RNA interference inducing oligonucleotides associate with a cytoplasmic multi-protein complex known as RNAi-induced silencing complex (RISC). In certain embodiments, single-stranded and double stranded RNAi agents are sufficiently long that they can be cleaved by an endogenous molecule, e.g. by Dicer, to produce smaller oligonucleotides that can enter the RISC machinery and participate in RISC mediated cleavage of a target sequence, e.g. a target mRNA.

The present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides coupled to additional nucleotide sequences taken from the region contiguous to the selected sequence in the target gene.

The dsRNA of the invention may contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the target gene, the dsRNA generally does not contain any mismatch within the central 13 nucleotides. The methods described within the invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

In certain embodiments, the sense-strand comprises a mismatch to the antisense strand. In certain embodiments, the mismatch is within 5 nucleotides from the end of the double stranded region, for example at positions 5, 4, 3, 2, or 1 from the end of the duplex region. Preferably, the mismatch is within 5 nucleotides from the end of the duplex corresponding to the 3'-end of the sense strand. In some embodiments, the mismatch is located in the target cleavage site region. In one embodiment, the sense strand comprises no more than 1, 2, 3, 4 or 5 mismatches to the antisense strand. In preferred embodiments, the sense strand comprises no more than 3 mismatches to the antisense strand.

In one embodiment, the sense strand comprises a nucleobase modification, e.g. an optionally substituted natural or non-natural nucleobase, a universal nucleobase, in the target cleavage site region.

In certain embodiments, the sernse strand comprises an abasic nucleotide in the target cleavage site region.

The "target cleavage site" herein means the backbone linkage in the target gene, e.g. target mRNA, or the sense strand that is cleaved by the RISC mechanism by utilizing the iRNA agent. And the "target cleavage site region" comprises at least one or at least two nucleotides on both side of the cleavage site. For the sense strand, the target cleavage site is the backbone linkage in the sense strand that would get cleaved if the sense strand itself was the target to be cleaved by the RNAi mechanism. The target cleavage site can be determined using methods known in the art, for example the 5'-RACE assay as detailed in Soutschek et al., *Nature* (2004) 432, 173-178. As is well understood in the art, the cleavage site region for a conical double stranded RNAi agent comprising two 21-nucleotides long strands (wherein the strands form a double stranded region of 19 consecutive basepairs having 2-nucleotide single stranded overhangs at the 3'-ends), the cleavage site region corresponds to positions 9-12 from the 5'-end of the sense strand.

In one embodiment, at least one end of the dsRNA has a single-stranded nucleotide overhang of 1 to 4, generally 1 or 2 nucleotides. In certain embodiments, both ends of the double-stranded region have a single-stranded nucleotide overhang of 1 to 4, generally 1 or 2 nucleotides. As used herein, the term "overhang" refers to a double-stranded structure where at least one end of one strand is longer than the corresponding end of the other strand forming the double-stranded structure.

In some embodiments it is particularly preferred, e.g., to enhance stability, to include particular nucleobases in the single-stranded overhangs, or to include modified nucleotides or nucleotide surrogates, in single-strand overhangs. For example, it can be desirable to include purine nucleotides in overhangs. In some embodiments all or some of the bases in the single strand overhang will be modified, e.g., with a modification described herein. Modifications in the single-stranded overhangs can include any oligonucleotide modification described herein and below, e.g., the use of sugars with modifications at the 2' position, e.g., the use of deoxyribonucleotides, e.g., deoxythymidine, instead of ribonucleotides, and modifications in the phosphate group, e.g., phosphothioate modifications. Overhangs need not be homologous with the target sequence. In certain embodiments, the single strand overhangs are asymmetrically modified with a modification described herein, e.g. a first single-stand overhang comprises a modification that is not present in a second single-strand overhang.

In certain embodiments, the unpaired nucleotide adjacent to the terminal nucleotide base pair on the end of the double-stranded region is a purine.

In one embodiment, the single-stranded overhang has the sequence 5'-GCNN-3', where N is independently for each occurrence, A, G, C, U, dT, dU or absent. In certain embodiments, the single-stranded overhang has the sequence 5'-N,N-3', wherein N is independently for each occurrence a modified or unmodified nucleotide described herein and below. dsRNAs having at least one nucleotide overhang have unexpectedly superior inhibitory properties than their blunt-ended counterparts. Without wishing to be bound, presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Generally, the antisense strand of the dsRNA has a nucleotide overhang at the 3'-end, and the 5'-end is blunt.

In one embodiment, the antisense strand of the dsRNA has 1-10 nucleotides overhangs each at the 3' end and the 5' end over the sense strand. In one embodiment, the sense strand of the dsRNA has 1-10 nucleotides overhangs each at the 3' end and the 5' end over the antisense strand.

In certain embodiments, one strand has at least one stretch of 1-5 single-stranded nucleotides in the double-stranded region. In certain other embodiments, both strands have at least one stretch of 1-5 single-stranded nucleotides in the double stranded region. When both strands have a stretch of 1-5 single-stranded nucleotides in the double stranded region, such single-stranded nucleotides may be opposite to each other or they can be located such that the second strand has no single-stranded nucleotides opposite to the single-stranded oligonucleotides of the first strand and vice versa.

In certain embodiments, at least one strand of the double-stranded oligonucleotide has a ZXY structure, such as is described in PCT Application No. PCT/US2004/07070 filed on Mar. 8, 2004, contents of which are hereby incorporated in their entireties.

The dsRNAs of the invention may comprise any oligonucleotide modification described herein and below. In certain instances, it may be desirable to modify one or both strands of a dsRNA. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, the dsRNA is chemically modified to enhance stability. In one preferred embodiment, one or more of the nucleotides in the overhang is replaced with a nucleoside thiophosphate.

The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region where the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression.

The present invention also includes dsRNAs where the two strands are linked together. The two strands can be linked to each other at both ends, or at one end only. When the two strands are linked to each other at both ends, 5'-end of one strand is linked to the 3'-end of the second strand and vice versa. The two strands can be linked together by a polynucleotide linker such as $(dT)_n$; where n is 4-10. When the two strands are linked to each other through a polynucleotide linker at one end only, the oligonucleotide forms a hairpin. The two strands can also be linked together by a non-nucleosidic linker, e.g. a linker described herein. It will be appreciated by one of skill in the art that any oligonucleotide chemical modifications or variations describe herein can be used in the polynucleotide linker.

Hairpin RNAi agents will have a duplex region equal to or at least 16, 17, 18, 19, 29, 21, 22, 23, 24, or 25 nucleotide pairs. The duplex region will may be equal to or less than 200, 100, or 50, in length. In one embodiment, ranges for the duplex region are 15-30, 17 to 23, 19 to 23, and 19 to 21 nucleotides pairs in length. The hairpin may have a single strand overhang or terminal unpaired region, in some embodiments at the 3', and in one embodiment on the antisense side of the hairpin. In one embodiment, the overhangs are 1-4 and more preferably 2-3 nucleotides in length.

The RNAi agents of the invention can target more than one RNA region. For example, an RNAi agent can include a first and second sequence that are sufficiently complementary to each other to hybridize. The first sequence can be complementary to a first target RNA region and the second sequence can be complementary to a second target RNA region. The first and second sequences of the RNAi agent can be on different RNA strands, and the mismatch between the first and second sequences can be less than 50%, 40%, 30%, 20%, 10%, 5%, or 1%. The first and second sequences of the RNAi agent can be on the same RNA strand, and in a related embodiment more than 50%, 60%, 70%, 80%, 90%, 95%, or 1% of the RNAi agent can be in bimolecular form. The first and second sequences of the RNAi agent can be fully complementary to each other.

RNAi agents of the invention can be used to target two or more RNA regions where the RNA regions differ from each other at 1, 2, 3, 4 or 5 positions. As used in this context, the phrase "differ from each other" refers to the RNA regions having different nucleotides at that position. In these cases the RNAi agent strand that is complementary to the RNA region to be targeted comprises universal nucleobases at positions complementary to where the RNA regions are different from each other. For example, the antisense strand of the double-stranded RNAi agent comprises universal nucleobases at positions complementary to where the RNA regions to be targeted do not match each other.

As used herein, a universal nucleobase is any modified, unmodified, naturally occurring or non-naturally occurring nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4, 5-trimethylphenyl, 4-methylinolyl, 4,6-dimethylindolyl, phenyl, napthalenyl, anthracenyl, phenanthracenyl, pyrenyl, stilbenzyl, tetracenyl, pentacenyl, and structural derivatives thereof.

Sugar Modifications

An oligonucleotide of the invention can further include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R═H, alkyl, cycloalkyl, aryl, aralkyl, heteroaryl or sugar); polyethyleneglycols (PEG), $O(CH_2CH_2O)_nCH_2CH_2OR$; "locked" nucleic acids, e.g., LNA in which the 2' hydroxyl is connected by a methylene bridge to the 4' carbon of the same ribose sugar and ENA in which the 2' hydroxyl is connected by an ethylene bridge, to the 4' carbon of the same ribose sugar; O-AMINE (AMINE═$NH_2$; alkylamino, dialkylamino, heterocyclyl amino, arylamino, diaryl amino, heteroaryl amino, diheteroaryl amino, ethylene diamine, polyamino or aminoalkoxy) and $O(CH_2)_nAMINE$, (e.g., AMINE═$NH_2$, alkylamino, dialkylamino, heterocyclyl amino, arylamino, diaryl amino, heteroaryl amino, diheteroaryl amino, ethylene diamine, polyamino or aminoalkoxy). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE═$NH_2$; alkylamino, dialkylamino, heterocyclyl, arylamino, diaryl amino, heteroaryl amino, or diheteroaryl amino); NHC(O)R (R=alkyl, cycloalkyl, aryl, aralkyl, heteroaryl, or sugar); cyano; mercapto; alkyl-thio-alkyl; thioalkoxy; alkyl; cycloalkyl; aryl; alkenyl and alkynyl, which may be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Modification to the sugar group may also include replacement of the 4'-O with a sulfur, nitrogen or $CH_2$ group. Other modifications to the sugar group include deletion of the C2'

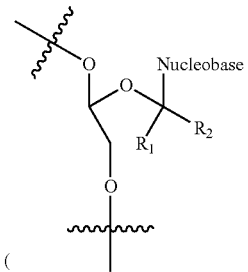

or deletion of 4'-O

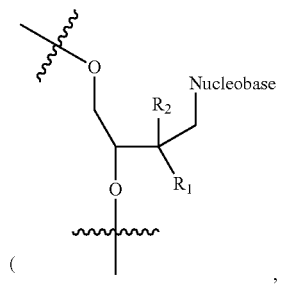

where $R_1$ and $R_2$ independently are H, halogen, $OR_3$, or alkyl; and $R_3$ is H, alkyl, cycloalkyl, aryl, aralkyl, heteroaryl or sugar).

Preferred substitutents are 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O—$CH_2CH_2N$($CH_2CH_2NMe_2$) and 2'-O-dimethylaminoethyloxyethyl (2'-O-DMAEOE).

One or more nucleotides of an oligonucleotide may have L-sugar with modifications in place of the modified nucleoside in its entity pursuant to the invention described. The L-sugar has the same sugar and base modification or combinations thereof as in D-sugar. One or more nucleotides of an oligonucleotide having the L-sugar may have a 2'-5' linkage or inverted linkages, e.g. 3'-3', 5'-5',2'-2' or 2'-3' linkages. These linkages can be placed between two L-sugar moieties, between L- and D-sugars or between two D-sugars in an oligonucleotide bearing a modified L-nucleoside.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. In certain embodiments, the 5'-end of the oligonucleotide comprises the modification

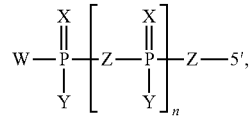

wherein W, X and Y are each independently selected from the group consisting of O, OR(R is hydrogen, alkyl, aryl), S, Se, $BR_3$ (R is hydrogen, alkyl, aryl), C (i.e. an alkyl group, an aryl group, etc. . . . ), H, $NR_2$ (R is hydrogen, alkyl, aryl), or OR (R is hydrogen, alkyl or aryl); Z is independently for each occurrence O, S, $CH_2$, or NR (R is hydrogen, alkyl, aryl); and n is 0-2.

Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-$CH_2$—), 5'-alkyletherphosphonates (R=alkylether=methoxymethyl (MeOCH$_2$—), ethoxymethyl, etc., e.g. RP(OH)(O)—O-5'-); two or more phosphates or all phopshophate mimics described with separation by substituted or unsubstituted alkyl, alkenyl or alkynyl spacings: e.g., ((HO)2(X)P—O[CH$_2$)$_a$—O—P(X)(OH)—O]$_b$-5', ((HO)2(X)P—O[—(CH$_2$)$_a$—P(X)(OH)—O]$_b$-5', ((HO)2(X)P—[—(CH$_2$)$_a$—O—P(X)(OH)—O]$_b$-5'; dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[—(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[—(CH$_2$)$_a$—P(X)(OH)—O]$_b$-5', Me$_2$N[—(CH$_2$)$_a$—P(X)(OH)—O]$_b$-5'. Other embodiments include replacement of oxygen/sulfur with BH$_3$, BH$_3^-$ and/or Se. In one occurrence, at terminals of the oligonucleotides, the phosphate and phosphoate mimics described are in the β configuration to the sugar moiety and in another occurrence the phosphate mimic is in the α configuration to the sugar moiety. In yet another occurrence the sugar comprises two phosphate moieity, wherein one is in the α configuration and the other is in the β configuration. present.

In another embodiment, the phosphate groups described above are placed at the 3'-end of the oligonucleotided In one embodiment, the configuration of phosphate or phosphate mimics at 5' terminal is β to the sugar moiety.

In another embodiment, the configuration of phosphate or phosphate mimics at 5' terminal is α to the sugar moiety.

In one embodiment, the configuration of phosphate or phosphate mimics at 3' terminal is β to the sugar moiety.

In another embodiment, the configuration of phosphate or phosphate mimics at 3' terminal is α to the sugar moiety.

In another embodiment, both α and β phosphate or phosphate mimics are simultaneously present at the terminals Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C, psoralen and derivatives thereof.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); or NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

Placement within an Oligonucleotide

Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 5'-5', 3'-3',3'-2', 2'-5',2'-3' or a 2'-2' linkage, preferably a 2'-5' linkage. In certain embodiments, the last nucleotide on the terminal end is linked via an inverted linkages, e.g. 3'-3', 5'-5',2'-2' or 2'-3' linkage to the rest of the oliogonucleotide.

An oligonucleotide may comprise at least one 5'-pyrimidine-purine-3' (5'-PyPU-3') dinucleotide motif wherein the pyrimidine ribose sugar is modified at the 2'-position. In certain embodiments, the pyrimidine ribose sugar is replaced by a non ribose moiety, e.g., a six membered ring. In certain other embodiments, the oligonucleotide comprises at least one 5'-pyrimidine-purine-3' (5'-PyPu-3') dinucleotide wherein the ribose sugar of the pyrimidine is modified with a modification chosen independently from a group consisting of 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA). In one embodiment, the 5'-most pyrimidines in all occurrences of sequence motif 5'-pyrimidine-purine-3' (5'-PyPu-3') dinucleotide in the oligonucleotide comprise a sugar 2'-modification.

In certain embodiments, the oligonucleotide comprises at least one 5'-PyPu-3' dinucleotide motif where the C5 position of the pyrimidine is conjugated with a stabilizing moiety, e.g., a cationic group. In one embodiment, pyrimidines in all 5'-PyPu-3' dinucleotide motif comprise a stabilizing moiety at the C5 position.

In certain embodiments, the oligonucleotide comprises at least one 5'-PyPu-3' dinucleotide motif where the N$^2$, N$^6$, and/or C$^8$ position of the purine is conjugated with a stabilizing moiety, e.g., a cationic group. In one embodiment, purines in all 5'-PyPu-3' dinucleotide motifs comprise a stabilizing moiety at the N$^2$, N$^6$, and/or C$^8$ position.

In certain embodiments, both the pyrimidine and purine in the 5'-PyPu-3' dinucleotide motif are conjugated with stabilizing groups.

In certain embodiments, the internucleotide linkage between 3'- of a pyrimidine and 5'- of a purine is a non-phosphodiester linkage described herein.

In certain embodiments, the both the pyrimidine and the purine in a 5'-PyPu-3' dinucleotide motif are unmodified and the internucleotide linkage between them is a non-phosphodiester linkage described herein.

In certain embodiments, both the pyrimidine and the purine in a 5'-PyPu-3' dinucleotide motif comprise unmodified sugars, e.g., 2'-OH and at least one of them comprises a nucleobase modification. In one embodiment, both the pyrimidine and the purine in a 5'-PyPu-3' dinucleotide motif comprise unmodified sugars, e.g., 2'-OH and both of them comprise a nucleobase modification.

In certain embodiments, the oligonucleotide comprises at least one 5'-PyPu-3'-dinucleotide motif where the pyrimide comprises a modification at the 2'-position, the internucleotide linkage is a non-phosphodiester linkage and at least one of the pyrimidine and the purine comprises a nucleobase modification. In one embodiment, the pyrimined comprises the nucleobase modification. In another embodiment, the purine comprises the nucleobase modification. In yet another embodiment, both the pyrimidine and the purine comprise the nucleobase modification.

In certain embodiments, the oligonucleotide comprises at least one 5'-PyPu-3'-dinucleotide motif where the purine comprises a modification at the 2'-position, the internucleotide linkage is a non-phosphodiester linkage and at least one of the pyrimidine and the purine comprises a nucleobase modification. In one embodiment, the pyrimined comprises the nucleobase modification. In another embodiment, the purine comprises the nucleobase modification. In yet another embodiment, both the pyrimidine and the purine comprise the nucleobase modification.

In one embodiment, the single stranded siRNA (ss siRNA) and double stranded siRNA (ds siRNA) of the invention comprises a motif selected from the group consisting of:
  (a) 2'-modified uridines in all occurrences of the sequence motif 5'-uridine-adenosine-3' (5'-UA-3'),
  (b) 2'-modified uridines in all occurrences of the sequence motif 5'-uridine-guanosine-3' (5'-UG-3'),
  (c) 2'-modified cytidines in all occurrences of the sequence motif 5'-cytidine-adenosine-3' (5'-CA-3'),
  (d) 2'-modified cytidines in all occurrences of the sequence motif 5'-cytidine-Guanosine-3' (5'-CA-3'),
  (e) 2'-modified 5'-most uridines in all occurrences of the sequence motif 5'-uridine-uridine-3' (5'-UU-3'),
  (f) 2'-modified 5'-most cytidines in all occurrences of the sequence motif 5'-cytidine-cytidine-3' (5'-CC-3'),
  (g) 2'-modified cytidines in all occurrences of the sequence motif 5'-cytidine-uridine-3' (5'-CU-3'),
  (h) 2'-modified uridines in all occurrences of the sequence motif 5'-uridine-cytidine-3' (5'-UC-3'), and
  (h) combinations thereof;
and wherein siRNA comprises at least one modification at internucleotide linkage, nucleobase and/or 2' sugar modification. Examples of the non-phosphodiester modification includes, but not limited to phosphorothioate, phosphorodithioate, phosphotriesters, aminoalkylphosphotriesters, methyl and other alkyl phosphonates, selenophosphates, phosphoramidates and boranophosphates. Examples of the nucleobase modifications include, but not limited to: C-5 pyrimidine with an alkyl group or aminoalkyls and other cationic groups such as guanidinium and amidine functionalities, SH or OH, $N^2$— and $N^6$— of purines with an alkyl group or aminoalkyls and other cationic groups such as guanidinium and amidine functionalities or SH and OH, G-clamps, guanidinium G-clamps, and pseudouridine known in the art or G-clamps and pseudourines provided herein in. Examples of 2' modifications includes those know in the art, as well as ones disclosed herein. In one example, when there is a 2' OH moiety present in the said motif, at least either internucleotide linkage or nucleobase or both must be modified. In another example, 2'-position of the sugar of the 3'-most nucleoside is modified but not of the 5'-most nucleoside and vice versa, then at least either the internucleotide linkage or nucleobase of the 5'-most or 3'-most or both the nucleobase of the motif or both internucleotide linkage and nucleobase must be modified. In another example, both nucleoside in the motif bear unmodified ribo-sugar (i.e., 2'-OH on both nucleoside), then at least either the internucleotide linkage or nucleobase of the 5'-most or 3'-most or both the nucleobase, or both internucleotide linkage and at least one of the nucleobases of the motif must be modified. The preferred nucleobase modification cation bears a cationic amino group connected via an appropriate alkyl, alkenyl or a tether with an amide linkages.

A double-stranded oligonucleotide may include at least one 5'-uridine-adenine-3' (5'-UA-3') dinucleotide wherein the uridine is a 2'-modified nucleotide, a 5'-uridine-guanine-3' (5'-UG-3') dinucleotide, wherein the 5'-uridine is a 2'-modified nucleotide, a 5'-cytidine-adenine-3' (5'-CA-3') dinucleotide, wherein the 5'-cytidine is a 2'-modified nucleotide, a 5'-cytidine-guanine-3' (5'-CG-3') dinucleotide, wherein the 5'-cytidine is a 2'-modified nucleotide, a 5'-uridine-uridine-3' (5'-UU-3') dinucleotide, wherein the 5'-uridine is a 2'-modified nucleotide, a 5'-cytidine-cytidine-3' (5'-CC-3') dinucleotide, wherein the 5'-cytidine is a 2'-modified nucleotide, a 5'-cytidine-uridine-3' (5'-CU-3') dinucleotide, wherein the 5'-cytidine is a 2'-modified nucleotide, a 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

Modifications and monomers described herein may be used to asymmetrically modified a double-stranded oligonucleotide. An asymmetrically modified double-stranded oligonucleotide is one in which one strand has a modification which is not present on the other strand. As such, an asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. For example, an asymmetrical modification can confer resistance to degradation, an alteration in half life; target the oligonucleotide to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting. Asymmetrical modifications can include those in which only one strand is modified as well as those in which both are modified.

When the two strands of double-stranded oligonucleotide are linked together, e.g. a hairpin or a dumbbell, the two strands of the double stranded region may also be strands forming asymmetrically modified. For example, first strand of the double-stranded region comprises at least one asymmetric modification that is not present in the second strand of the double stranded region or vice versa.

While not wishing to be bound by theory or any particular mechanistic model, it is believed that asymmetrical modification allows a double-stranded RNAi agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., a ligand, can add large bulky groups that, e.g., can interfere with the cleavage activity of the RISC complex, such modifications are preferably placed on the sense strand. Thus, ligands, especially bulky ones (e.g. cholesterol), are preferentially added to the sense strand. The ligand may be present at either (or both) the 5' or 3' end of the sense strand of a RNAi agent.

Each strand can include one or more asymmetrical modifications. By way of example: one strand can include a first asymmetrical modification which confers a first property on the oligonucleotide and the other strand can have a second asymmetrical modification which confers a second property on the oligonucleotide. For example, one strand, e.g., the sense strand can have a modification which targets the oligonucleotide to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, because the modifications affect other properties as well.

Multiple asymmetric modifications can be introduced into either or both of the sense and antisense strand. A strand can have at least 1, 2, 3, 4, 5, 6, 7, 8, or more modifications and all or substantially all of the monomers, e.g., nucleotides of a strand can be asymmetrically modified.

In certain embodiments, the asymmetric modifications are chosen so that only one of the two strands of double-stranded RNAi agent is effective in inducing RNAi Inhibiting the induction of RNAi by one strand may reduce the off target effects due to cleavage of a target sequence by that strand.

Oligonucleotide Production

The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Ligands

A wide variety of entities can be coupled to the oligonucleotides of the present invention. Ligands can include naturally occurring molecules, or be recombinant or synthetic molecules. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from cellular compartments such as the endosome, lysosome, endoplasmic reticulum (ER), golgi apparatus, microtubule, peroxisome, or other vesicular bodies within the cell, to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GAL4 peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

Methods of Use

One aspect of the present invention relates to a method of modulating the expression of a target gene in a cell. The method comprises: (a) providing a composition of the invention; (b) contacting a cell with the composition; and (c) allowing the cell to internalize the composition. The method can be performed in vitro, ex vivo or in vivo, e.g., to treat a subject identified as being in need of treatment by a composition of the invention.

In certain embodiments, the cell is a mammalian cell.

In yet another aspect, the invention provides a method for modulating the expression of the target gene in a mammal. The method comprises: administering a composition featured in the invention to the mammal such that expression of the target gene is modulated. The composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection.

Target genes include genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

The phrases "2'-modification" and "2'-modified nucleotide" refer to a nucleotide unit having a sugar moiety, for example a ribosyl moiety, that is modified at the 2'-position such that the hydroxyl group (2'-OH) is replaced by, for example, —F, —H, —CH$_3$, —CH$_2$CH$_3$, —OCH$_3$, —OCH$_2$CH$_3$, —OCH$_2$CH$_2$OMe, —OCH$_2$C(═O)NHMe, —OCH$_2$-(4'-C) (a so-called "LNA sugar modification"), or —OCH$_2$CH$_2$-(4'-C) (a so-called "ENA sugar modification"). For example, the phrases "2'-fluoro modification" and "2'-fluoro modified nucleotide" refer to a nucleotide unit having a sugar moiety, for example a ribosyl moiety, that is modified at the 2'-position such that the hydroxyl group (2'-OH) is replaced by a fluoro group (2'-F). U.S. Pat. Nos. 6,262,241, and 5,459,255 (both of which are incorporated by reference), are drawn to, inter alia, methods of synthesizing 2'-fluoro modified nucleotides and oligonucleotides.

The phrase "antisense strand" as used herein, refers to a polynucleotide that is substantially or 100% complementary to a target nucleic acid of interest. An antisense strand may comprise a polynucleotide that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of both polynucleotides that are formed from two separate strands, as well as unimolecular polynucleotides that are capable of forming hairpin structures. The terms "antisense strand" and "guide strand" are used interchangeably herein.

The phrase "sense strand" refers to a polynucleotide that has the same nucleotide sequence, in whole or in part, as a target nucleic acid such as a messenger RNA or a sequence of DNA. The sense strand is not incorporated into the functional riboprotein RISC. The terms "sense strand" and "passenger strand" are used interchangeably herein.

The term "duplex" includes a region of complementarity between two regions of two or more polynucleotides that comprise separate strands, such as a sense strand and an antisense strand, or between two regions of a single contiguous polynucleotide.

As used herein, "specifically hybridizable" and "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., a to t, a to u, c to g), or in any other manner that allows for the formation of stable duplexes. "Perfect complementarity" or 100% complementarity refers to the situation in which each nucleotide unit of one polynucleotide strand can hydrogen bond with each nucleotide unit of a second polynucleotide strand. Less than perfect complementarity refers to the situation in which some, but not all, nucleotide units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an RNAi agent against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a double-strained RNAi agent.

The phrase "first 5' terminal nucleotide" includes first 5' terminal antisense nucleotides and first 5' terminal antisense nucleotides. "First 5' terminal antisense nucleotide" refers to the nucleotide of the antisense strand that is located at the 5' most position of that strand with respect to the bases of the antisense strand that have corresponding complementary bases on the sense strand. Thus, in a double stranded polynucleotide that is made of two separate strands, it refers to the 5' most base other than bases that are part of any 5' overhang on the antisense strand. When the first 5' terminal antisense nucleotide is part of a hairpin molecule, the term "terminal" refers to the 5' most relative position within the antisense region and thus is the 5" most nucleotide of the antisense region. The phrase "first 5' terminal sense nucleotide" is defined in reference to the sense nucleotide. In molecules comprising two separate strands, it refers to the nucleotide of the sense strand that is located at the 5' most position of that strand with respect to the bases of the sense strand that have corresponding complementary bases on the antisense strand. Thus, in a double stranded polynucleotide that is made of two separate strands, it is the 5' most base other than bases that are part of any 5' overhang on the sense strand.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, In one embodiment, the siRNA compound specifically discriminates a single-nucleotide difference. In this case, the siRNA compound only mediates RNAi if exact complementary is found in the region (e.g., within 7 nucleotides of) the single-nucleotide difference.

In one embodiment, oligonucleotides of the invention are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In one embodiment, nucleosides having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the Pv state using known methods to yield, in preferred embodiments, phosphodiester or phosphorothioate internucleotide linkages.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyl eneimino, and neutral non-ionic internucleoside linking groups such as amide-3 (3'-CH$_2$—C(=O)—N(H)-5'), amide-4 (3'-CH$_2$—N(H)—C(=O)-5').

As used herein the term "alternating motif" refers to a an oligonucleotide comprising a contiguous sequence of linked monomer subunits wherein the monomer subunits have two different types of sugar groups that alternate for essentially the entire sequence of the oligonucleotide. Oligonucleotides having an alternating motif can be described by the formula: 5'-A(-L-B-L-A)n(-L-B)nn-3' where A and B are monomelic subunits that have different sugar groups, each L is an internucleoside linking group, n is from about 4 to about 12 and nn is 0 or 1. This permits alternating oligonucleotides from about 9 to about 26 monomer subunits in length. This length range is not meant to be limiting as longer and shorter oligonucleotides are also amenable to the present invention. In one embodiment, one of A and B is a 2'-modified nucleoside as provided herein.

As used herein the term "uniformly fully modified motif" refers to an oligonucleotide comprising a contiguous sequence of linked monomer subunits that each have the same type of sugar group. In one embodiment, the uniformly fully modified motif includes a contiguous sequence of nucleosides of the invention. In one embodiment, one or both of the 3' and 5'-ends of the contiguous sequence of the nucleosides provided herein, comprise terminal groups such as one or more unmodified nucleosides.

As used herein the term "hemimer motif" refers to an oligonucleotide having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomelic subunits) having uniform but different sugar groups and located on either the 3' or the 5' end of the oligomeric compound. In one embodiment, the hemimer motif comprises a contiguous sequence of from about 10 to about 28 monomer subunits of one type with from 1 to 5 or from 2 to about 5 monomer subunits of a second type located at one of the termini. In one embodiment, a hemimer is a contiguous sequence of from about 8 to about 20 β-D-2'-deoxyribonucleosides having from 1-12 contiguous nucleosides of the invention located at one of the termini. In one embodiment, a hemimer is a contiguous sequence of from about 8 to about 20 β-D-2'-deoxyribonucleosides having from 1-5 contiguous nucleosides of the invention located at one of the termini. In one embodiment, a hemimer is a contiguous sequence of from about 12 to about 18 β-D-2'-deoxyribo-nucleosides having from 1-3 contiguous nucleosides of the invention located at one of the termini. In one embodiment, a hemimer is a contiguous sequence of from about 10 to about 14 β-D-2'-deoxyribonucleosides having from 1-3 contiguous nucleosides of the invention located at one of the termini.

As used herein the term "blockmer motif" refers to an oligonucleotide comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In one embodiment, blockmer oligonucleotides are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In one embodiment, each of the two or more regions have the same type of sugar group. In one embodiment, each of the two or more regions have a different type of sugar group. In one embodiment, positionally modified oligonucleotides are provided comprising a sequence of from 8 to 20 β-D-2'-deoxyribonucleosides that further includes two or three regions of from 2 to about 5 contiguous nucleosides of the invention. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In one embodiment, the external regions are small (each independently 1, 2, 3, 4 or about 5 monomer subunits) and the monomer subunits comprise non-naturally occurring sugar groups with the internal region comprising β-D-2'-deoxyribonucleosides. In one embodiment, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribo-nucleosides but can comprise non-naturally occurring sugar groups.

In one embodiment, the gapped oligonucleotides comprise an internal region of β-D-2'-deoxyribonucleosides with one of the external regions comprising nucleosides of the invention. In one embodiment, the gapped oligonucleotide comprise an internal region of β-D-2'-deoxyribonucleosides with both of the external regions comprising nucleosides of the invention. In one embodiment, the gapped oligonucleotide comprise an internal region of β-D-2'-deoxyribonucleosides with both of the external regions comprising nucleosides of the invention. In one embodiment, gapped oligonucleotides are provided herein wherein all of the monomer subunits comprise non-naturally occurring sugar groups. In one embodiment, gapped oliogonucleotides are provided comprising one or two nucleosides of the invention at the 5'-end, two or three nucleosides of the invention at the 3'-end and an internal region of from 10 to 16 β-D-2'-deoxyribonucleosides. In one embodiment, gapped oligonucleotides are provided comprising one nucleoside of the invention at the 5'-end, two nucleosides of the invention at the 3'-end and an internal region of from 10 to 16 β-D-2'-deoxyribonucleosides. In one embodiment, gapped oligonucleotides are provided comprising two nucleosides of the invention at the 5'-end, two nucleosides of the invention at the 3'-end and an internal region of from 10 to 14 β-D-2'-deoxyribonucleosides. In one embodiment, gapped oligonucleotides are provided that are from about 10 to about 21 monomer subunits in length. In one embodiment, gapped oligonucleotides are provided that are from about 12 to about 16 monomer subunits in length. In one embodiment, gapped oligonucleotides are provided that are from about 12 to about 14 monomer subunits in length.

The phrase "pharmaceutically acceptable carrier or diluent" includes compositions that facilitate the introduction of nucleic acid therapeutics such as siRNA, dsRNA, dsDNA, shRNA, microRNA, antimicroRNA, antagomir, antimir, antisense, aptamer or dsRNA/DNA hybrids into a cell and includes but is not limited to solvents or dispersants, coatings, anti-infective agents, isotonic agents, and agents that mediate absorption time or release of the inventive polynucleotides and double stranded polynucleotides. The phrase "pharmaceutically acceptable" includes approval by a regulatory agency of a government, for example, the U.S. federal government, a non-U.S. government, or a U.S. state government, or inclusion in a listing in the U.S. Pharmacopeia or any other generally recognized pharmacopeia for use in animals, including in humans.

The terms "silence" and "inhibit the expression of" and related terms and phrases, refer to the at least partial suppression of the expression of a gene targeted by an siRNA or siNA, as manifested by a reduction of the amount of mRNA transcribed from the target gene which may be isolated from a first cell or group of cells in which the target gene is transcribed and which has or have been treated such that the expression of the target gene is inhibited, as compared to a second cell or group of cells substantially identical to the first cell or group of cells but which has or have not been so treated (i.e., control cells).

The term "halo" or "halogen" refers to any radical of fluorine, chlorine, bromine or iodine.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as (Ci-C6)alkanoyl (e.g., formyl, acetyl, propionyl, butyryl, valeryl, caproyl, t-butylacetyl, etc.), (C3-Ce)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" or "heterocyclic" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, aryl, heterocyclyl, or heteroaryl group at any atom of that group. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, ureido or conjugate groups.

In one embodiment, the substituents include $OR_{11}$, $COR_{11}$, $CO_2R_{11}$,

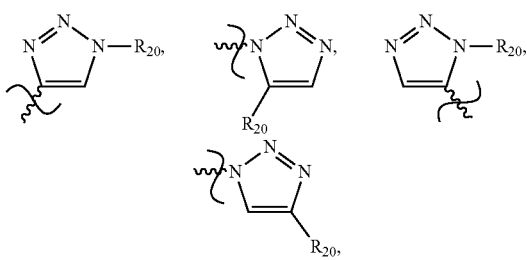

$NR_{21}R_{31}$, $CONR_{21}R_{31}$, $CON(H)NR_{21}R_{31}$, $ONR_{21}R_{31}$, $CON(H)N=CR_{41}R_{51}$, $N(R_{21})C(NR_{31})NR_{21}R_{31}$, $N(R_{21})C(O)NR_{21}R_{31}$, $N(R_{21})C(S)NR_{21}R_{31}$, $OC(O)NR_{21}R_{31}$, $SC(O)NR_{21}R_{31}$, $N(R_{21})C(S)OR_{11}$, $N(R_{21})C(O)OR_{11}$, $N(R_{21})C(O)SR_{11}$, $N(R_{21})N=CR_{41}R_{51}$, $ON=CR_{41}R_{51}$, $SO_2R_{11}$, $SOR_{11}$, $SR_{11}$, and substituted or unsubstituted heterocyclic;

$R_{21}$ and $R_{31}$ for each occurrence are independently hydrogen, acyl, unsubstituted or substituted aliphatic, aryl, heteroaryl, heterocyclic, $OR_{11}$, $COR_{11}$, $CO_2R_{11}$, or $NR_{11}R_{11}'$; or $R_{21}$ and $R_{31}$, taken together with the atoms to which they are attached, firm a heterocyclic ring;

$R_{41}$ and $R_{51}$ for each occurrence are independently hydrogen, acyl, unsubstituted or substituted aliphatic, aryl, heteroaryl, heterocyclic, $OR_{11}$, $COR_{11}$, $CO_2R_{11}$, or $NR_{11}R_{11}'$; and $R_{11}$ and $R_{11}'$ are independently hydrogen, aliphatic, substituted aliphatic, aryl, heteroaryl, or heterocyclic. In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron* 1992, 48, 2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.* 1994, 35, 7821; Verhart and Tesser, *Rec. Trav. Chim. Pays-Bas* 1987, 107, 621).

Additional amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Evaluation of Candidate RNAs

One can evaluate a candidate RNA agent, e.g., a modified RNA, for a selected property by exposing the agent or modified molecule and a control molecule to the appropriate conditions and evaluating for the presence of the selected property. For example, resistance to a degradent can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dssiRNA compounds.

In an alternative functional assay, a candidate dssiRNA compound homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dssiRNA compound would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added.

Kits

In certain other aspects, the invention provides kits that include a suitable container containing a pharmaceutical formulation of an RNAi agent. In one embodiment the individual components of the pharmaceutical formulation may be provided in one container. Alternatively, it may be desirable to provide the components of the pharmaceutical formulation separately in two or more containers, e.g., one container for an RNAi agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

SYNTHETIC METHODS AND EXAMPLES

The compounds of the inventions may be prepared by any process known to be applicable to the preparation of chemically-related compounds. Suitable processes for making certain intermediates include, for example, those references listed below which are herein incorporated by reference. Necessary starting materials may be obtained by standard procedures of organic chemistry. Alternatively necessary starting materials are obtainable by analogous procedures to those illustrated which are within the ordinary skill of a chemist. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

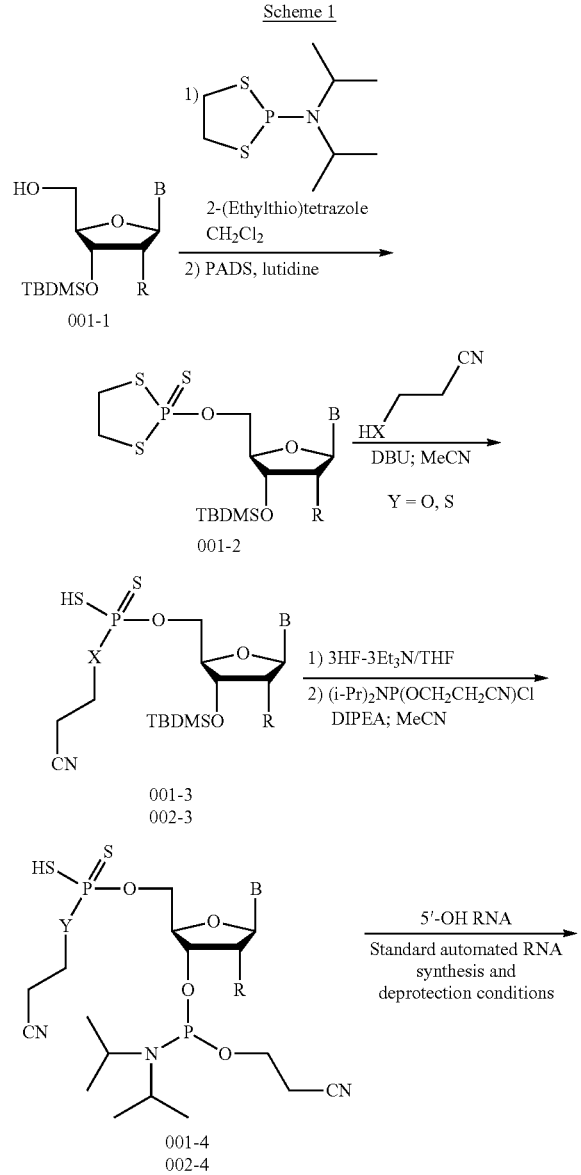

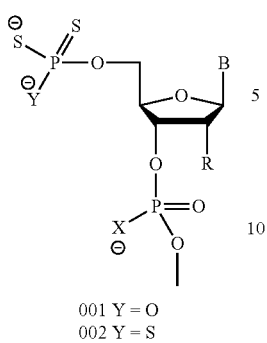
001 Y = O
002 Y = S
Scheme 1a
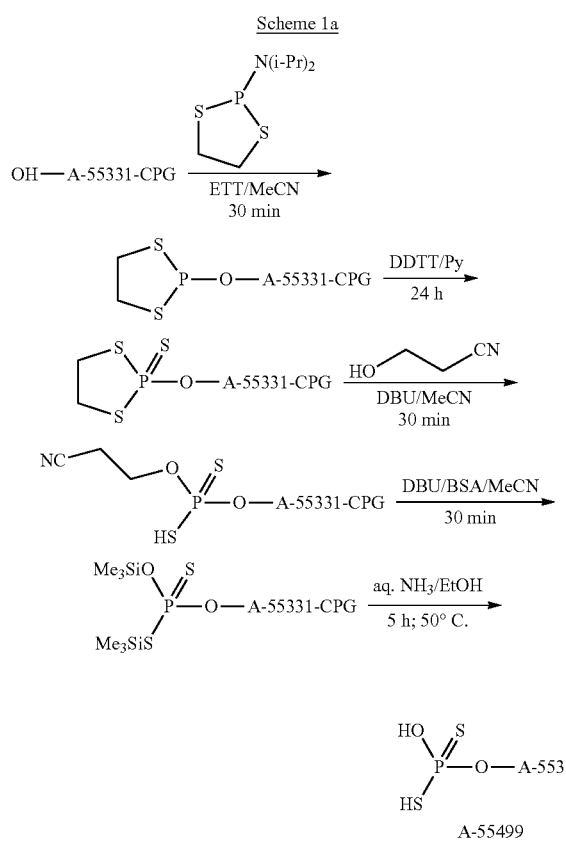
A-55499
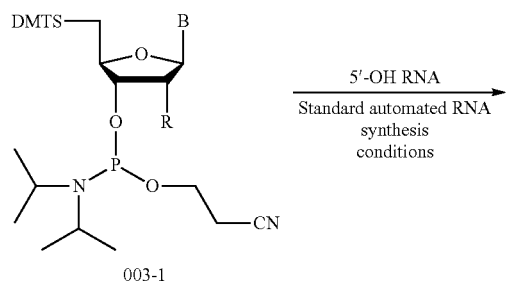
003-1
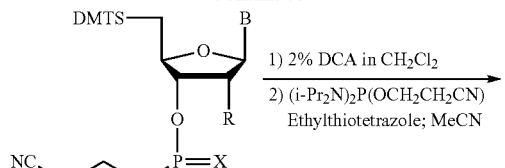
003-2
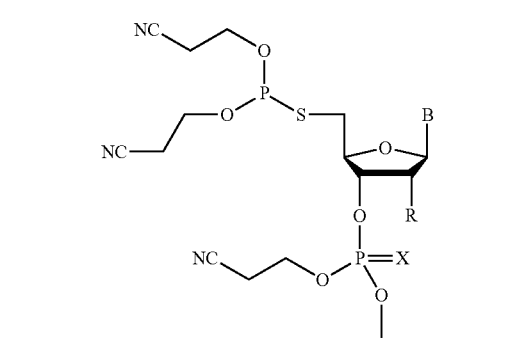
003-3
1) I$_2$/Py/water
2) Standard deprot. cond.
1) PADS/lutidine
2) Standard deprot. conditiond
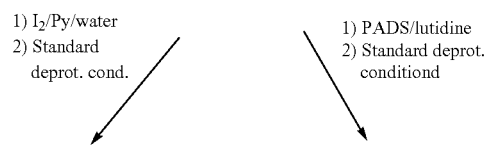
003          004
Ref.: J. Matulic-Adamic et al. Nucleosides & Nucleotides, 1997, 16, 1933-1950.
Scheme 3
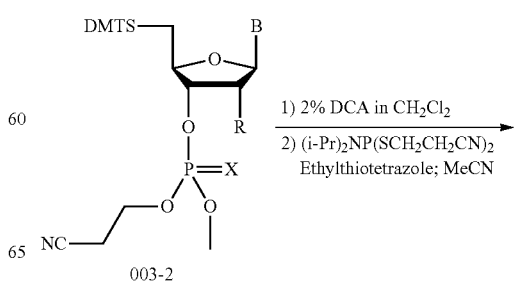
003-2

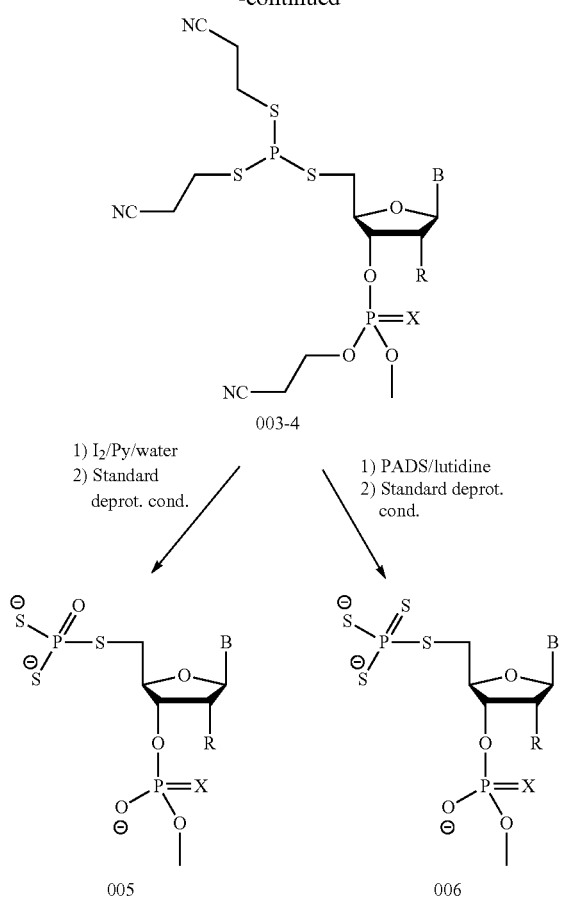
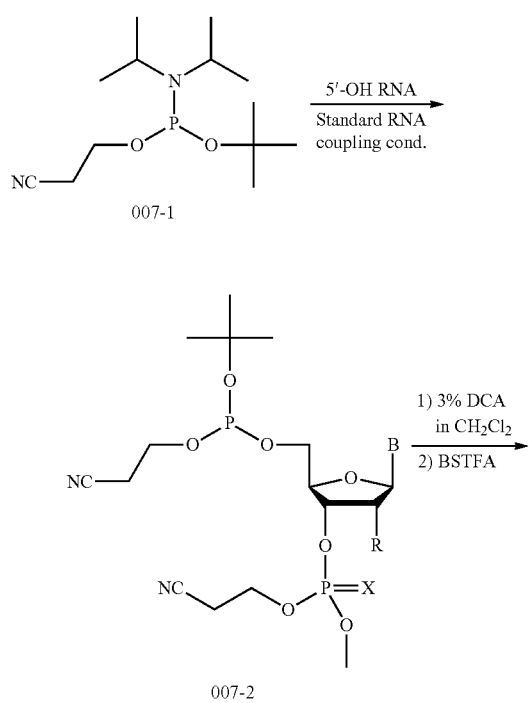
Scheme 4
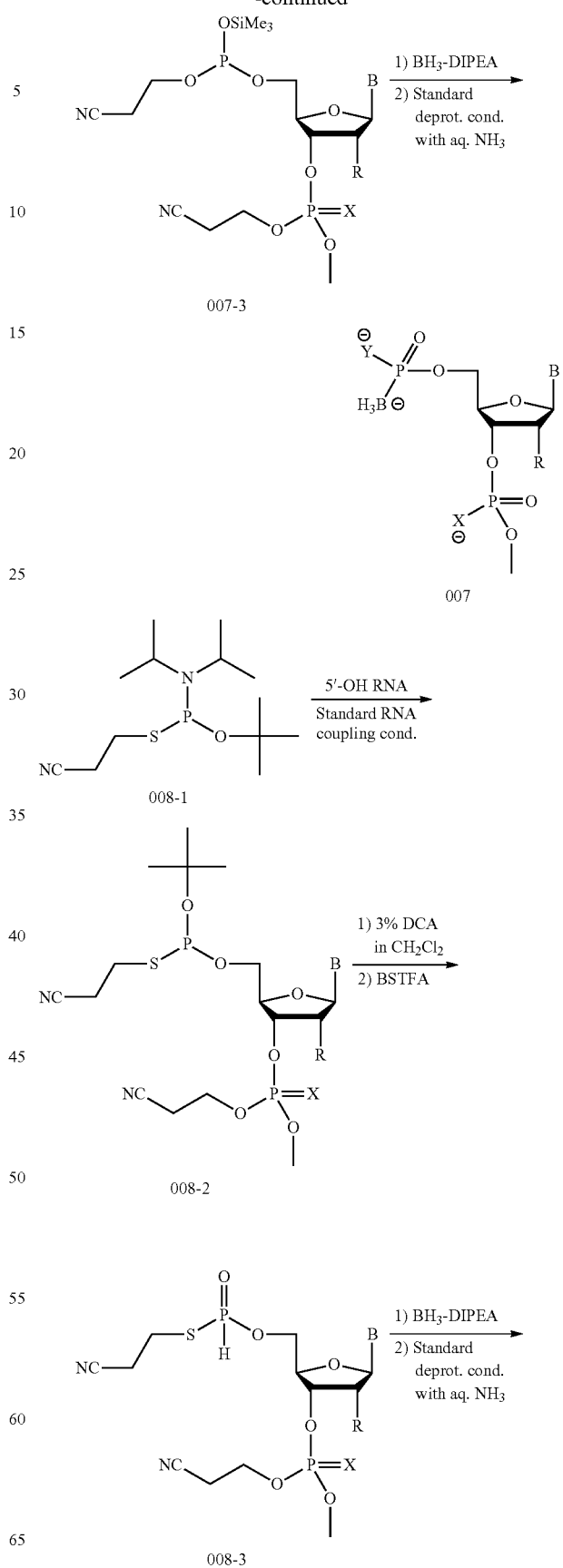

89
-continued
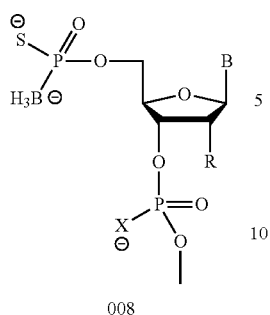
008
Ref.: A. Meyer et al. Tetrahedron Lett. 2006, 47, 8867-8871
90
-continued
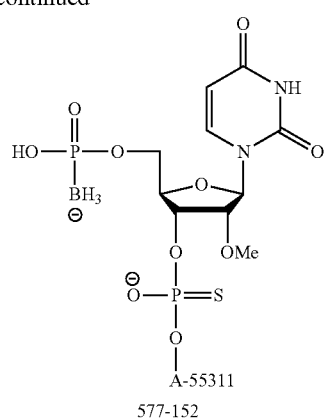
A-55311
577-152
Scheme 4a
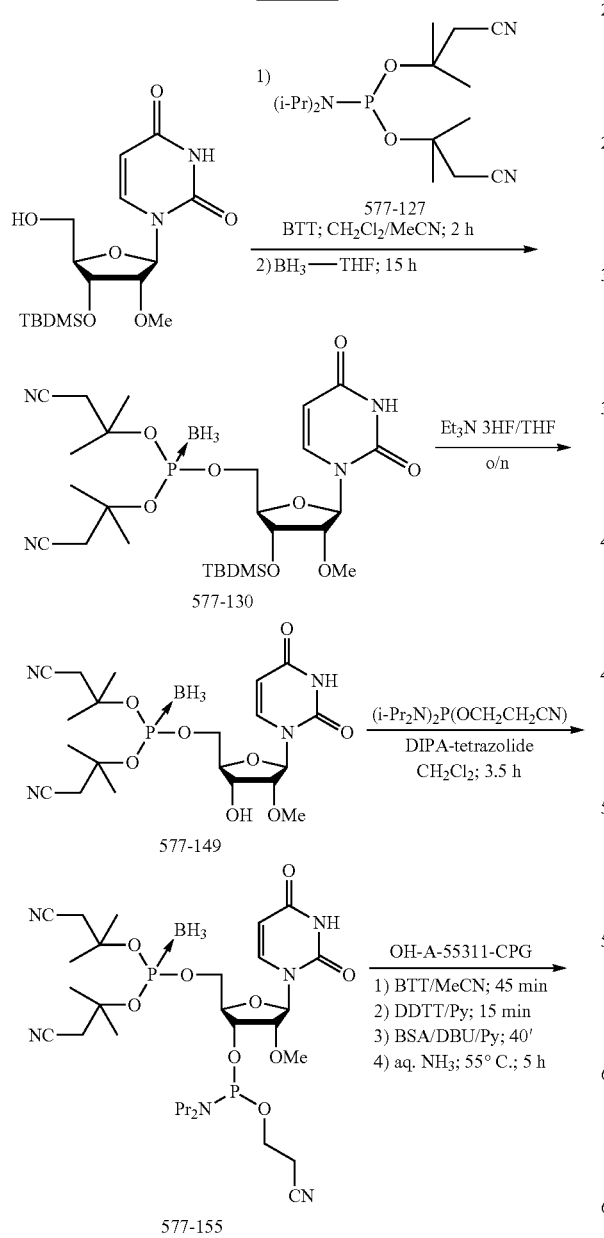
Scheme 5
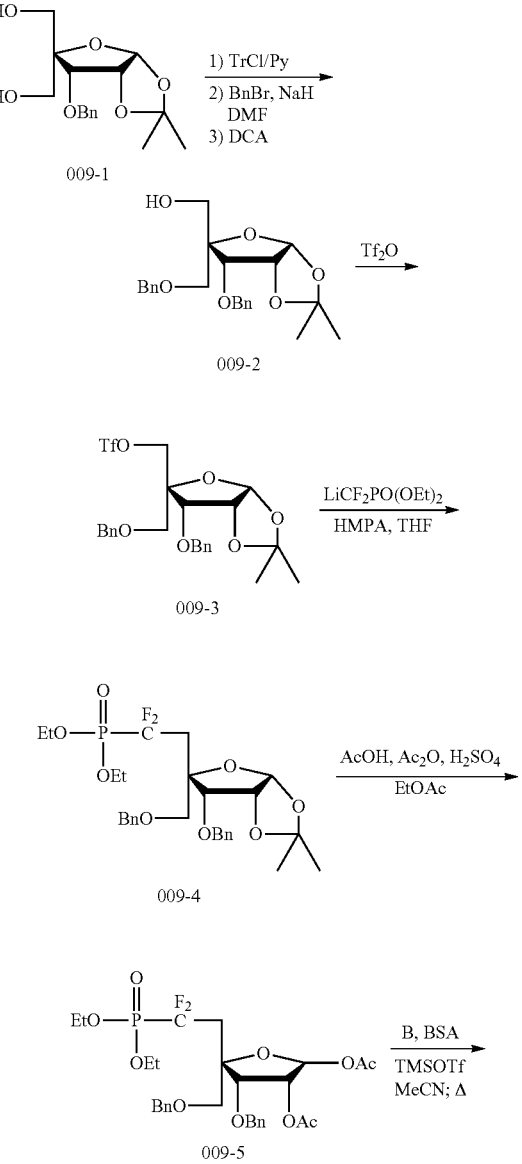

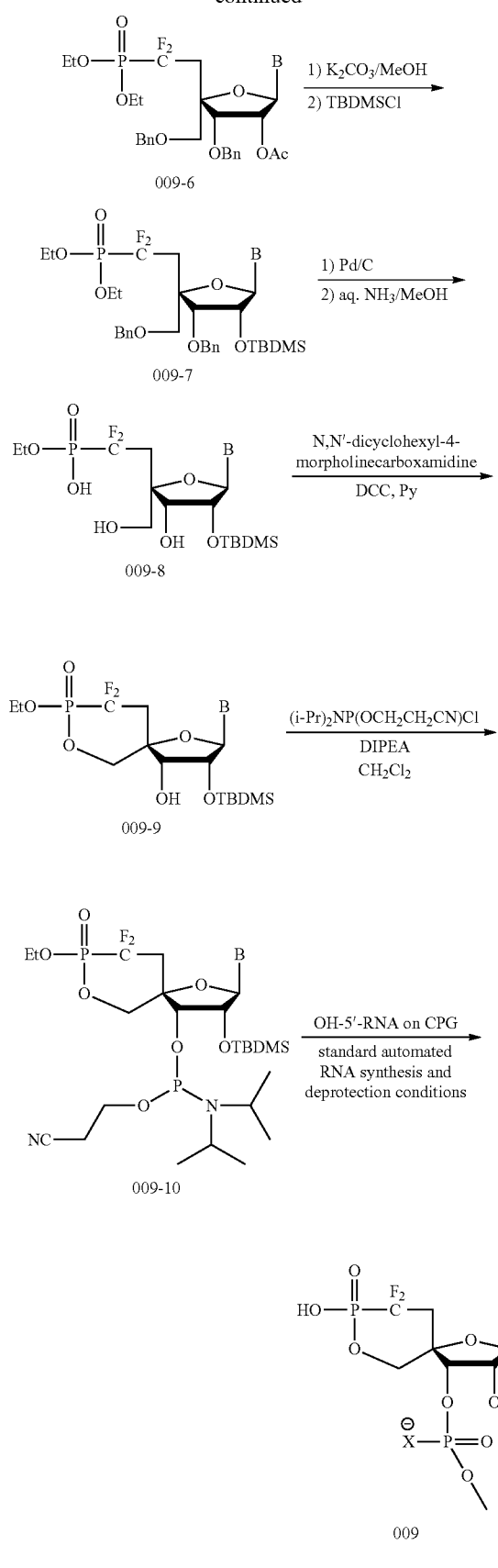
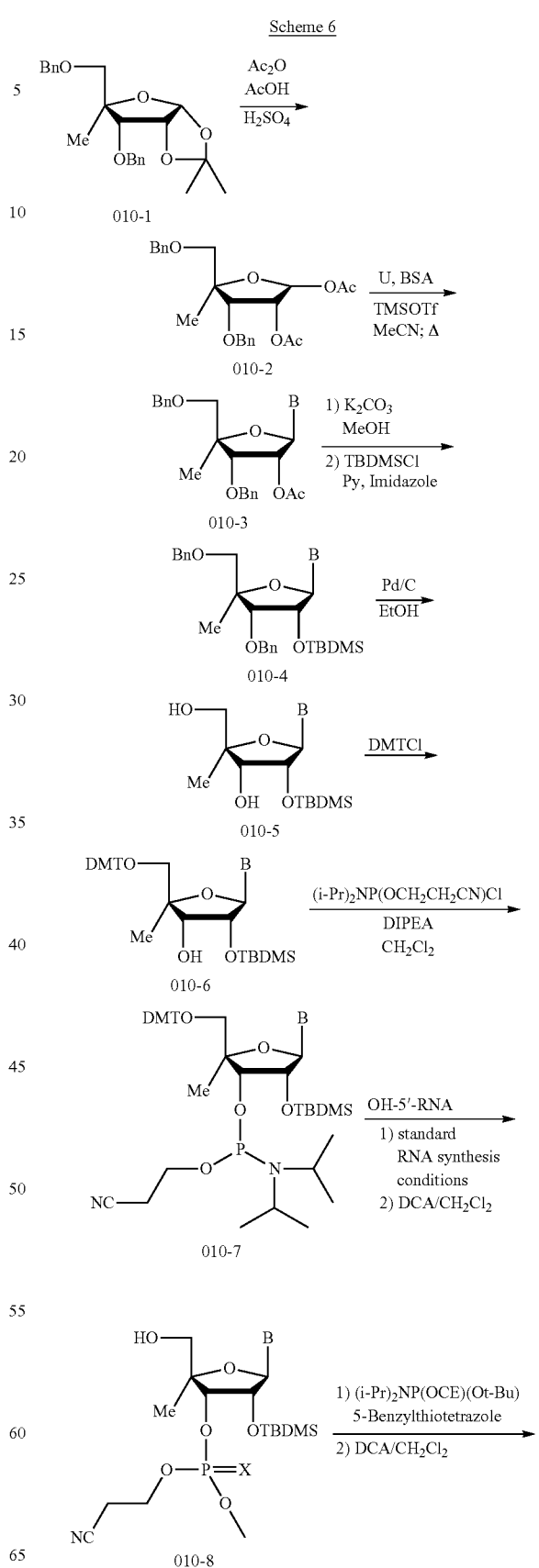
Scheme 6

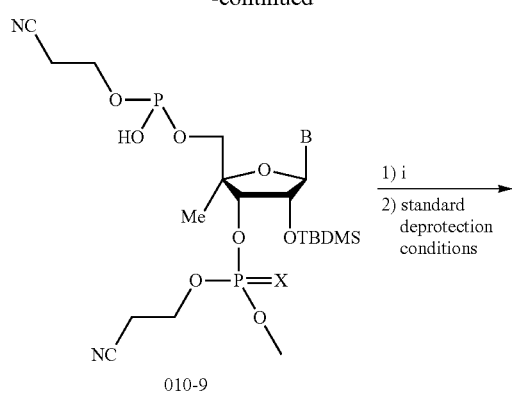
010-9
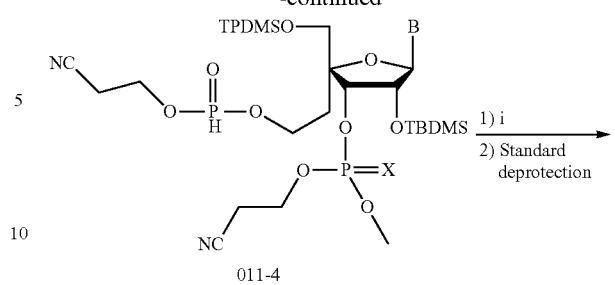
011-4
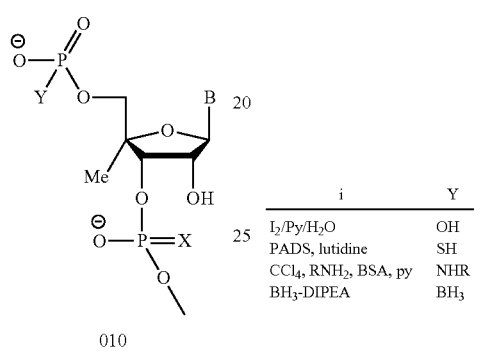
010
| i | Y |
|---|---|
| I$_2$/Py/H$_2$O | OH |
| PADS, lutidine | SH |
| CCl$_4$, RNH$_2$, BSA, py | NHR |
| BH$_3$-DIPEA | BH$_3$ |
011
| i | Y |
|---|---|
| I$_2$/Py/H$_2$O | OH |
| PADS, lutidine | SH |
| CCl$_4$, RNH$_2$, BSA, py | NHR |
Scheme 7
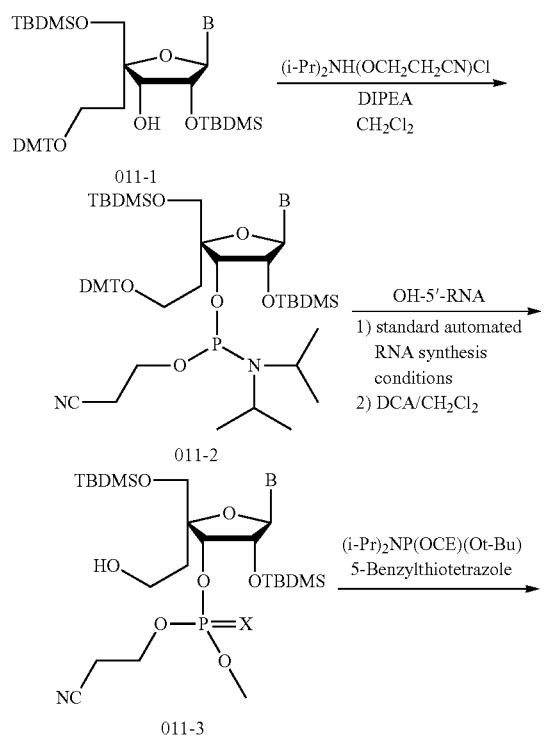
011-1
011-2
011-3
Scheme 8
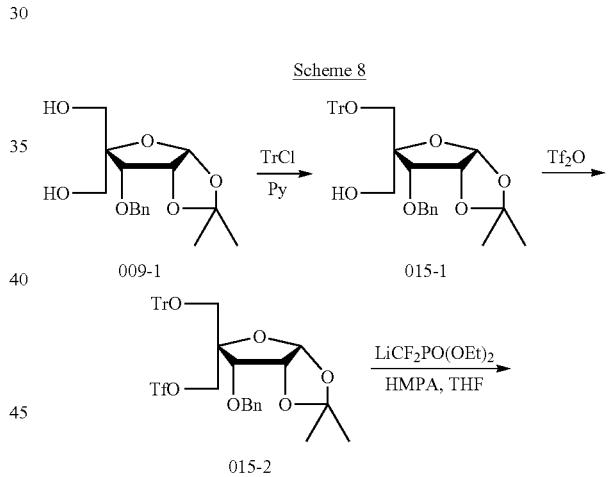
009-1
015-1
015-2
015-3
015-4

-continued
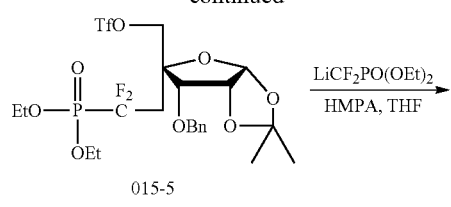
015-5
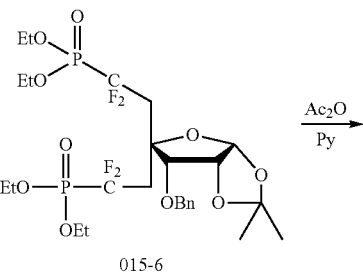
015-6
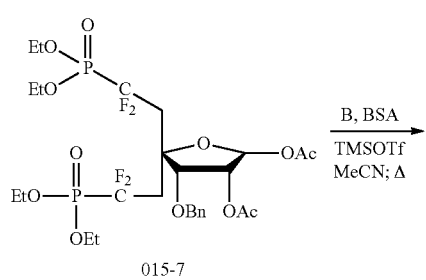
015-7
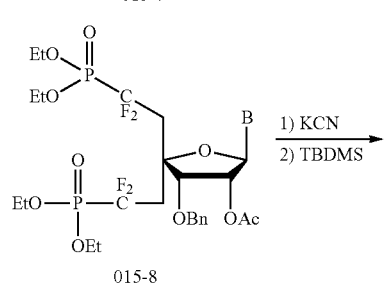
015-8
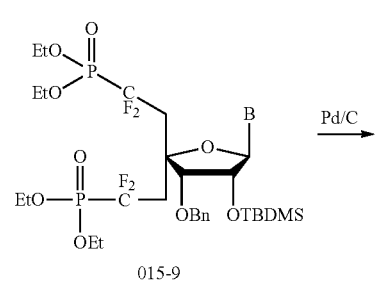
015-9
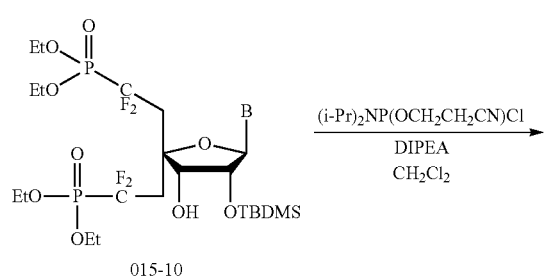
015-10
-continued
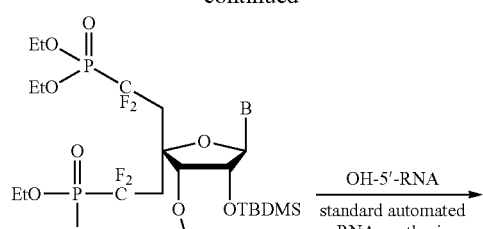
015-11
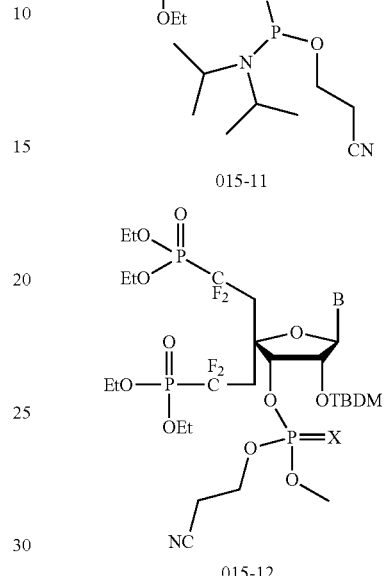
015-12
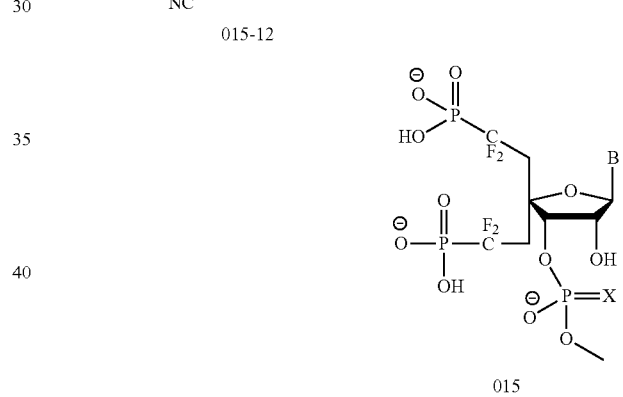
015
Scheme 9
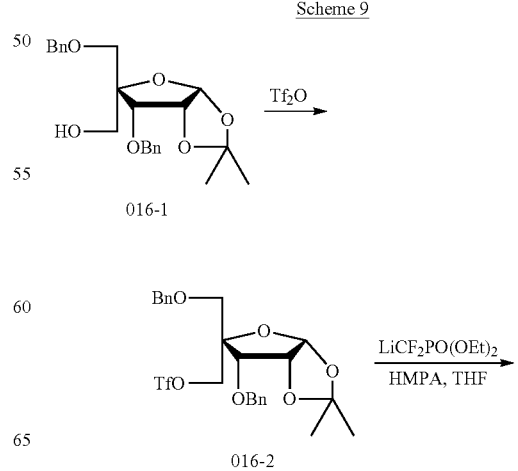
016-1
016-2

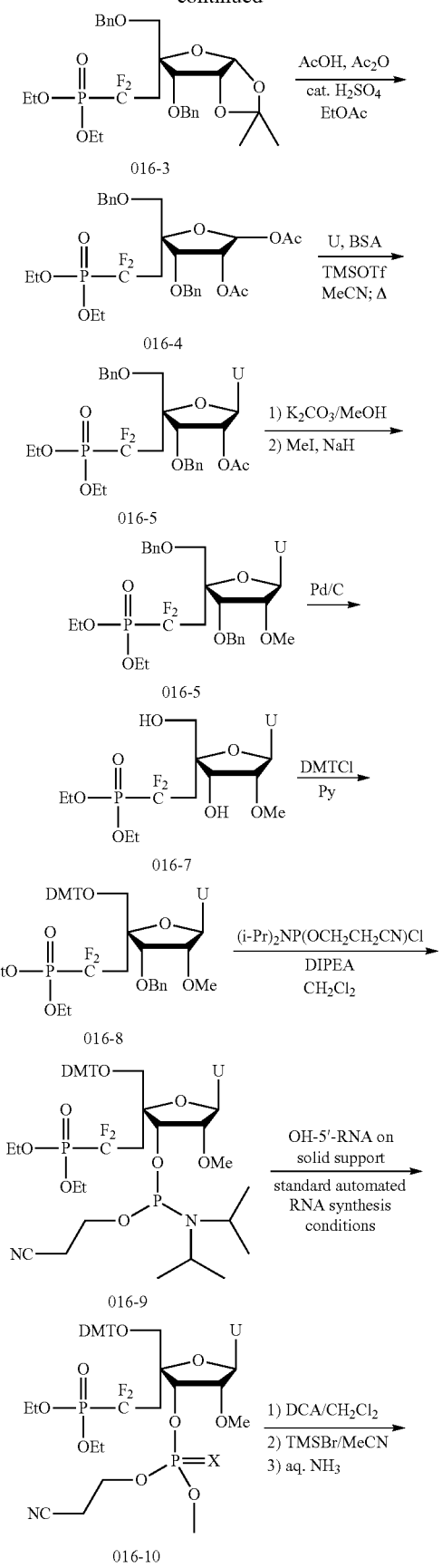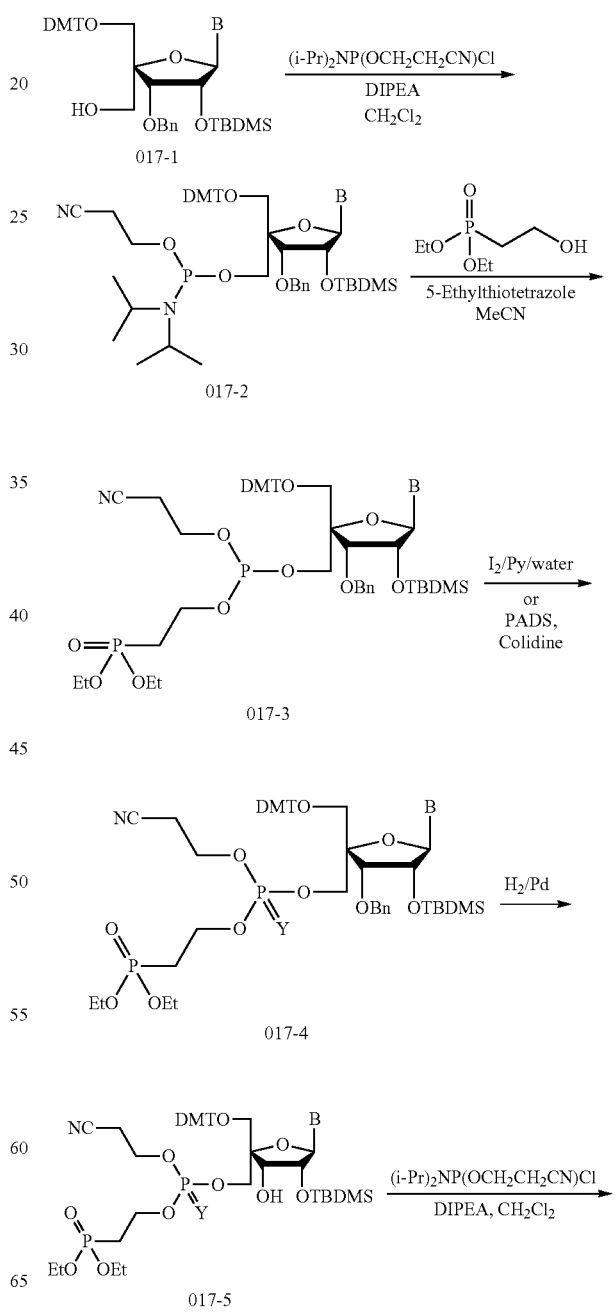

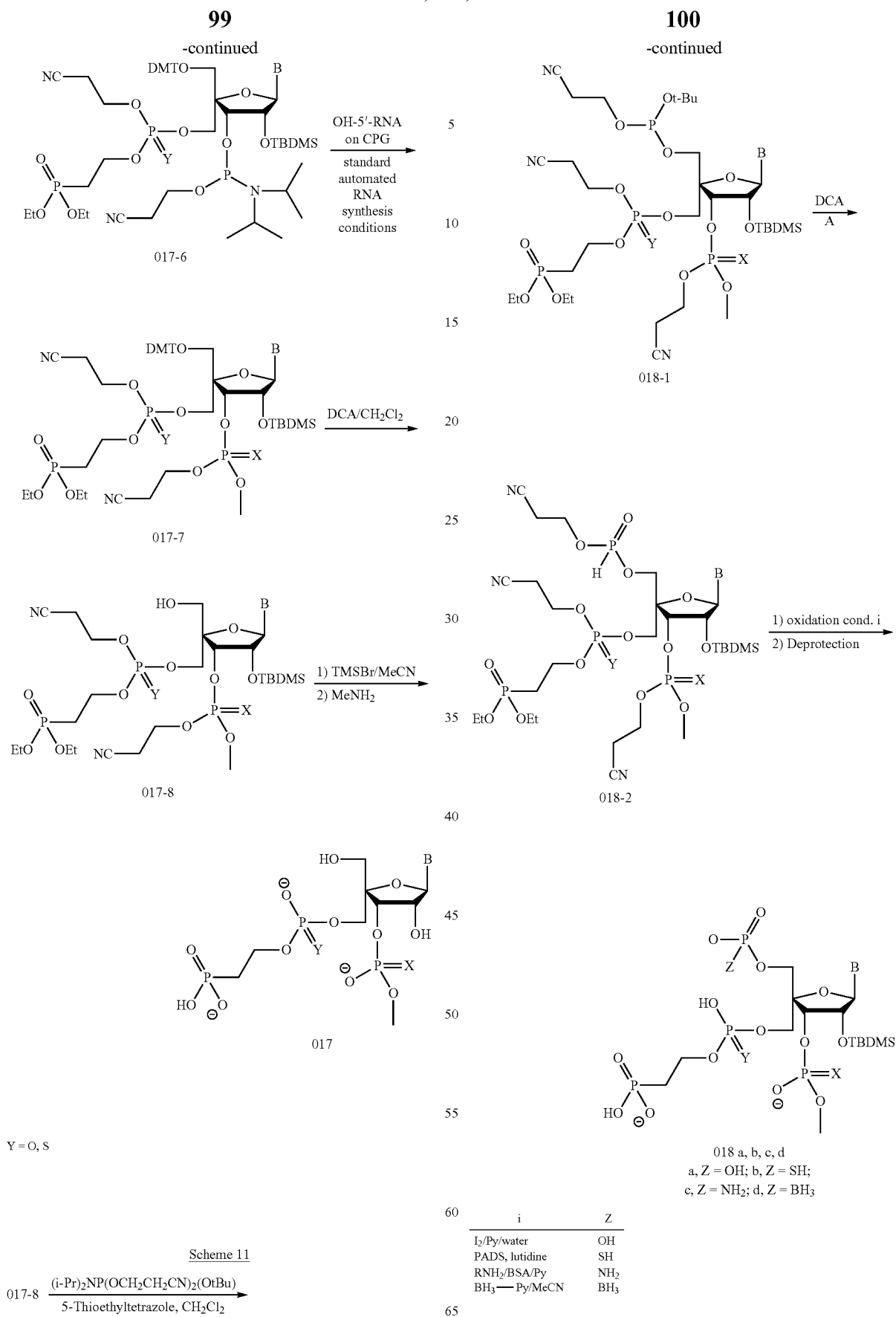

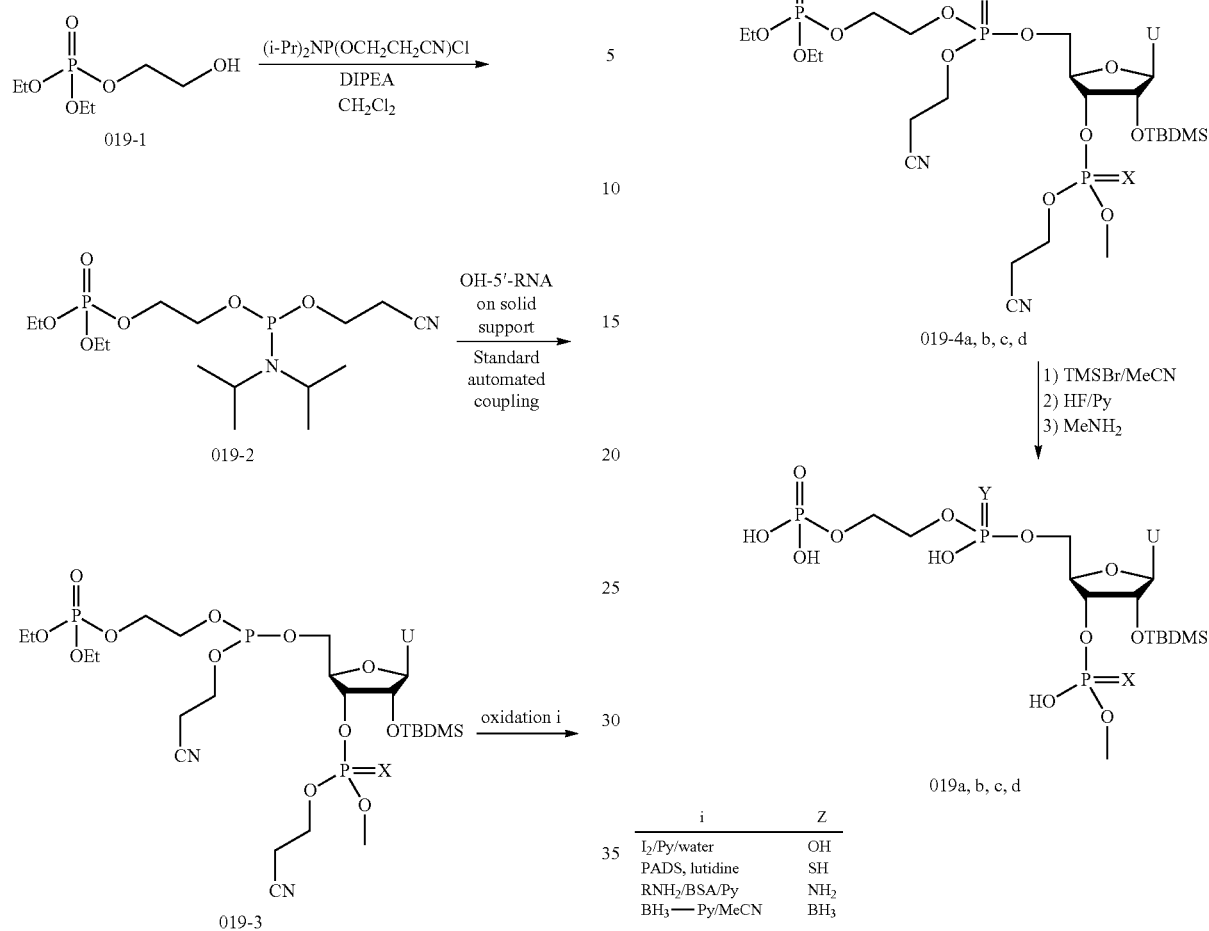
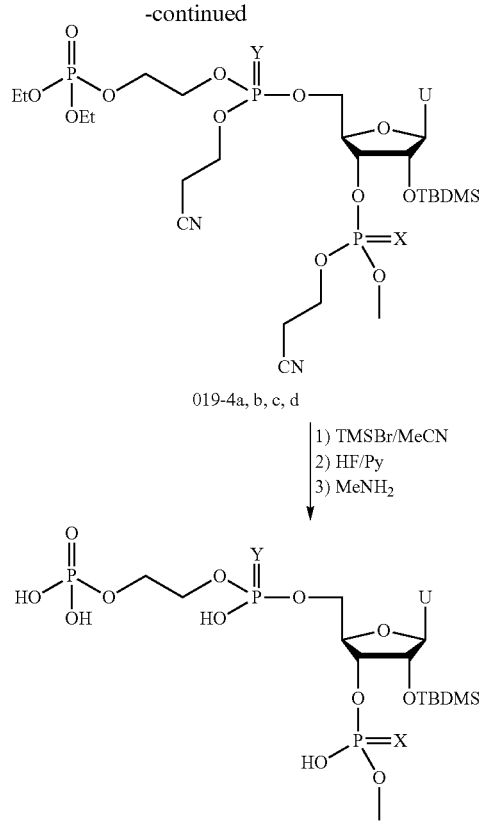
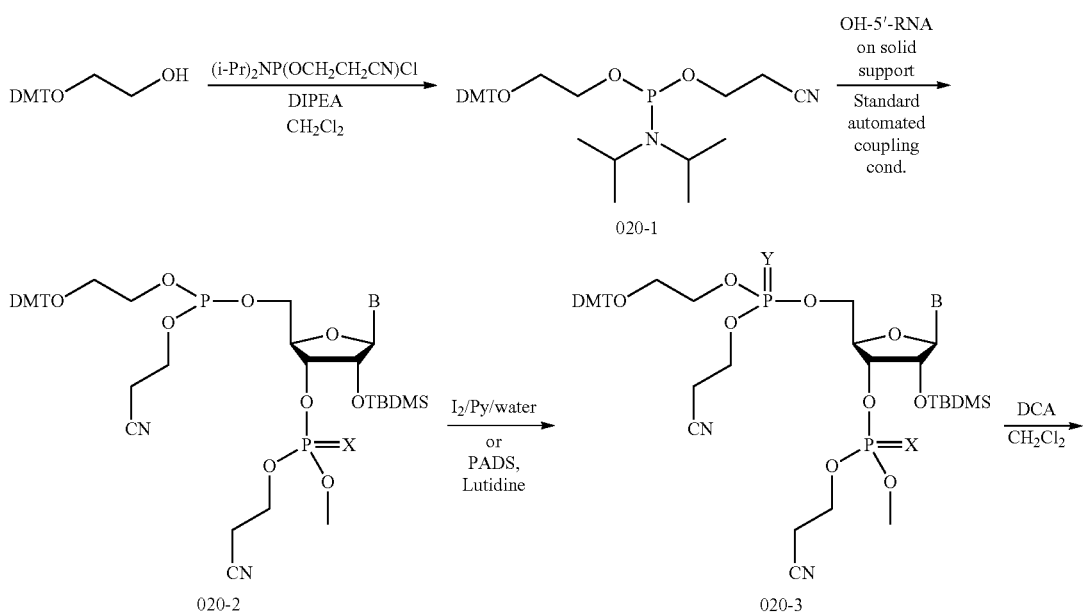

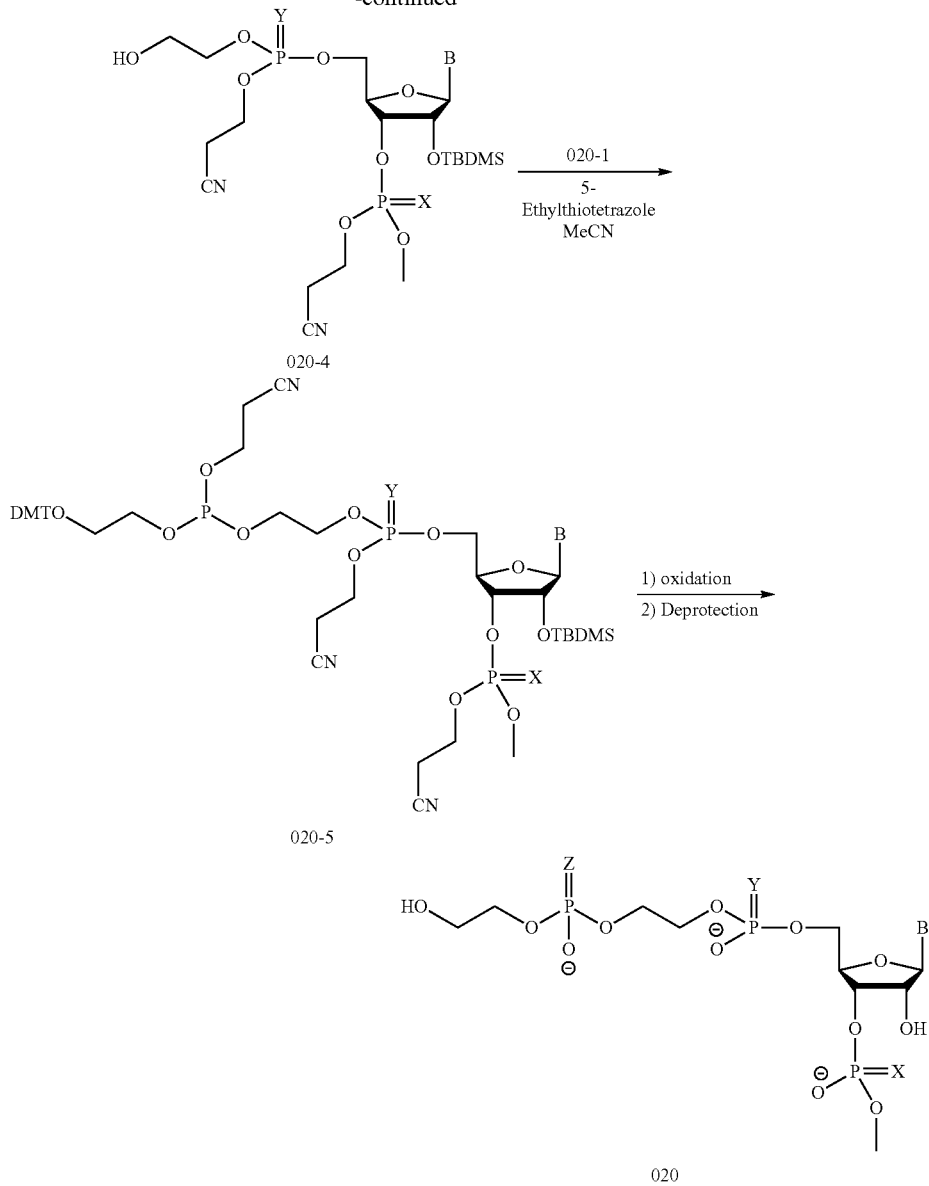
X = O, S
Y = O, S, BH₃, NH₂
Z = O, S, BH₃, NH₂
Scheme 12a
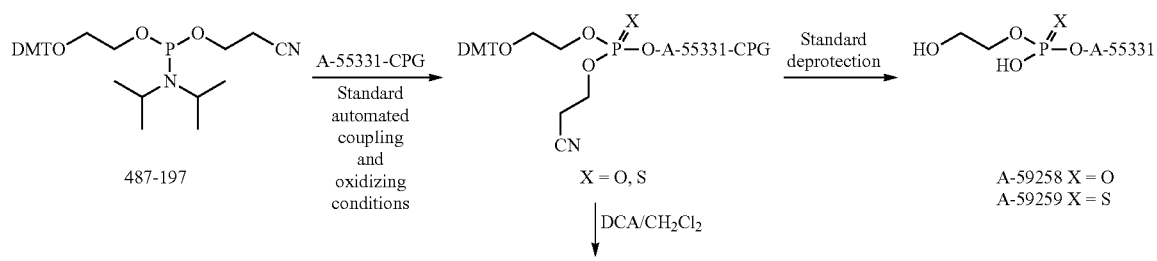

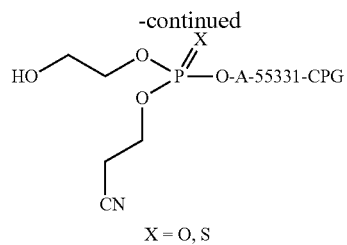
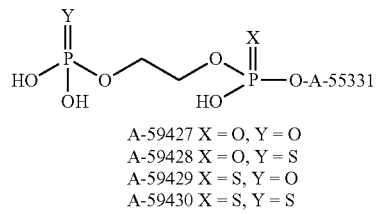
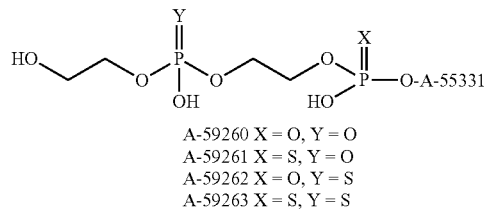
Scheme 14
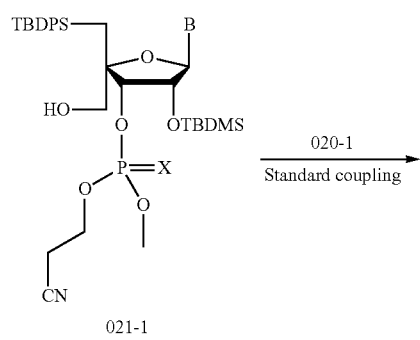
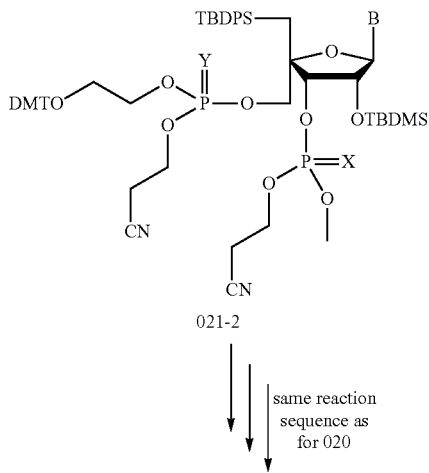
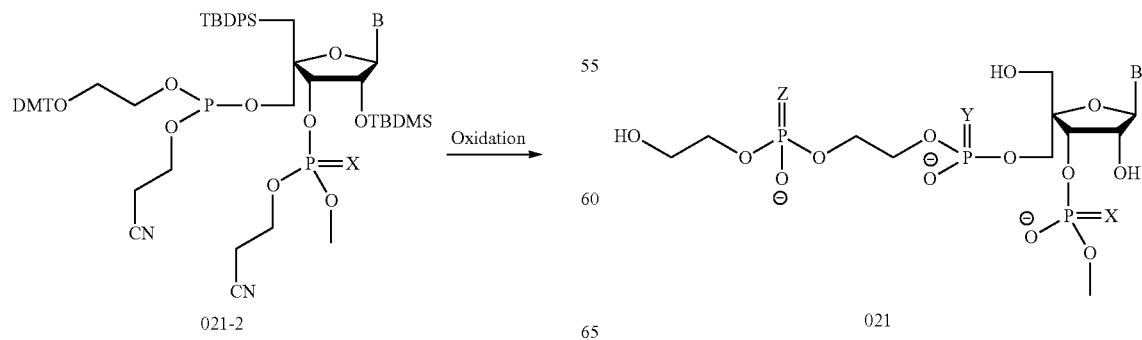

Scheme 15
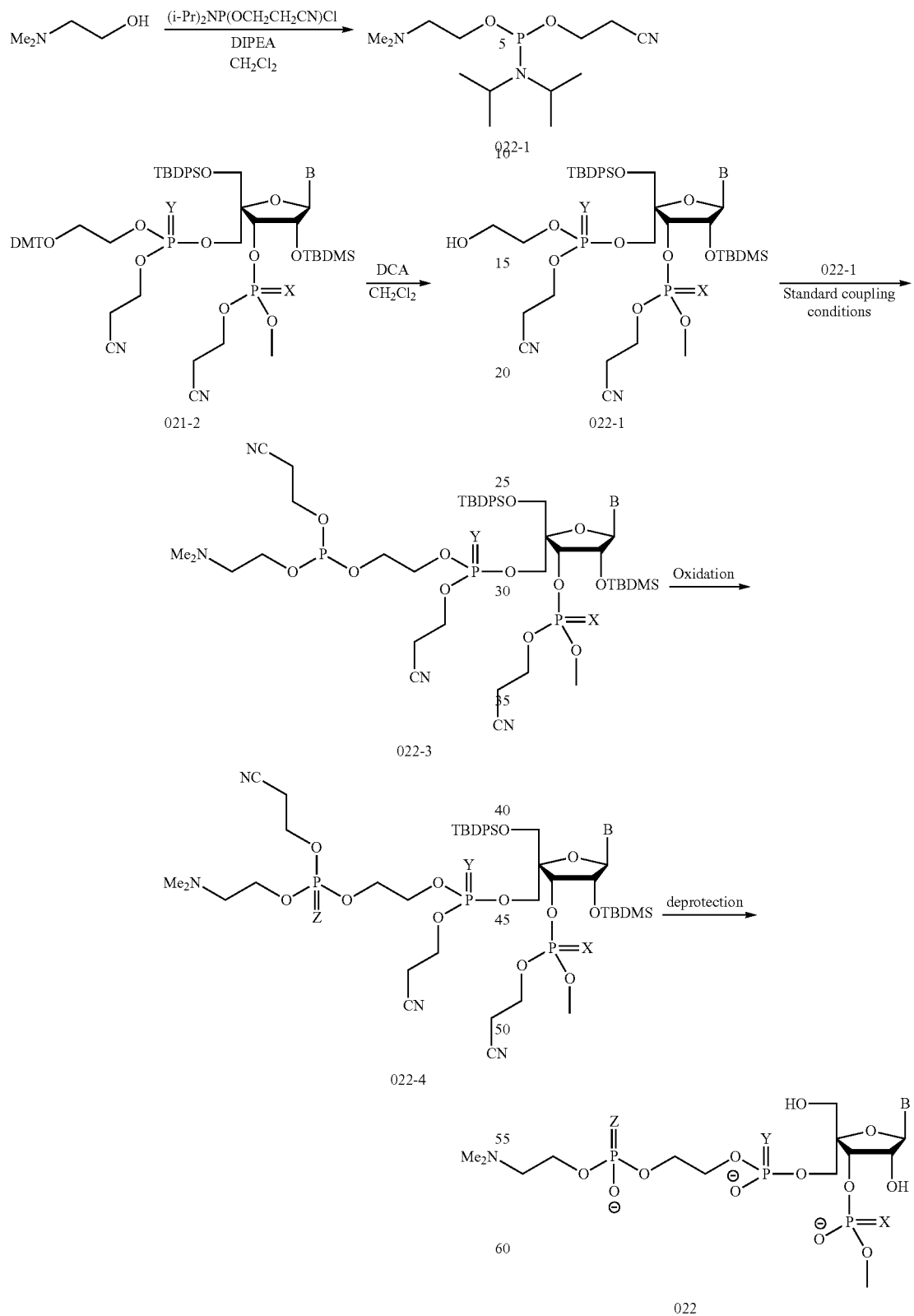
X = O, S
Y, Z = O, S, NH$_2$, BH$_3$

Scheme 16
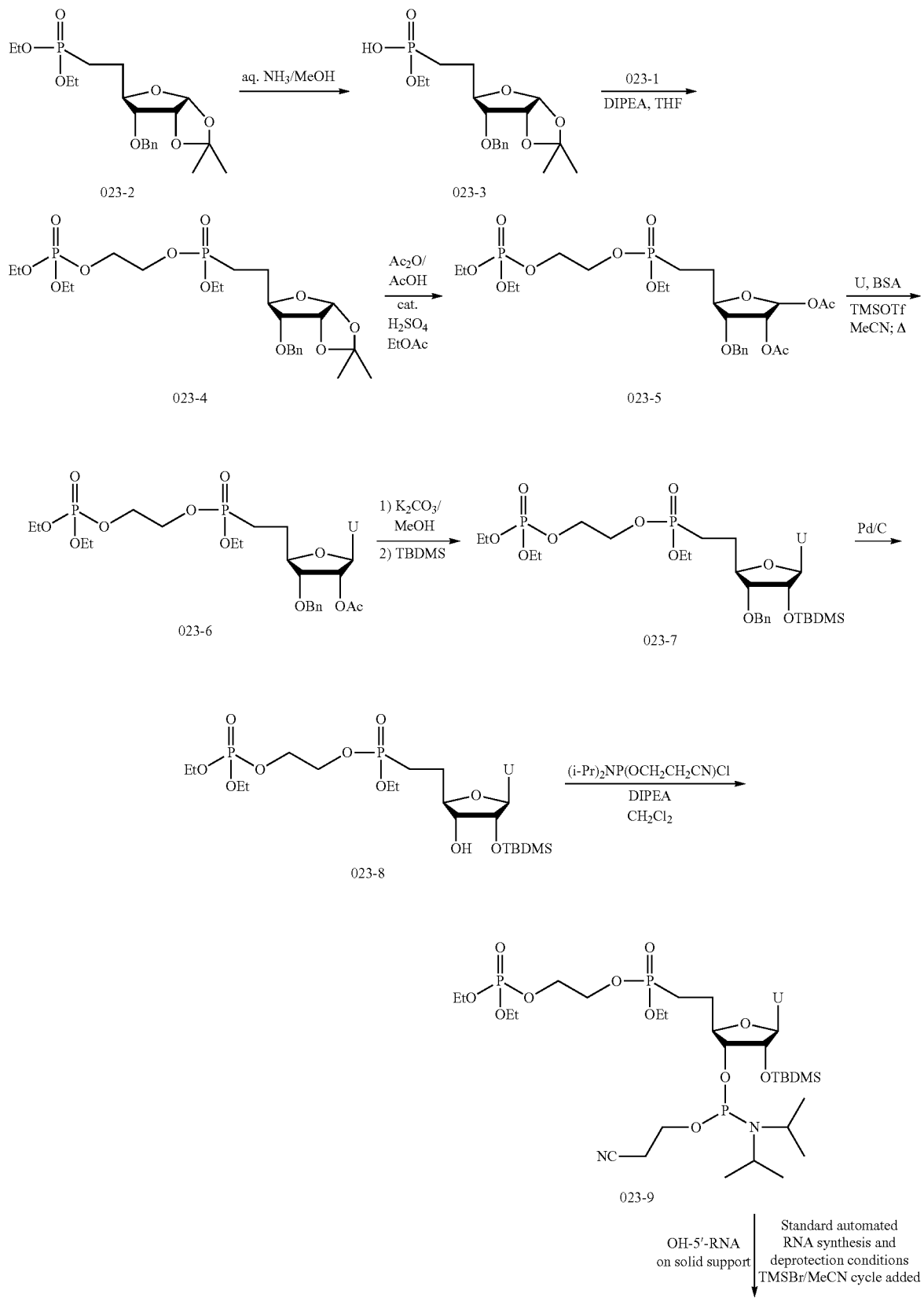

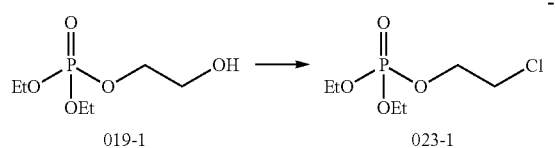
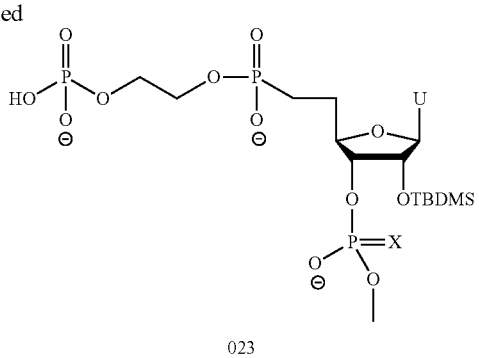
Ref.: Collect Czech. Chem. Commun. 1989, 54 (4), 1055-1066
Scheme 17
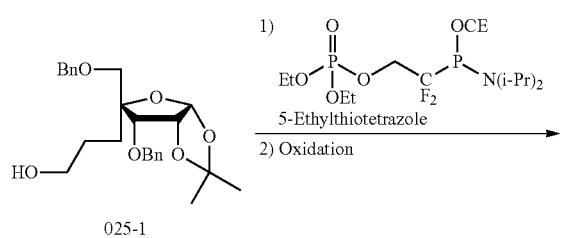
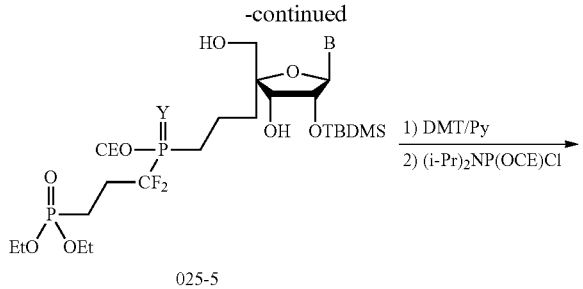
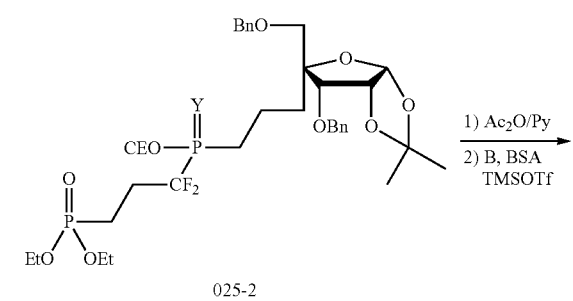
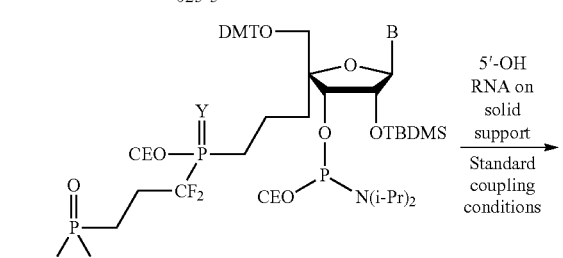
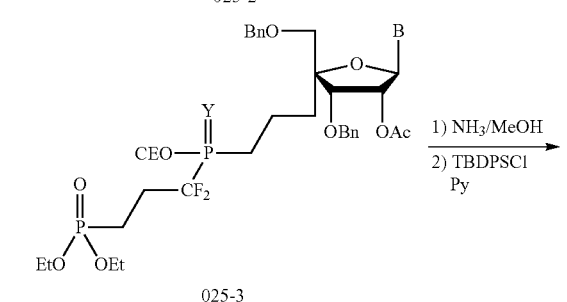
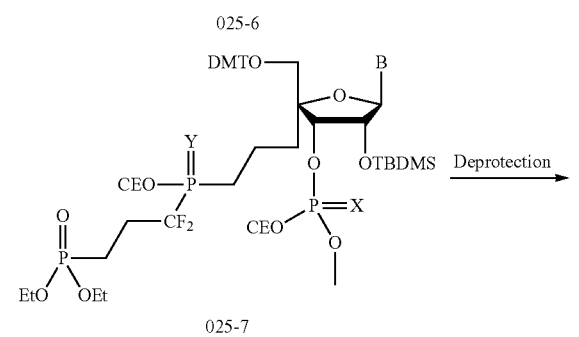
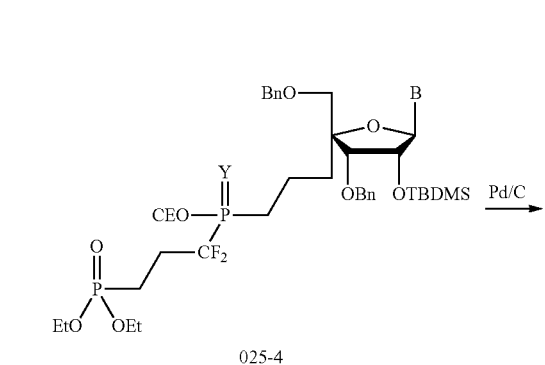
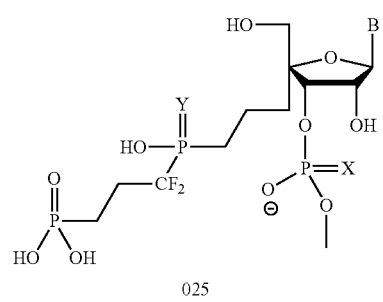
Ref.: K. Morita et al. *Bioorg. Med. Chem.* 2003, 11, 2211-2226

Scheme 18
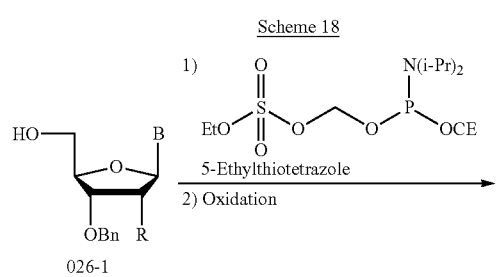
026-1
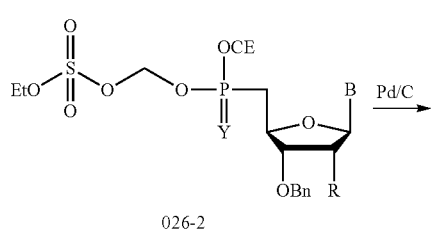
026-2
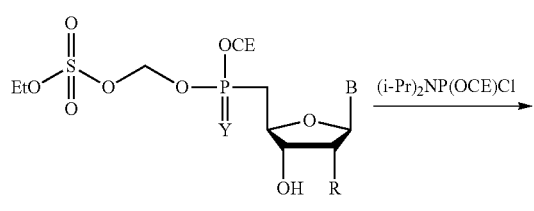
026-3
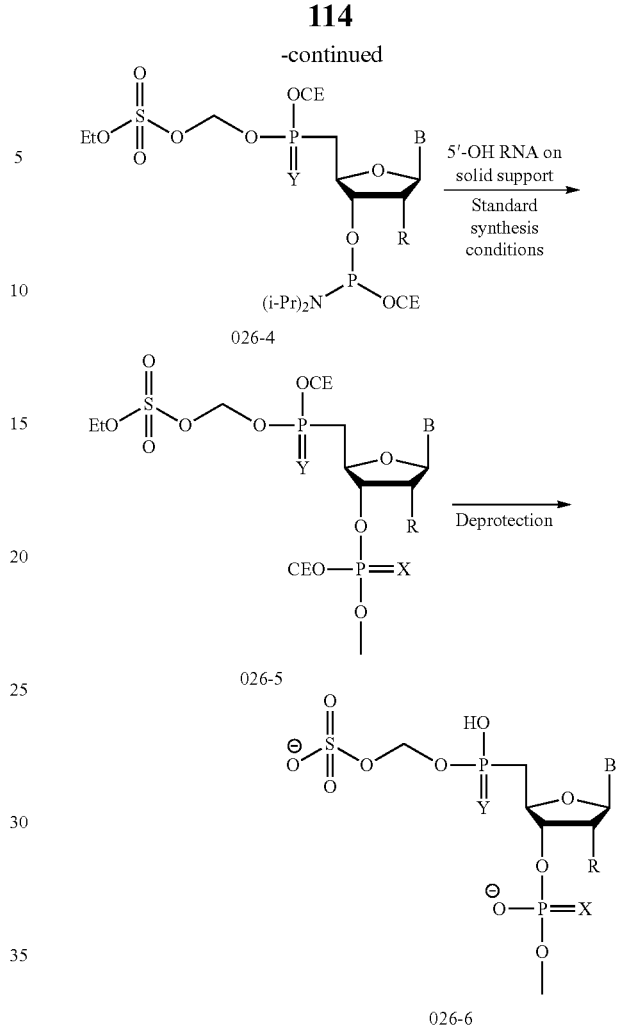
026-4
026-5
026-6
Scheme 19
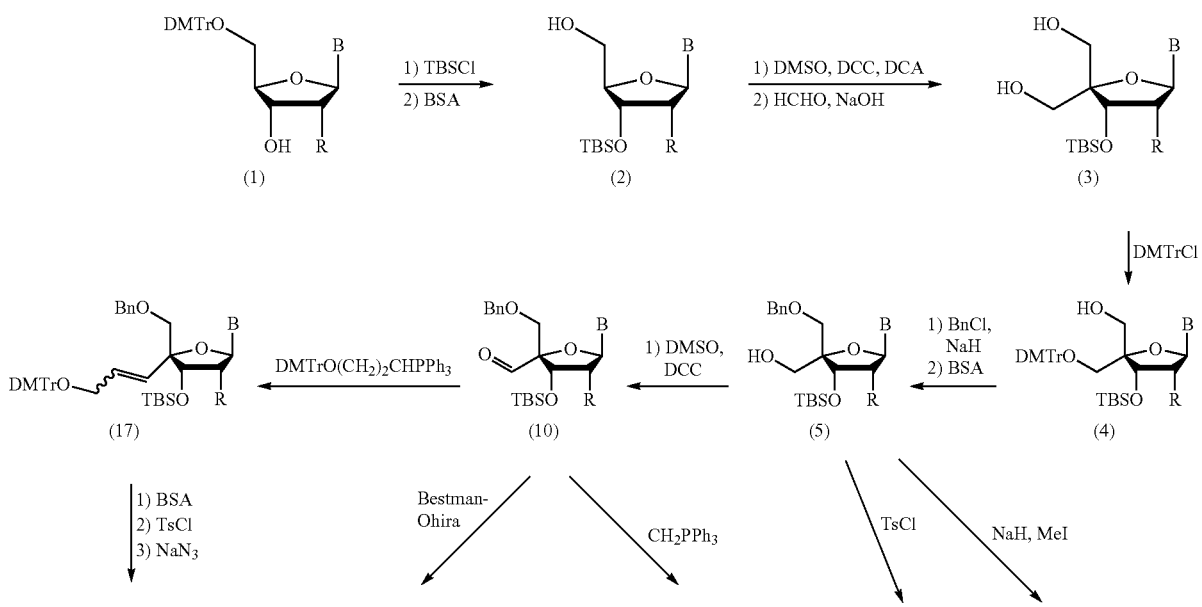

115 116
-continued
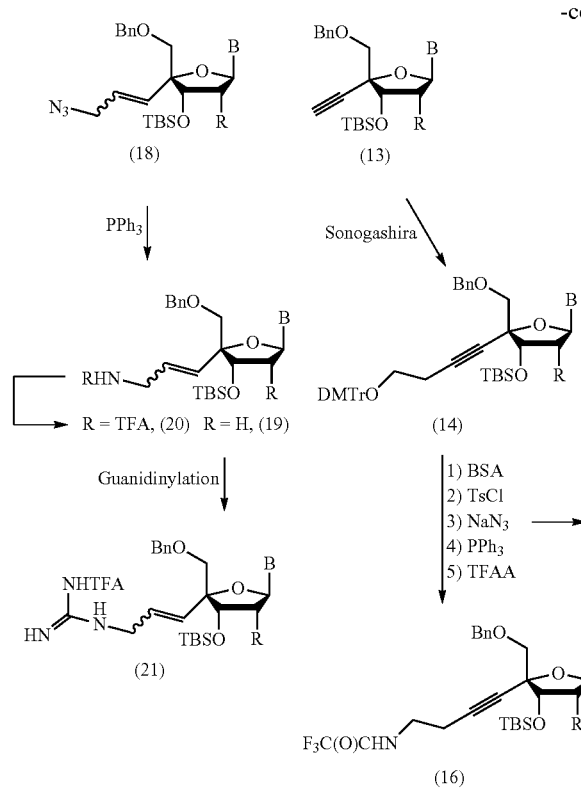
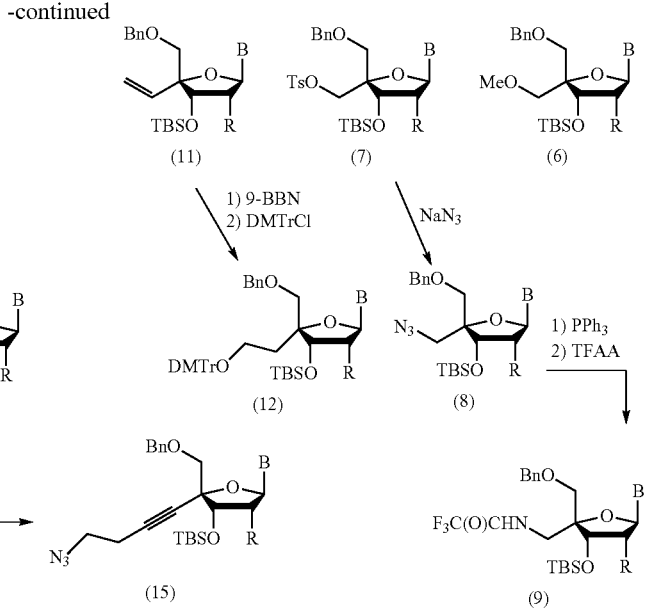
Scheme 20
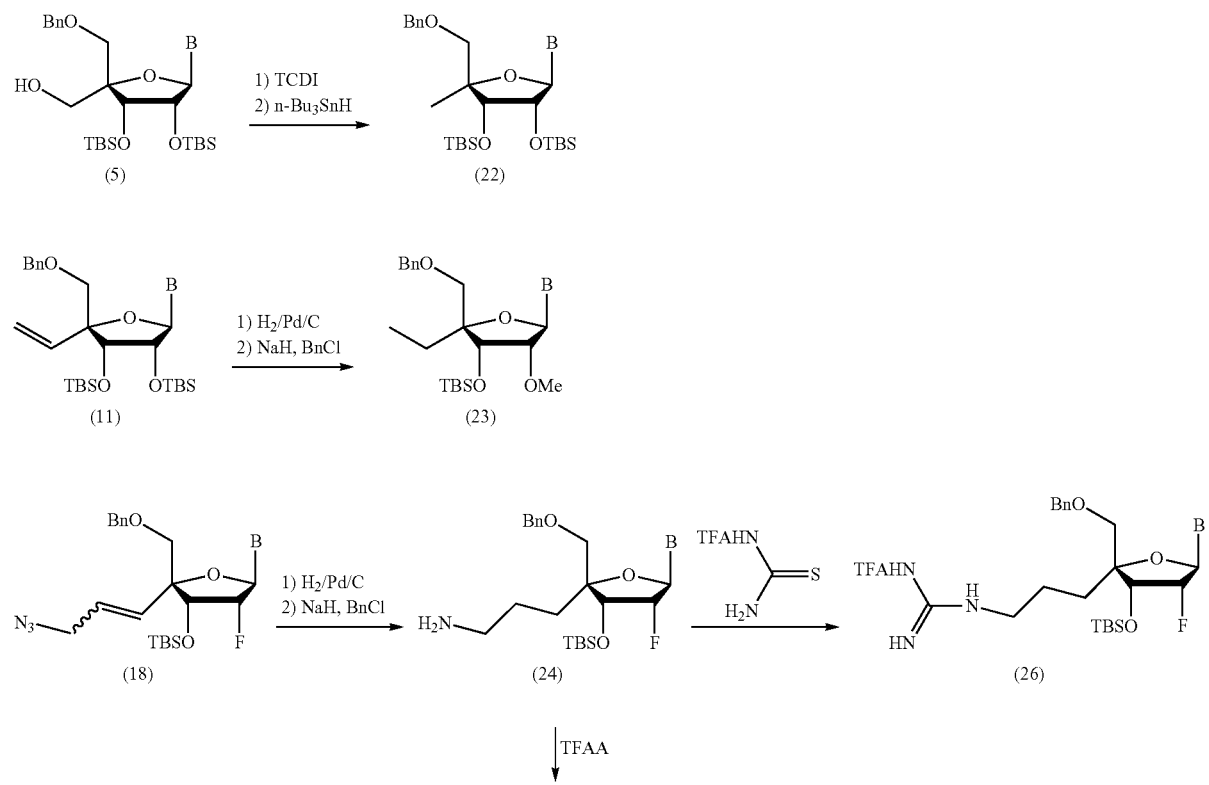

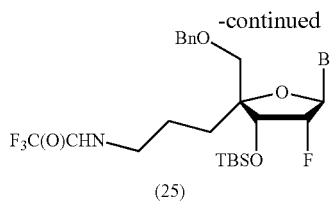
(25)
Scheme 21
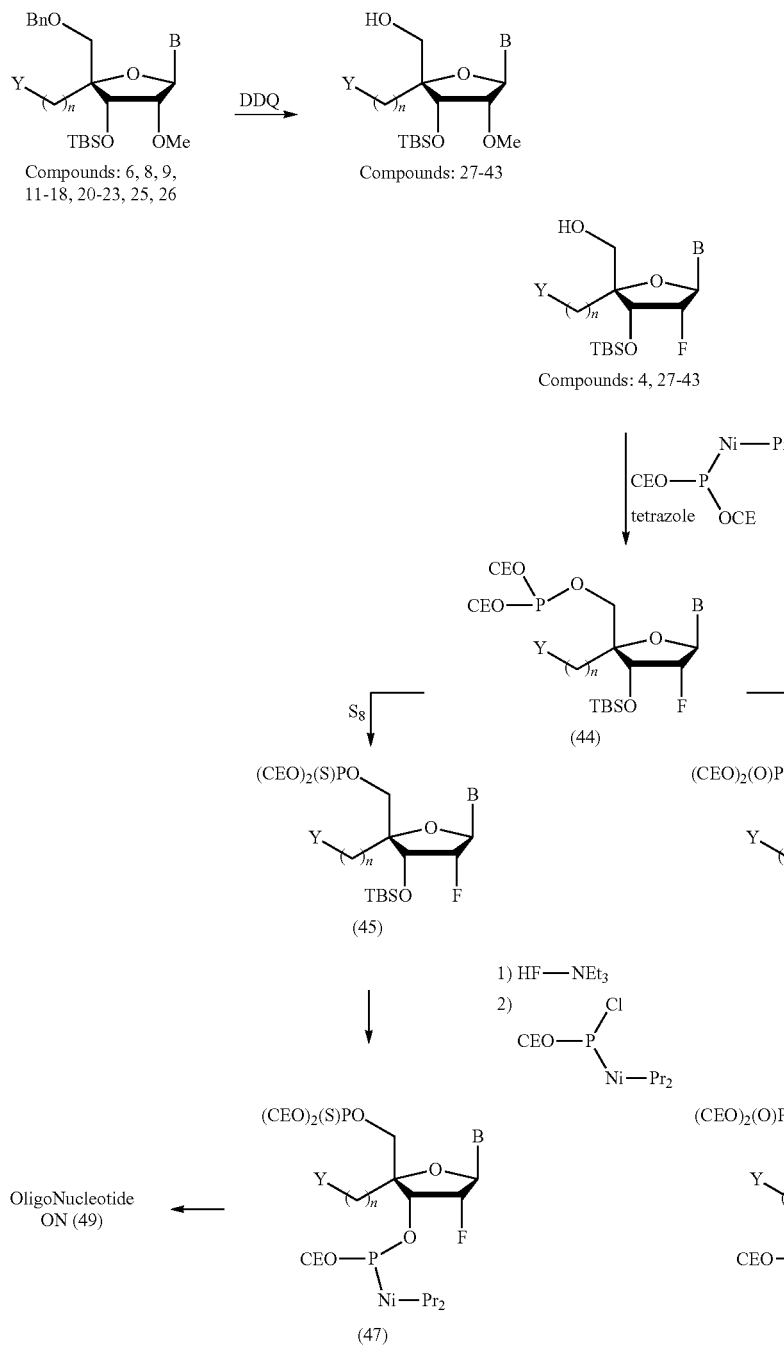

Scheme 22
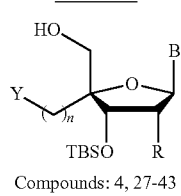
Compounds: 4, 27-43
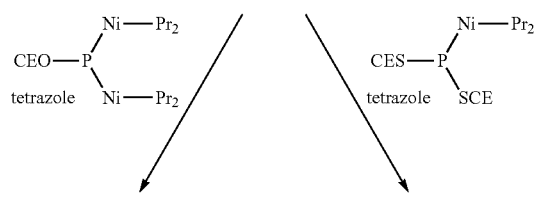
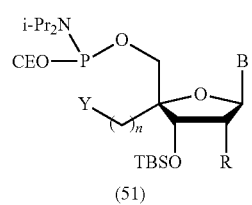
(51)
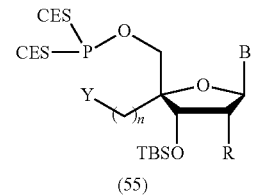
(55)
tetrazole
H₂S ↓
S₈ ↓
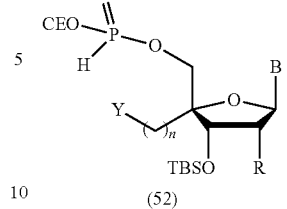
(52)
1) S₈
2) HF—TEA
3) 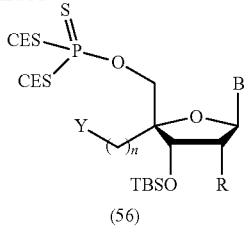 ↓
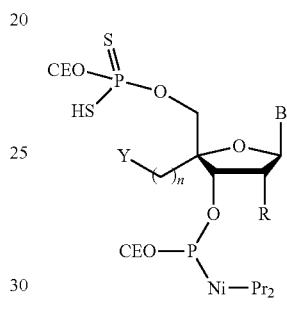
(53)
↓
ON (54)
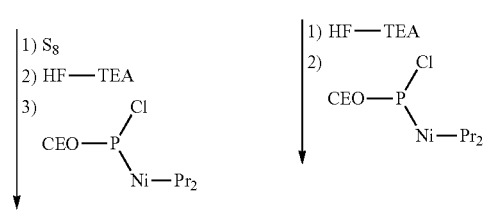
(56)
1) HF—TEA
2) ↓
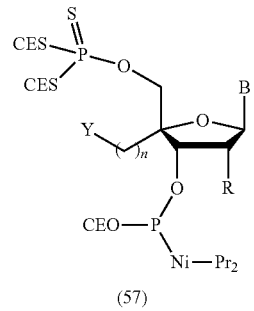
(57)
↓
ON (58)
Scheme 23
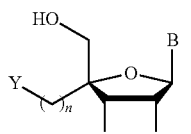
Compounds: 4, 27-43
1) TsCl
2) Me₃Si—S—SiMe₃ ↓
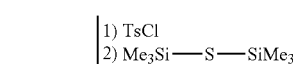
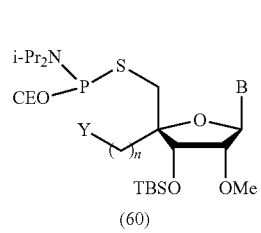
(60)
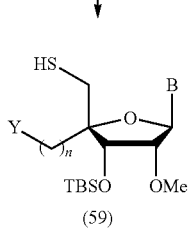
(59)
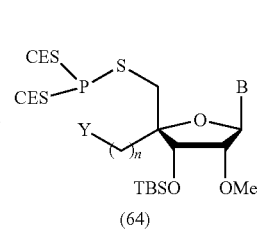
(64)
tetrazole
H₂S ↓
S₈ ↓

121
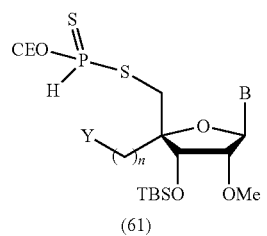
(61)
1) S₈
2) HF—TEA
3) <image below>
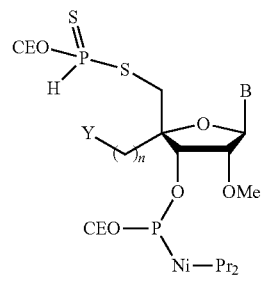
(62)
↓
ON (63)
-continued
122
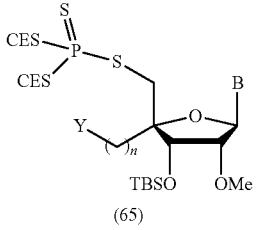
(65)
1) HF—TEA
2) <image below>
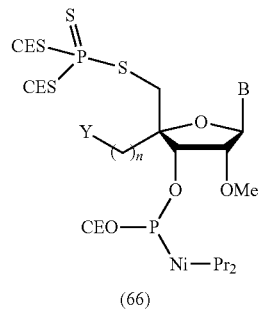
(66)
↓
ON (67)
Scheme 24
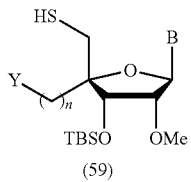
(59)
↓ tetrazole, CEO—P(Ni—Pr₂)(OCE)
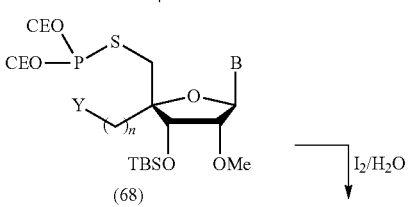
(68)
S₈ ↙     ↘ I₂/H₂O

Scheme 25 (A and B)

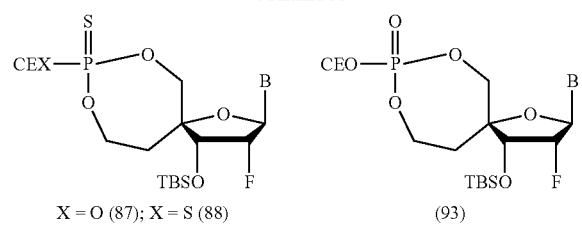
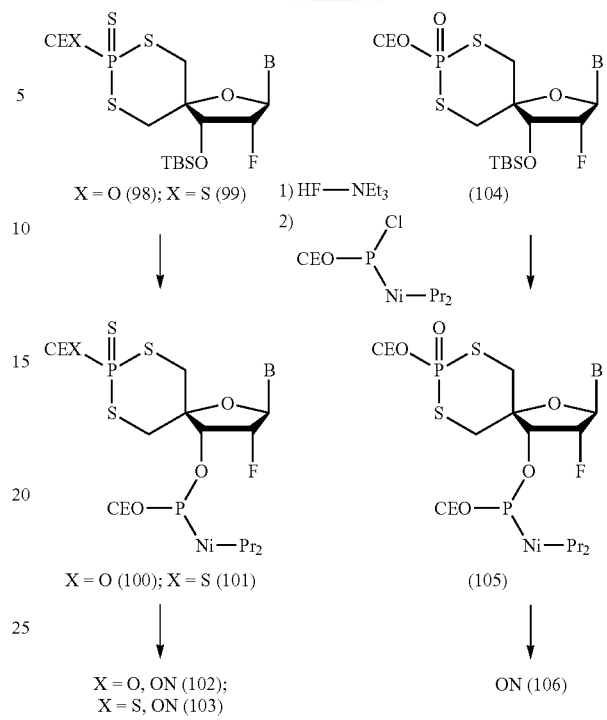
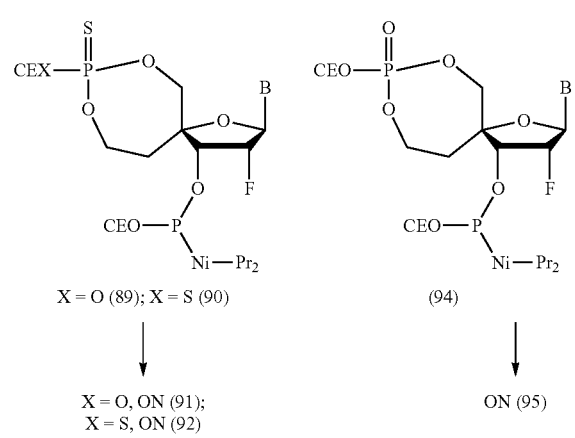
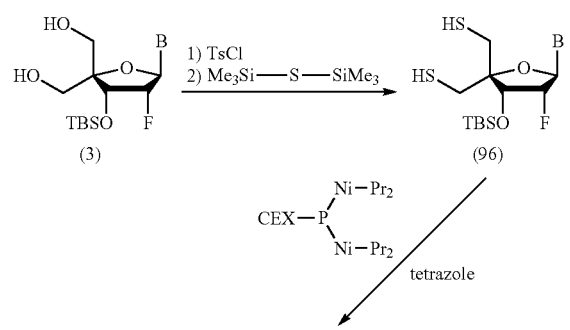
Scheme 26 (A and B)
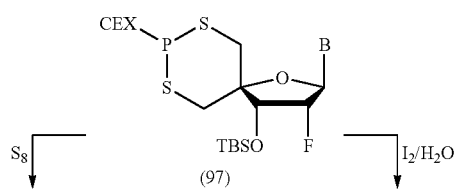
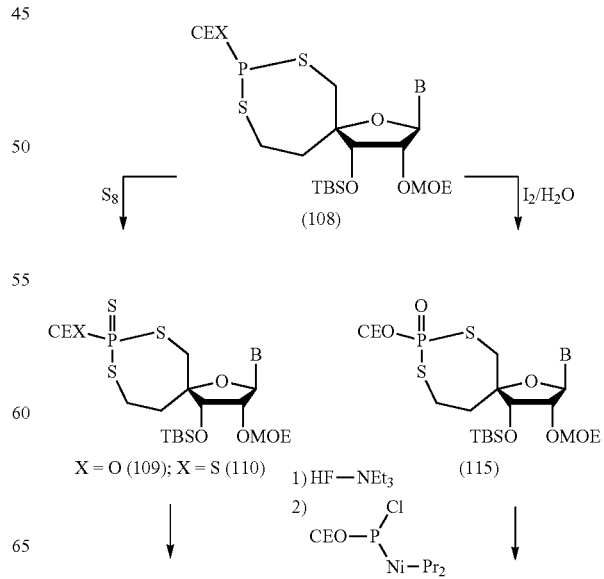

127
-continued
128
-continued
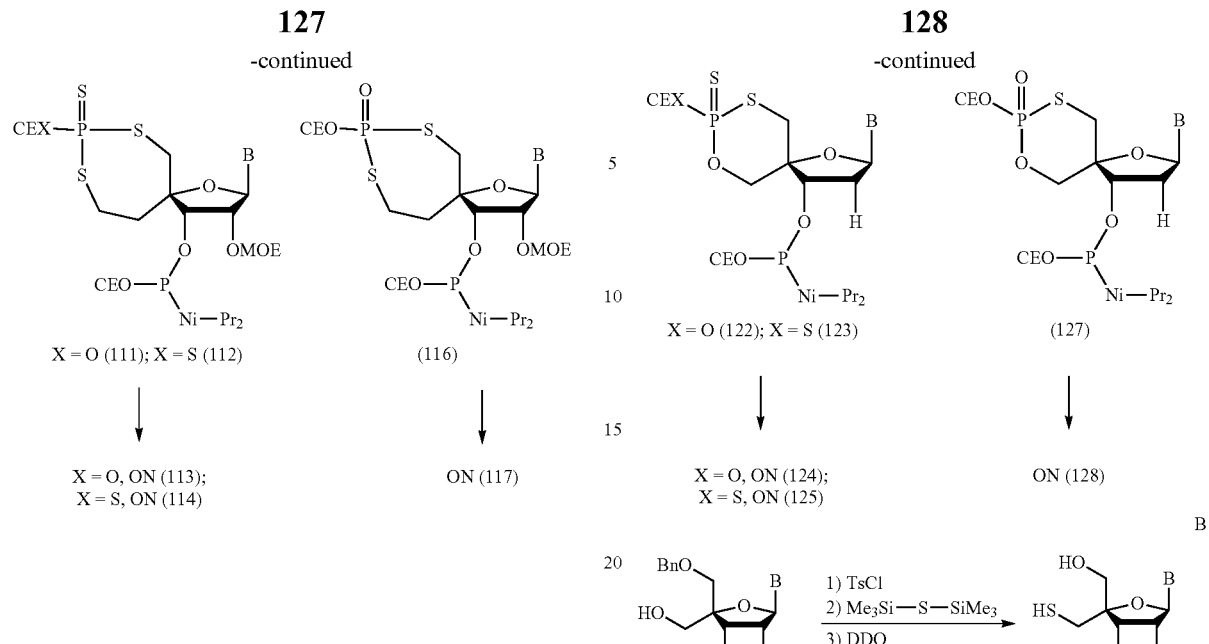
Scheme 27 (A and B)
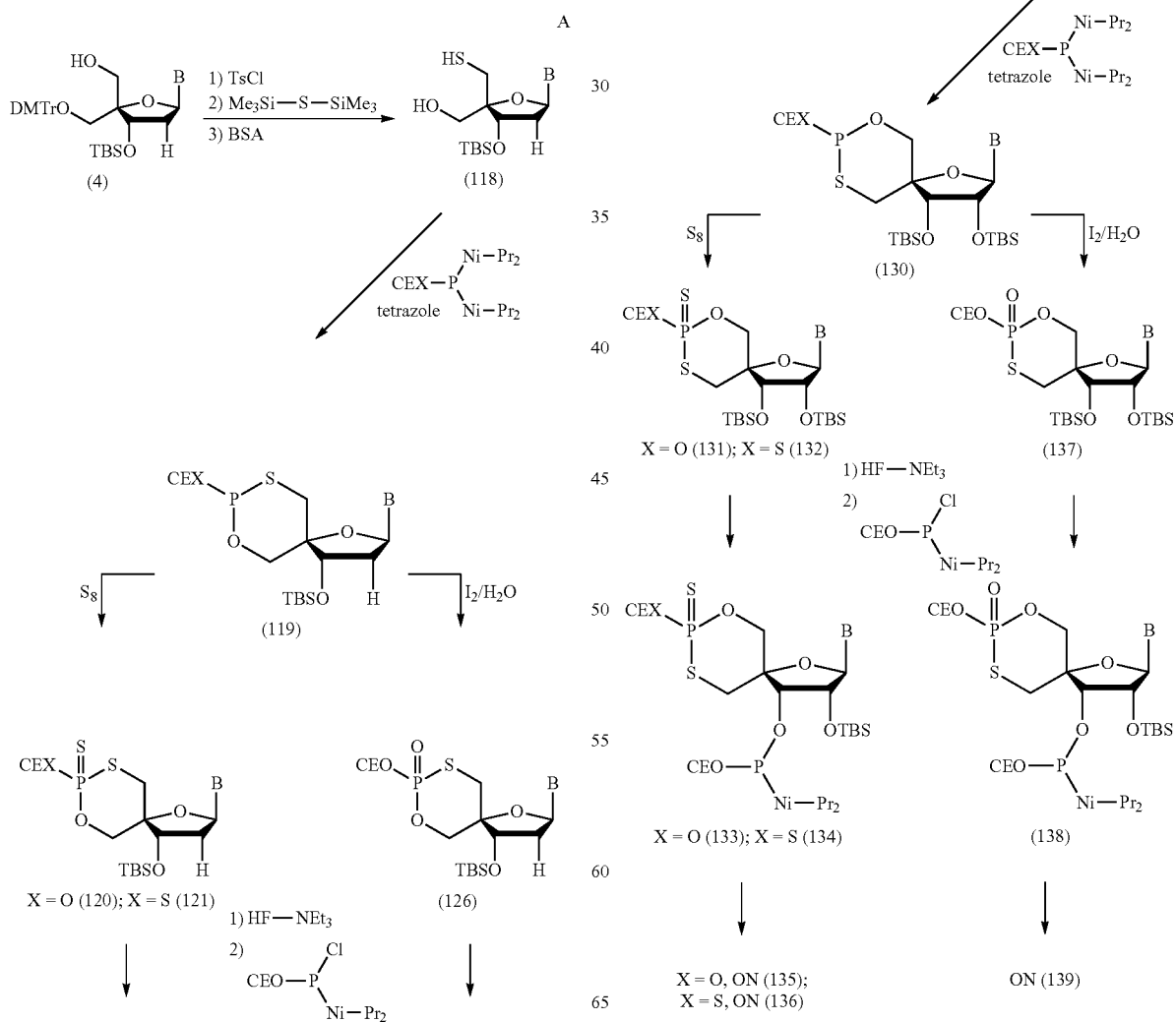

Scheme 28 (A and B)
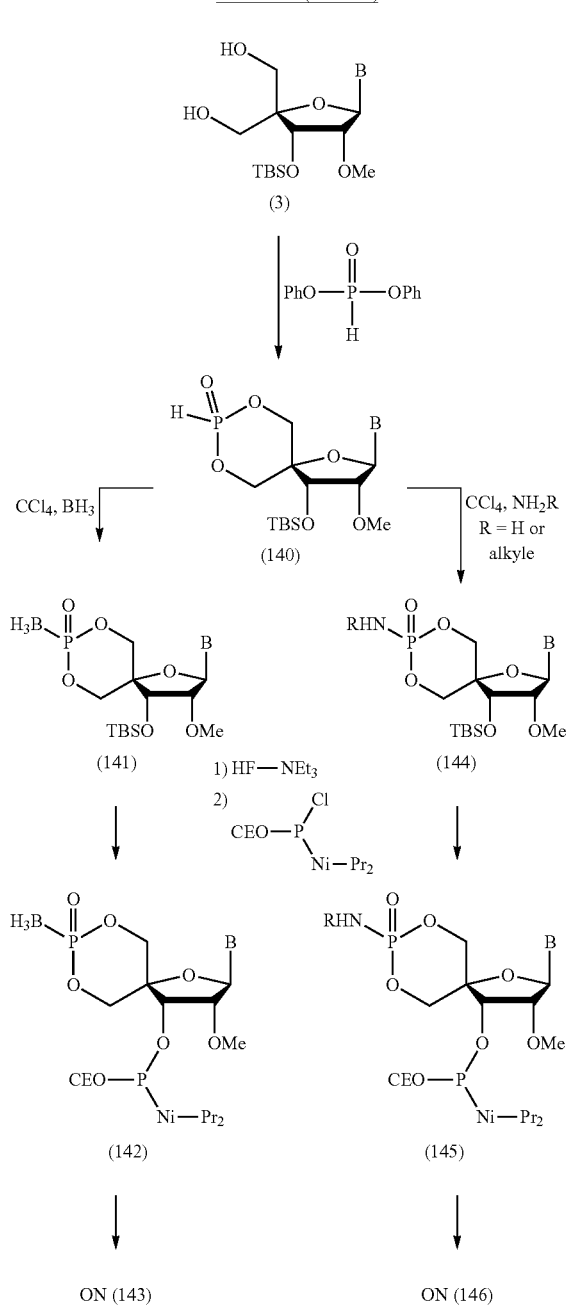
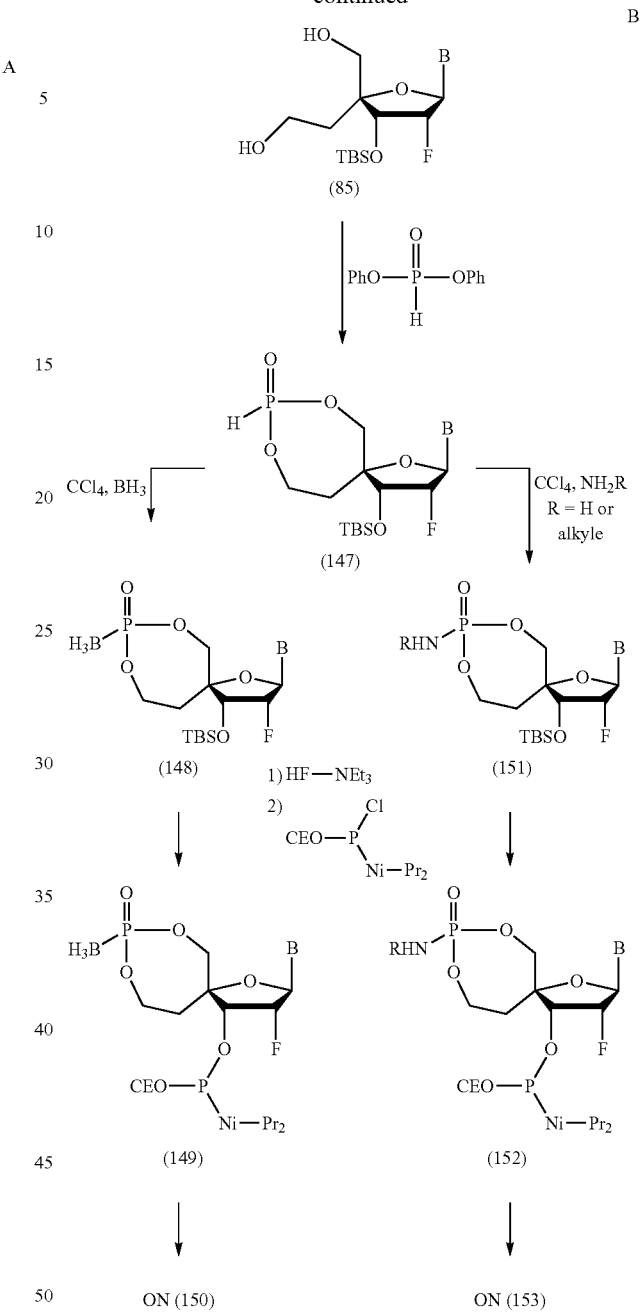

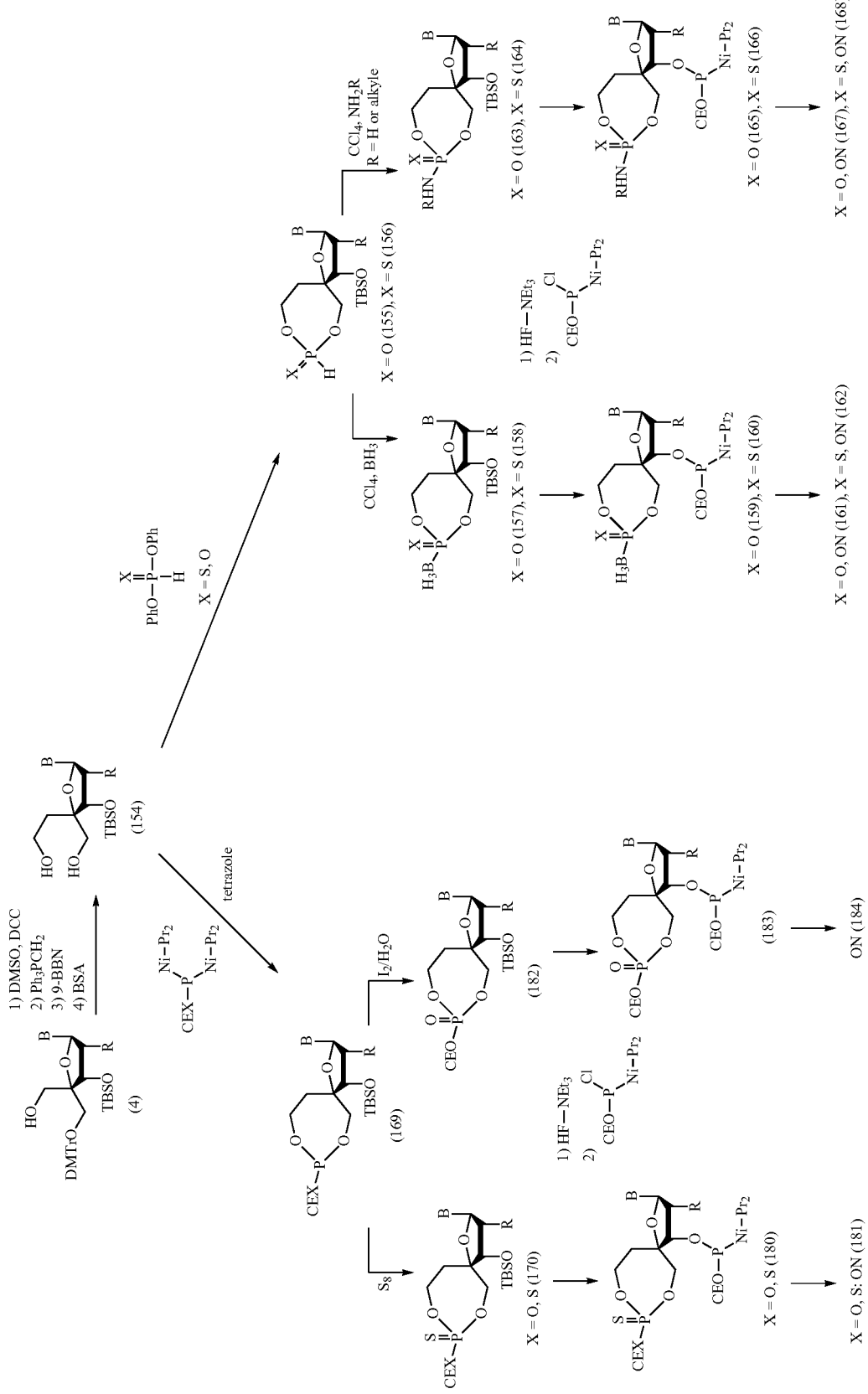

Scheme 30 (A and B)
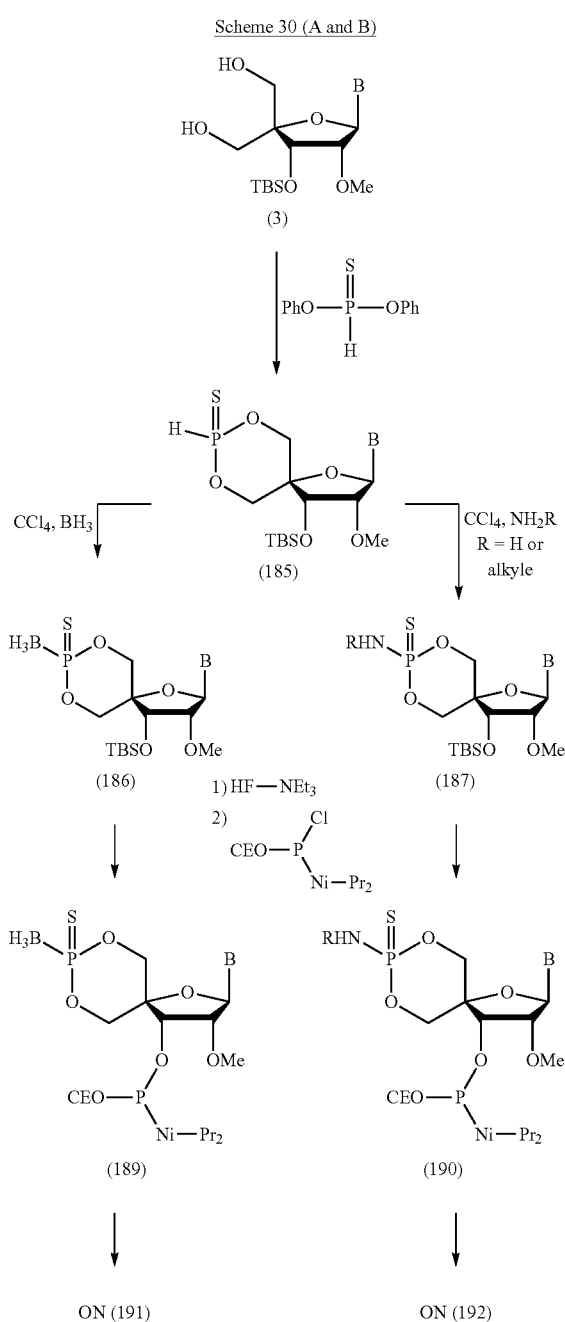
-continued
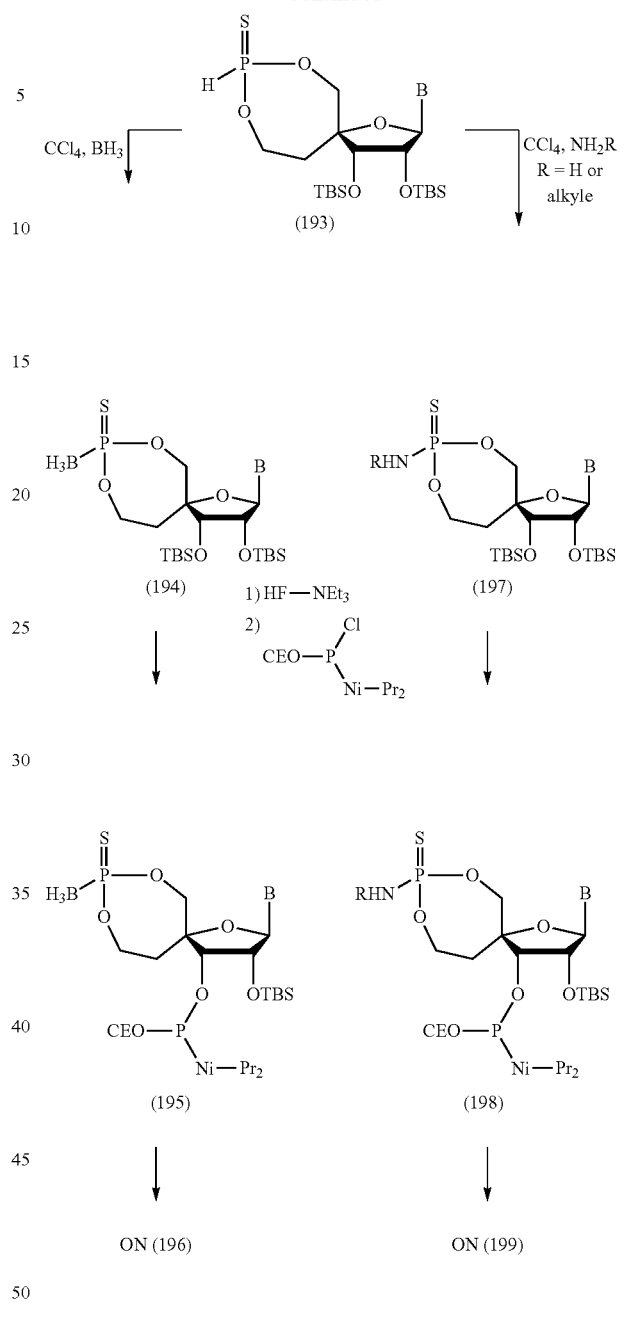
Scheme 31 (A and B)
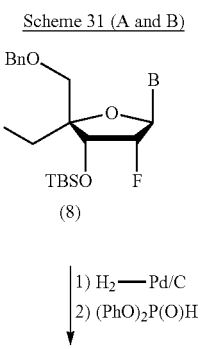

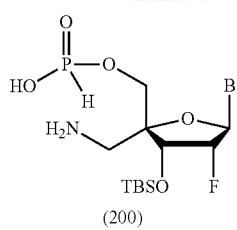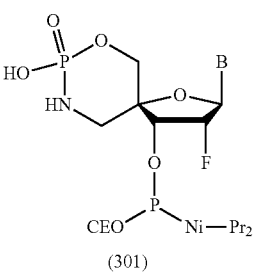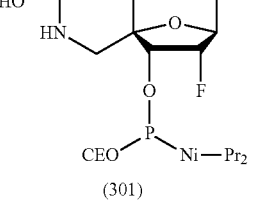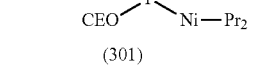

137
-continued
138
-continued
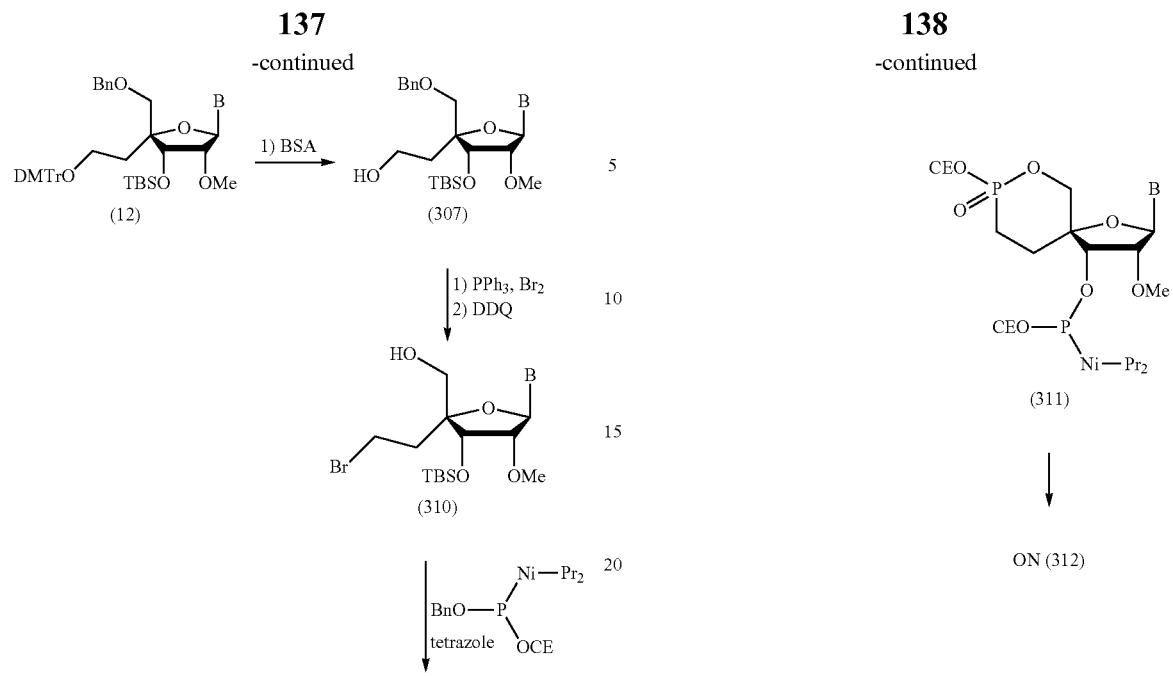
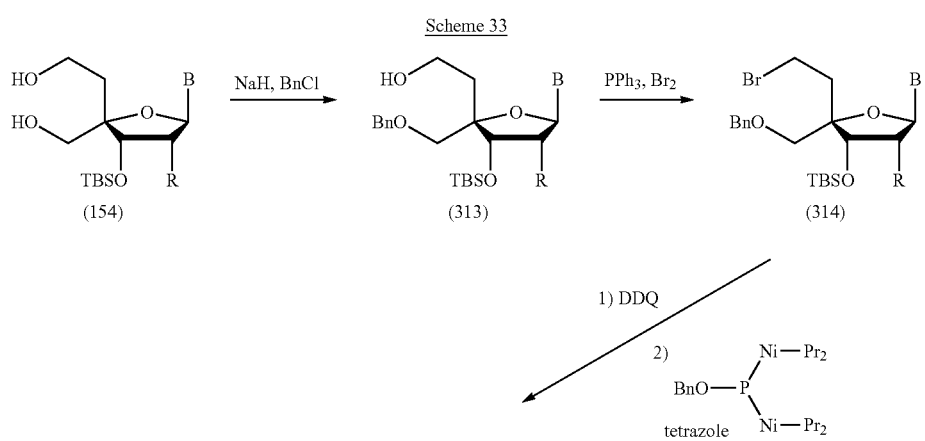
Scheme 33
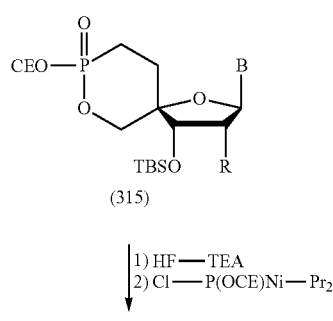

-continued
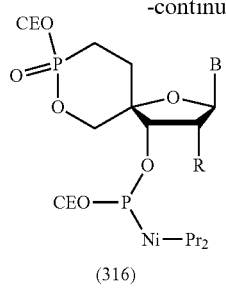
(316)
ON (317)

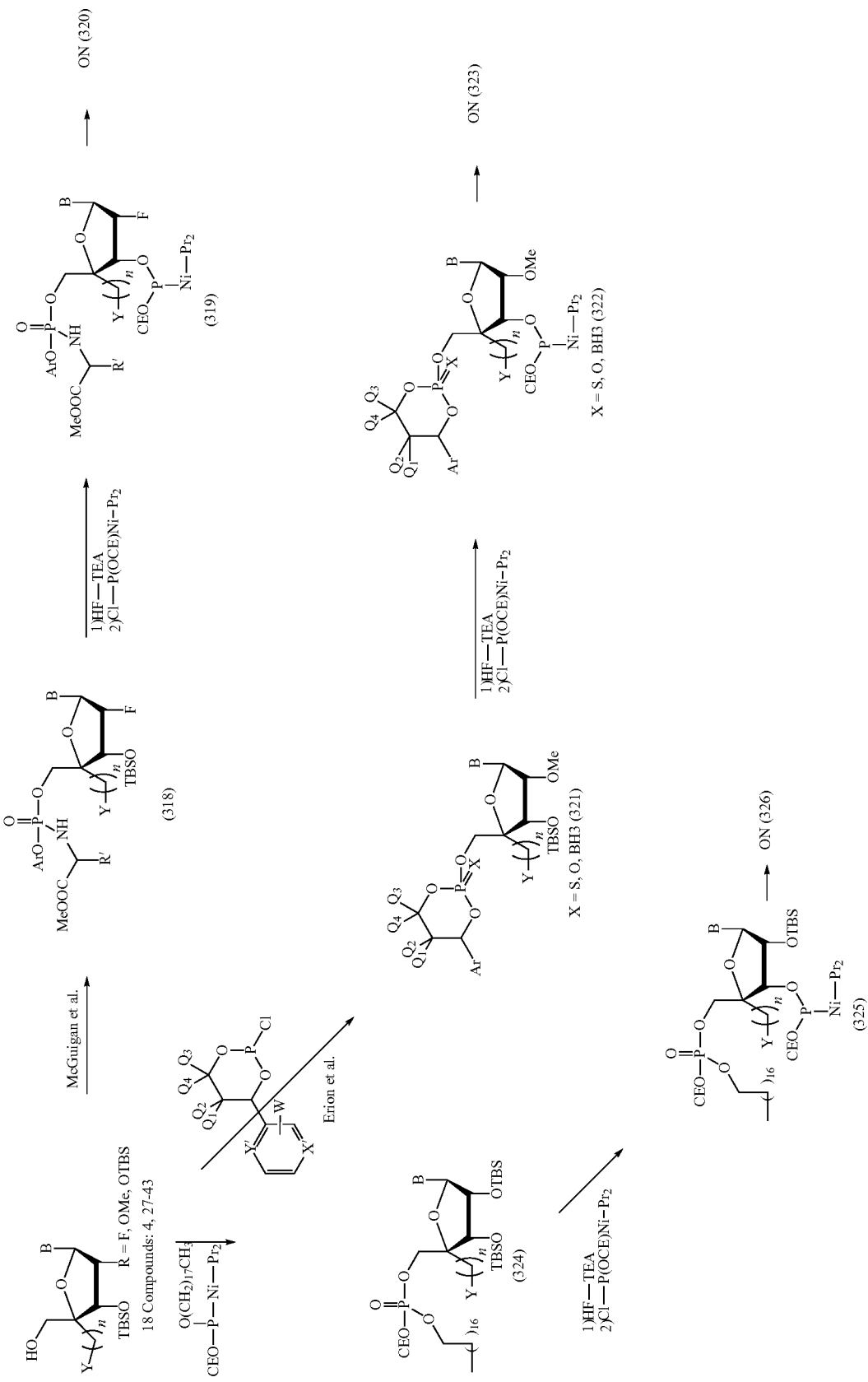
Scheme 34

Scheme 35
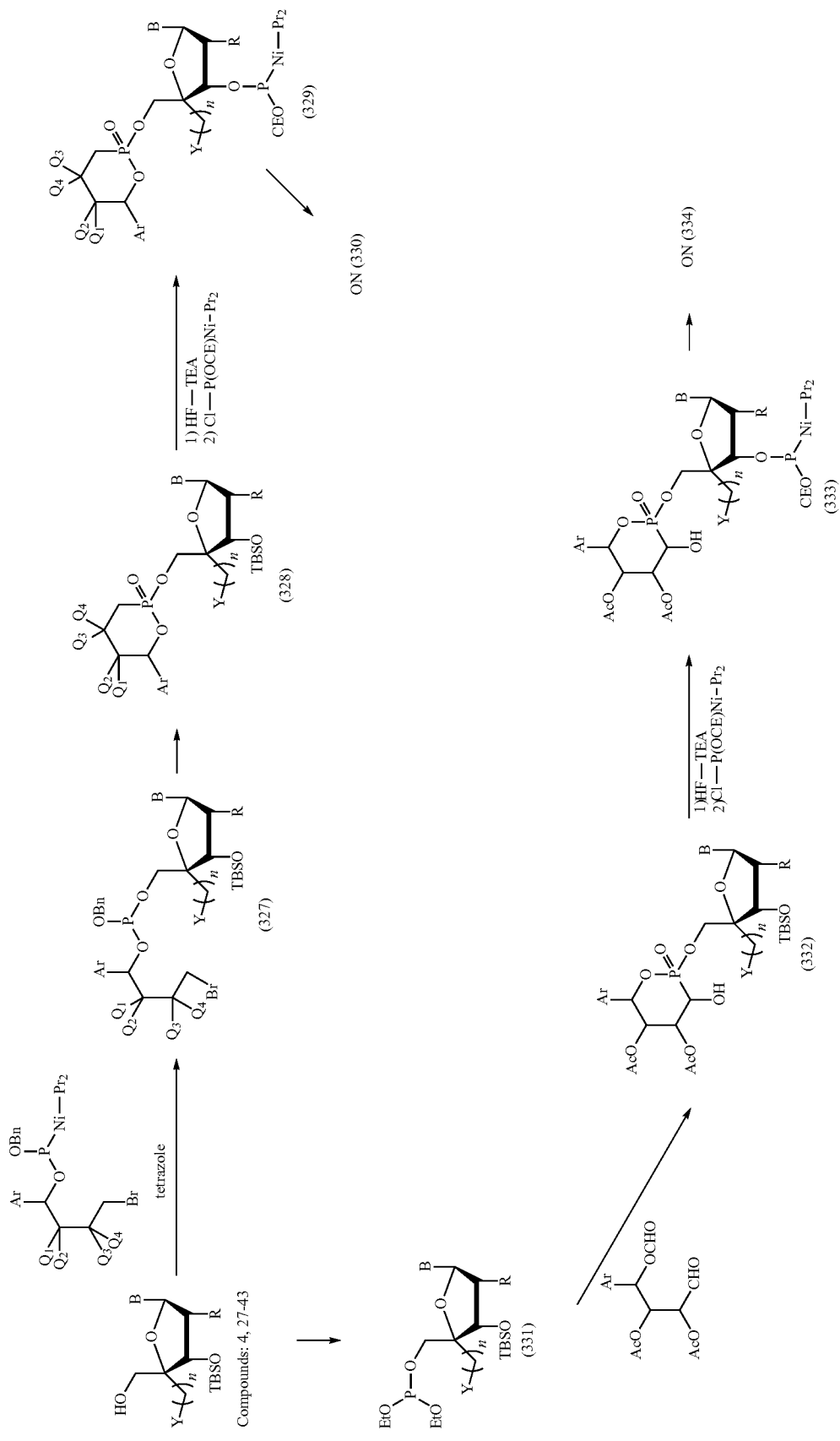

Scheme 36
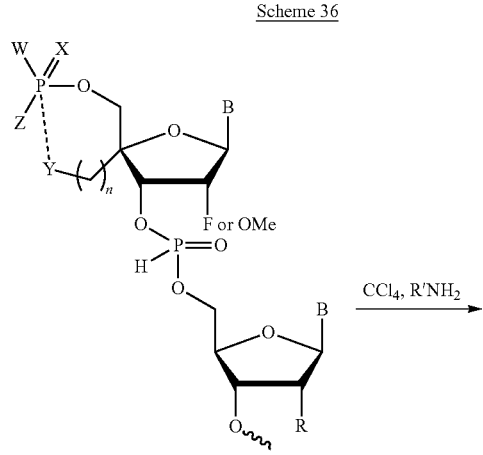
4' Modified ONs:
49, 50, 54, 58, 63, 67, 71, 74
5'-4' Cyclic ONs:
83, 84, 78, 91, 92, 95, 102, 103, 106, 113, 114, 117, 124, 125, 128, 135, 136, 139, 143, 146, 150, 153, 181, 184
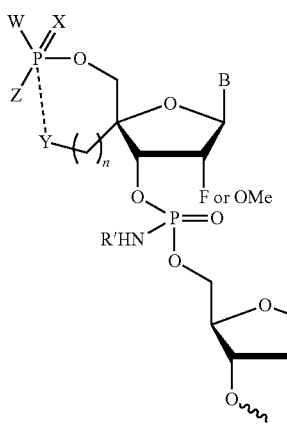
Phosphate bridge mimics between position 1 and 2 (5'-end)
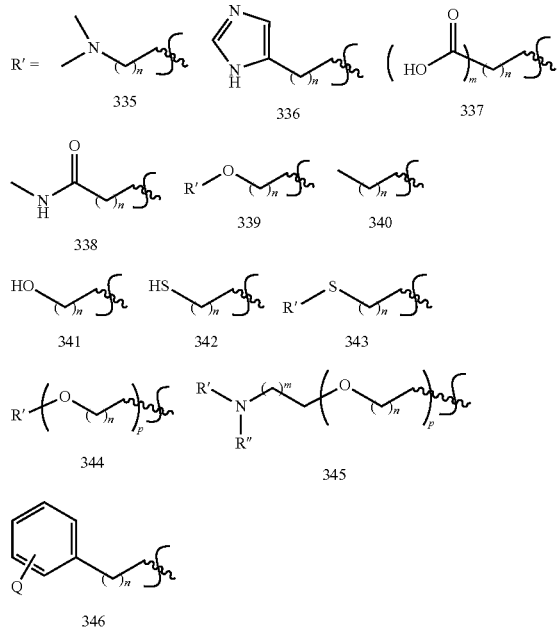
4' Modified ONs:
49, 50, 54, 58, 63, 67, 71, 74
5'-4' Cyclic ONs:
83, 84, 78, 91, 92, 95, 102, 103, 106, 113, 114, 117, 124, 125, 128, 135, 136, 139, 143, 146, 150, 153, 181, 184
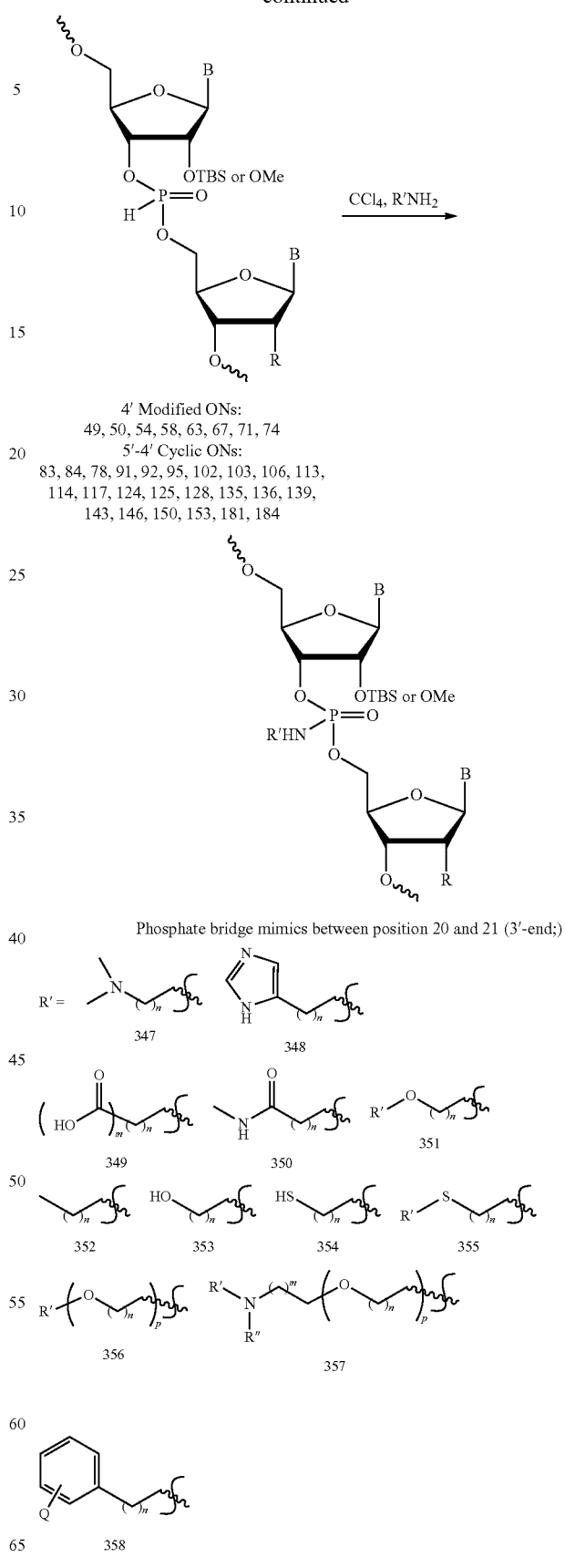
Phosphate bridge mimics between position 20 and 21 (3'-end;)

Scheme 37
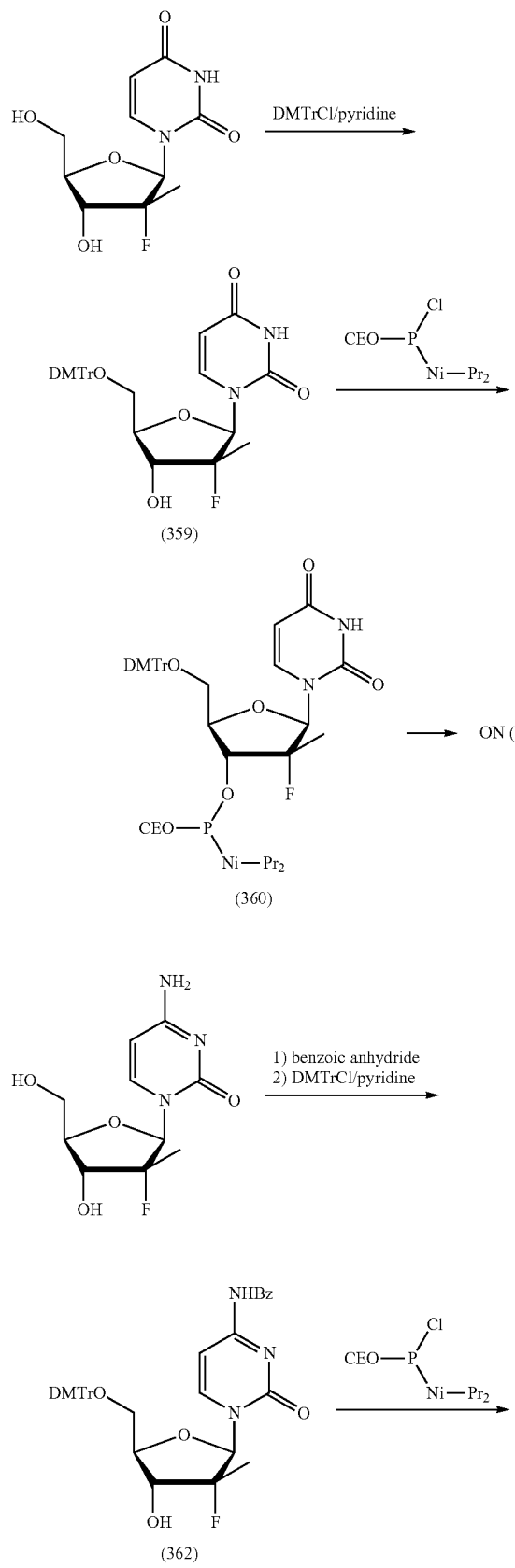
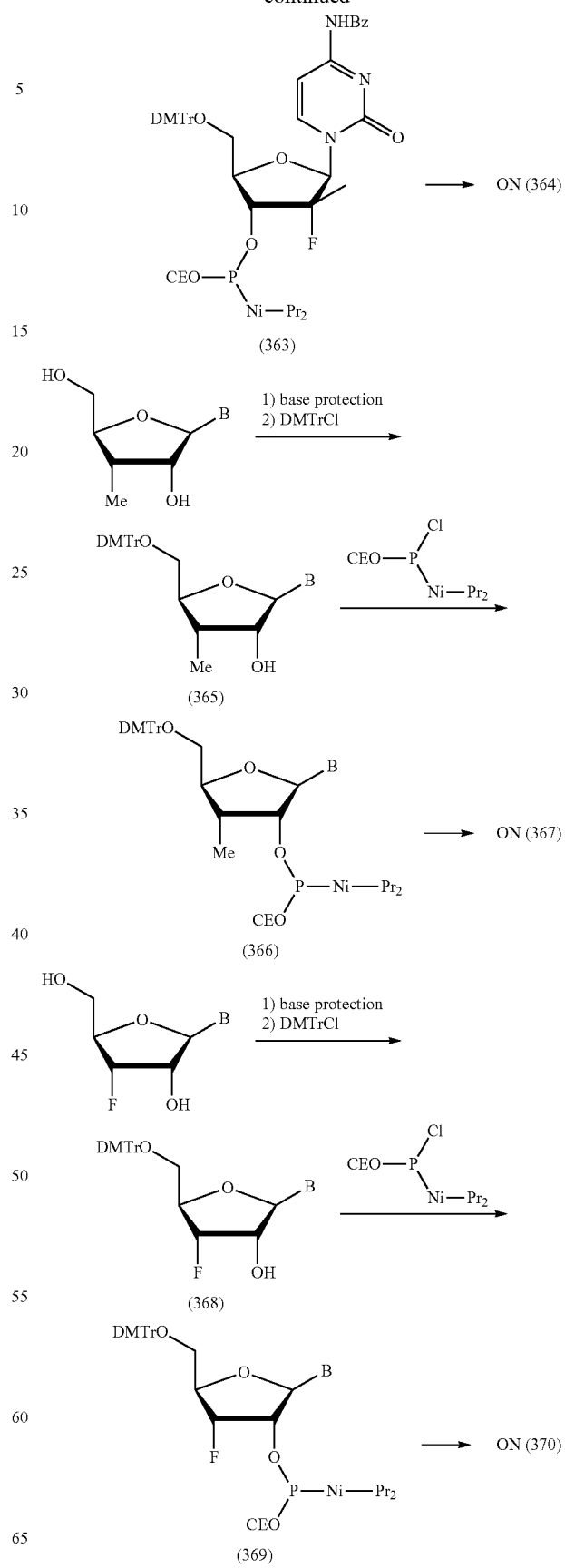

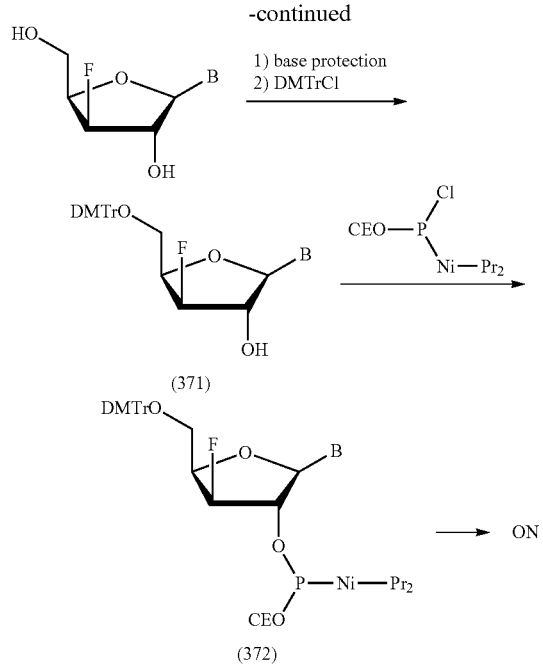
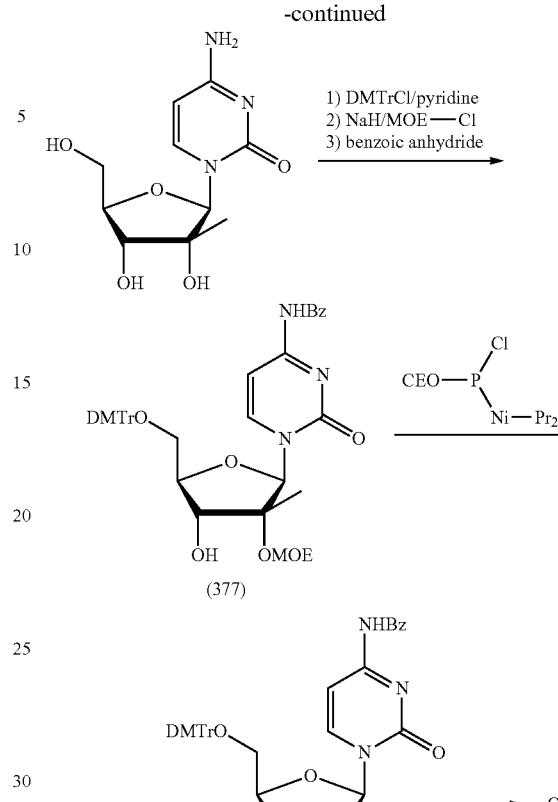
Scheme 38
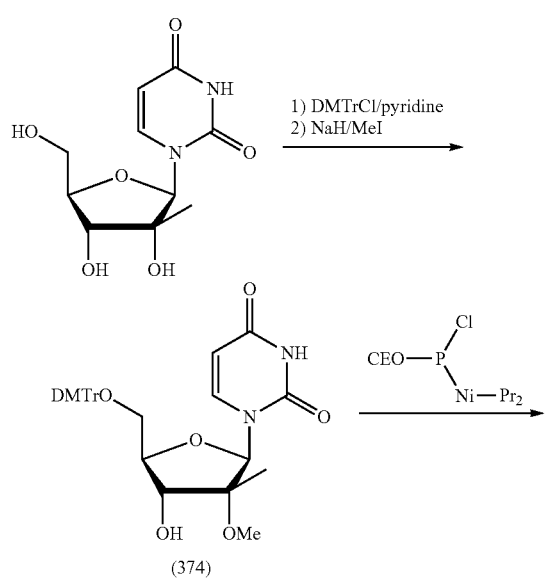
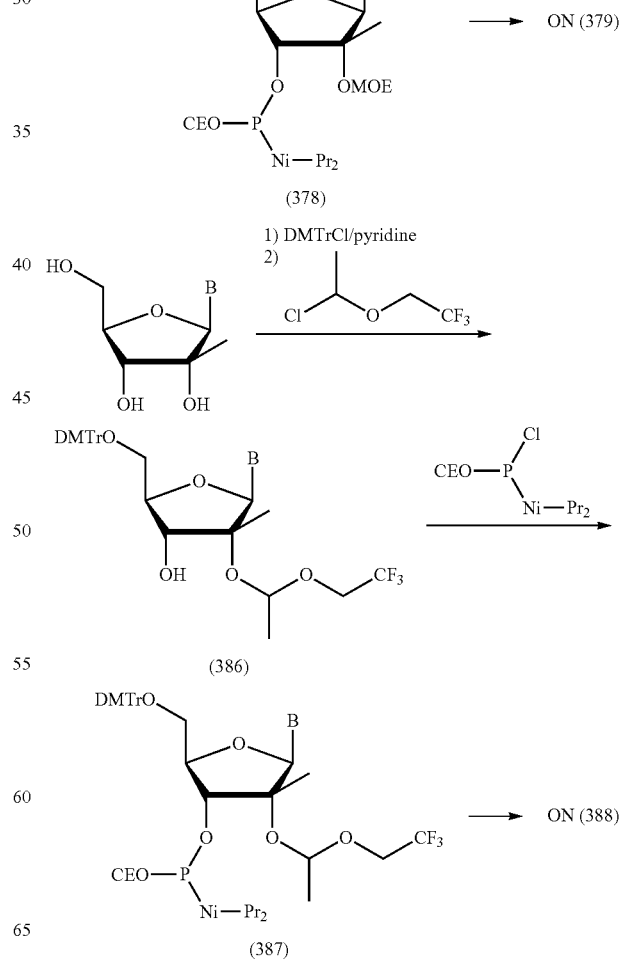

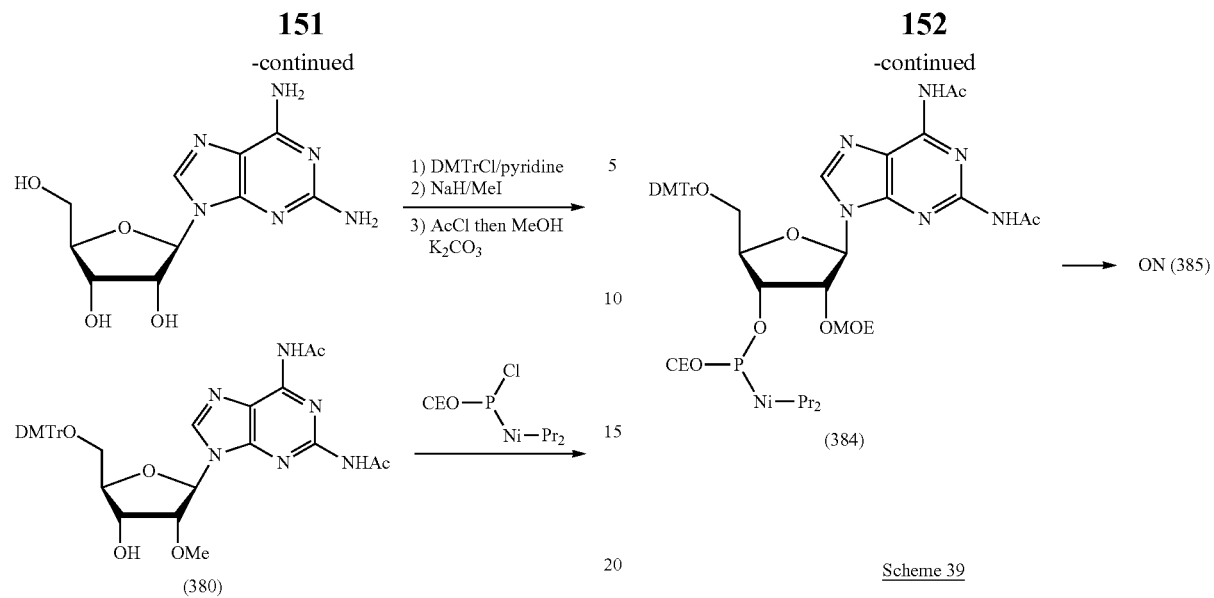
Scheme 13
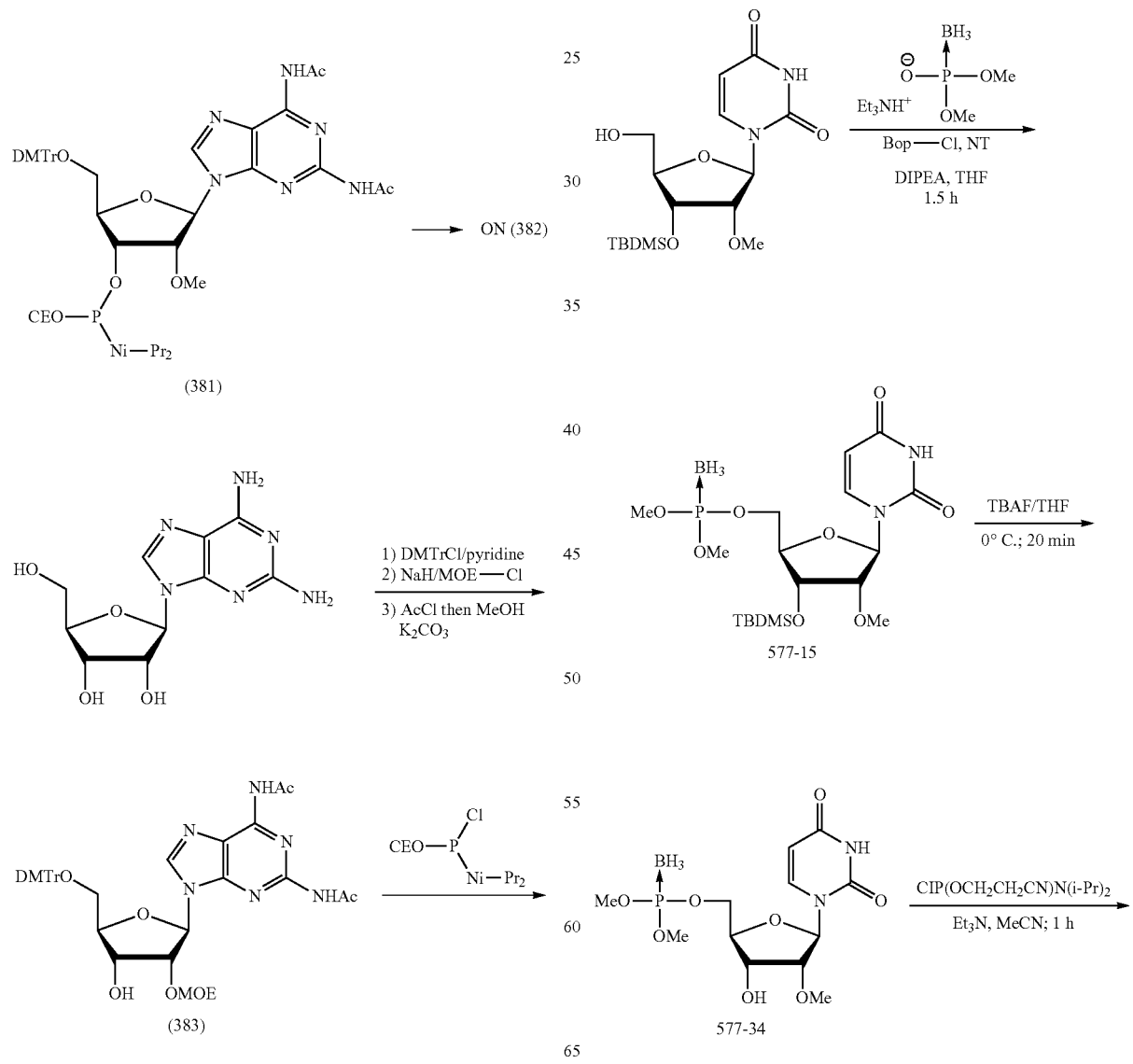
Scheme 39

153
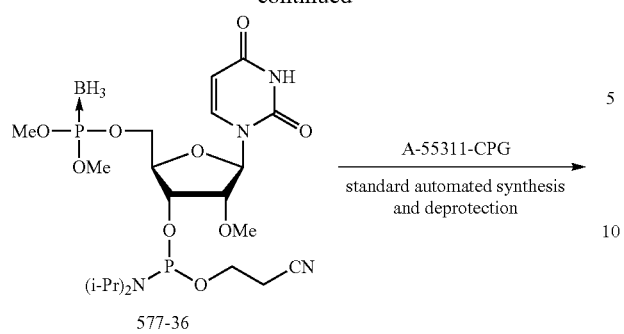
577-36
A-55311-CPG
standard automated synthesis
and deprotection
154
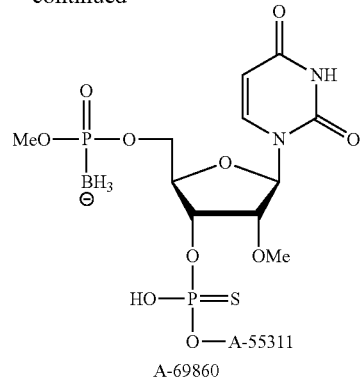
A-69860
Scheme 40
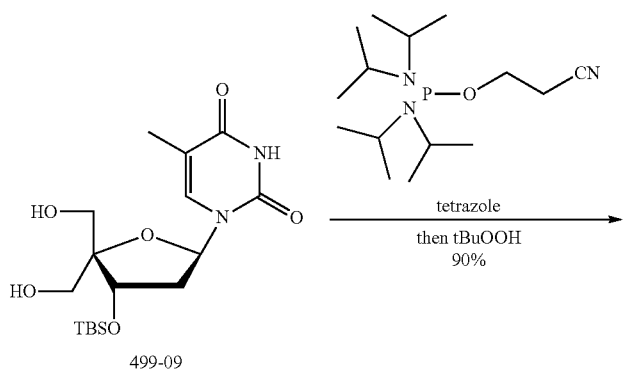
499-09
tetrazole
then tBuOOH
90%
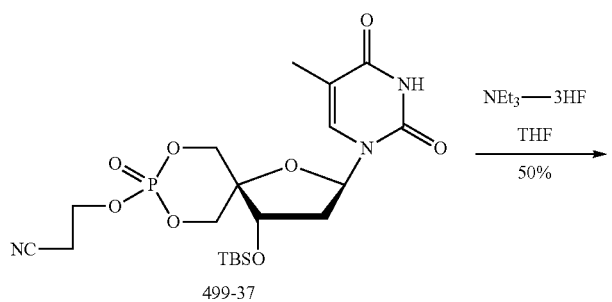
499-37
NEt$_3$—3HF
THF
50%
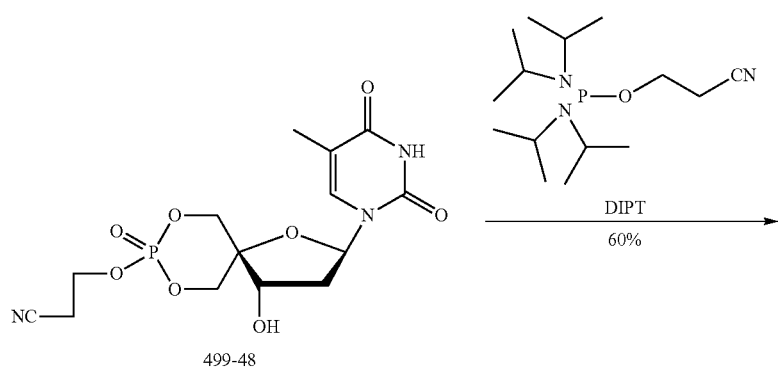
499-48
DIPT
60%

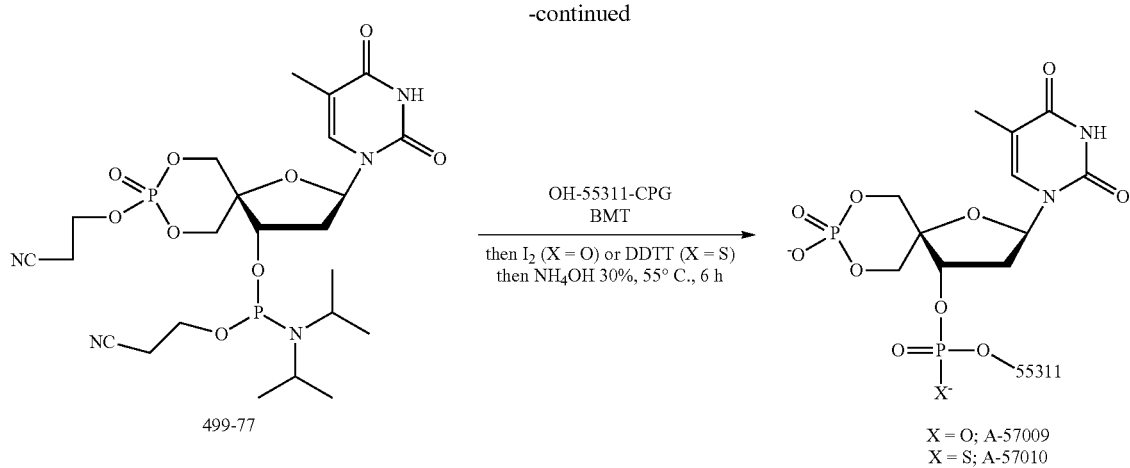
155                                              156
OH-55311-CPG
BMT
then I₂ (X = O) or DDTT (X = S)
then NH₄OH 30%, 55° C., 6 h
499-77
X = O; A-57009
X = S; A-57010
55311 = UfsgUfscUfscUfsgGfsuCfscUfsusAfscsUfsus(Aeos)(Aeo)
Scheme 41
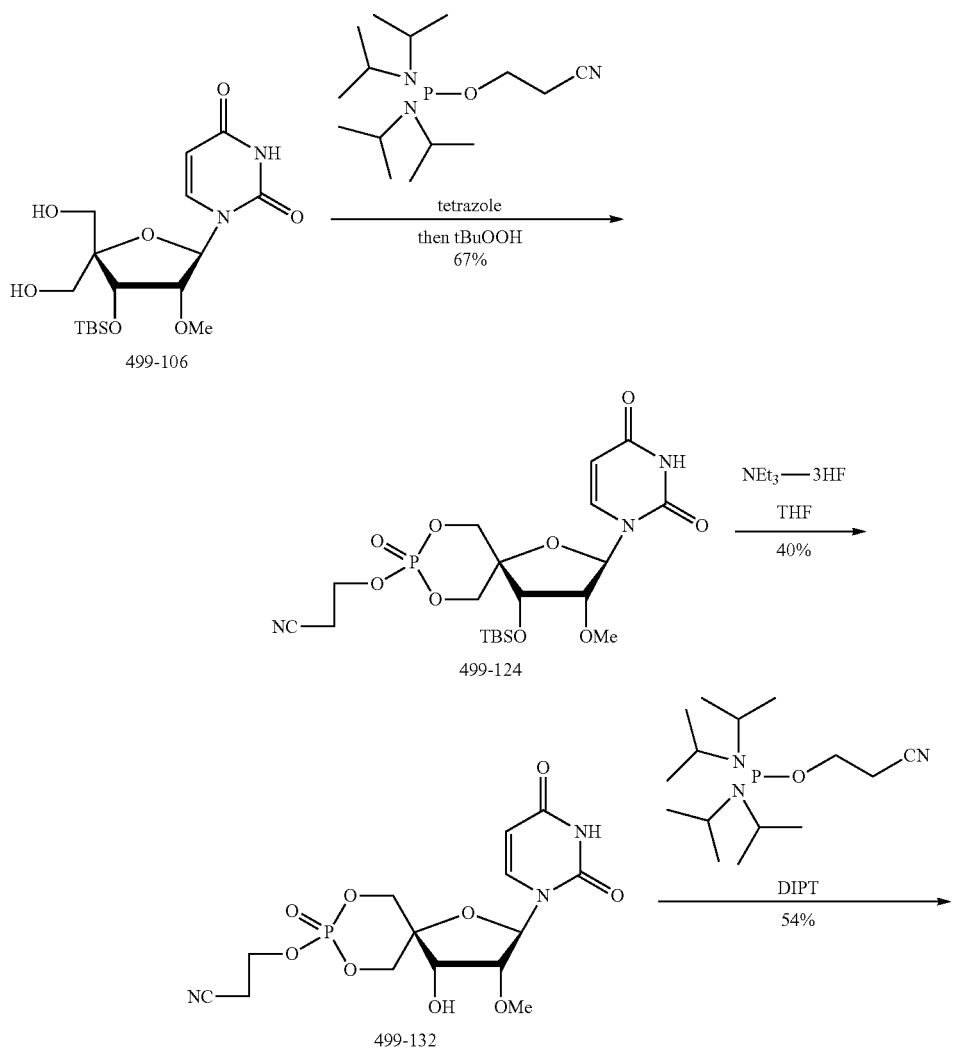
tetrazole
then tBuOOH
67%
499-106
NEt₃—3HF
THF
40%
499-124
DIPT
54%
499-132

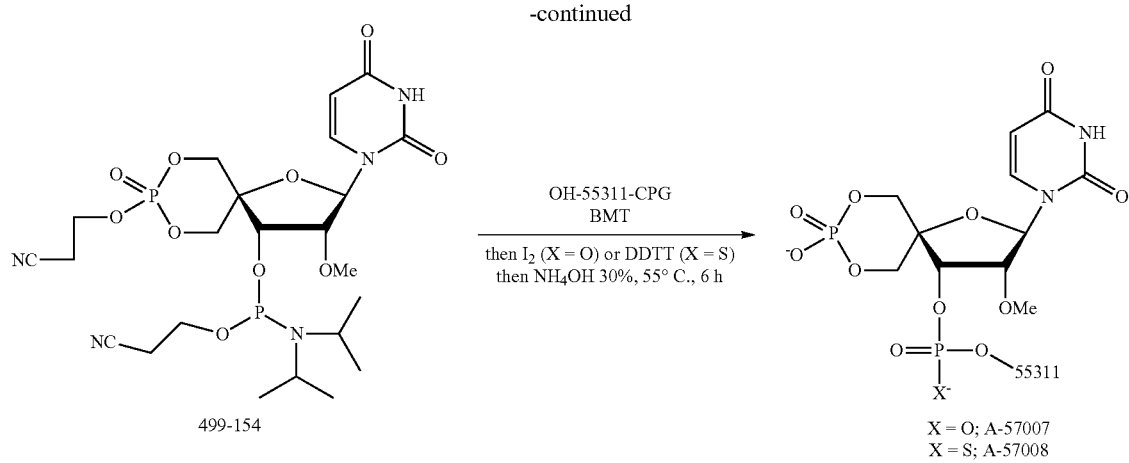
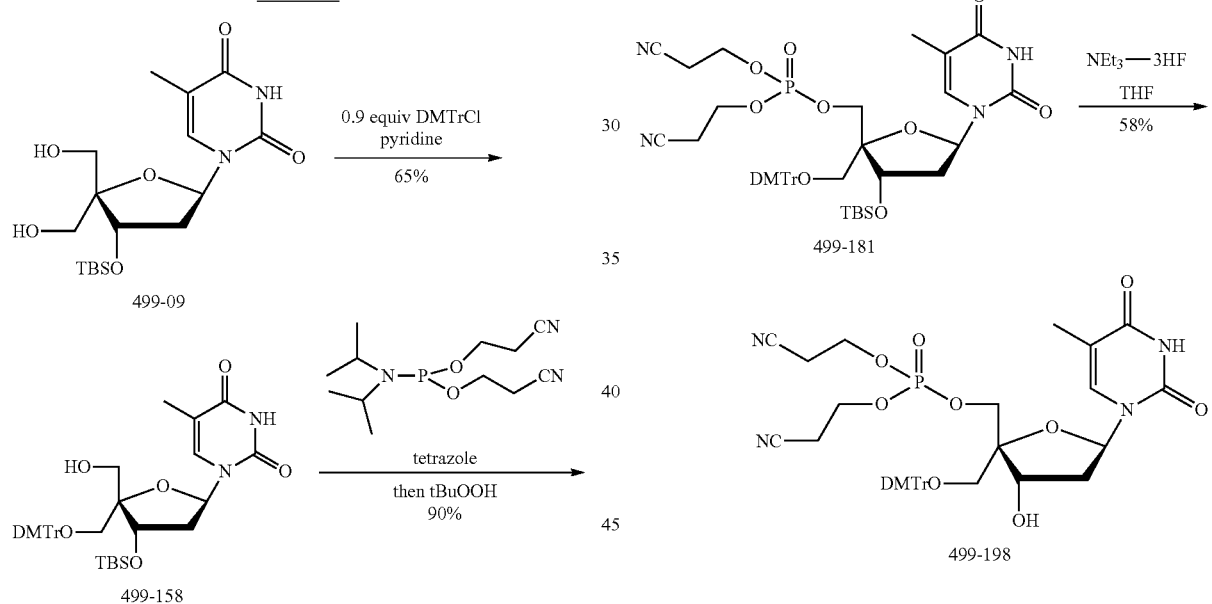
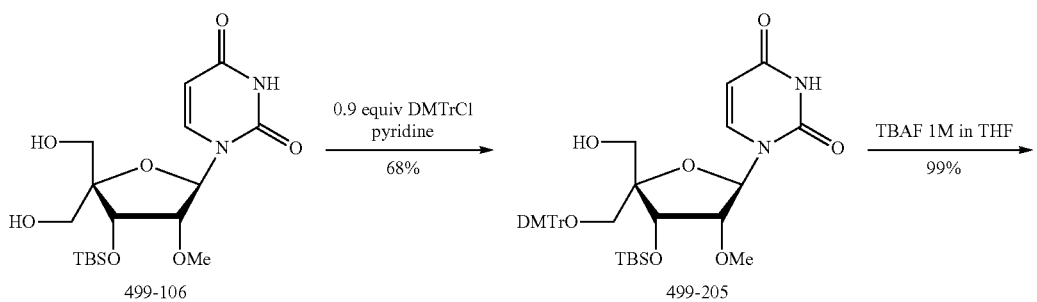

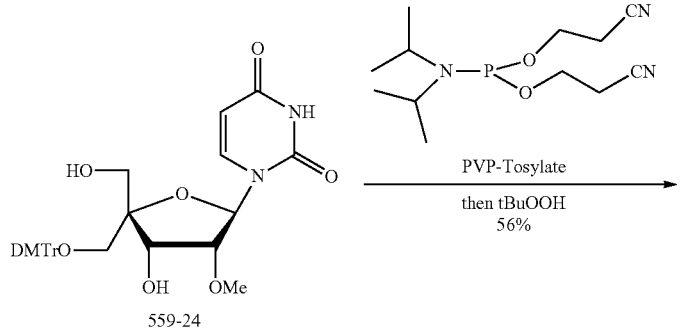
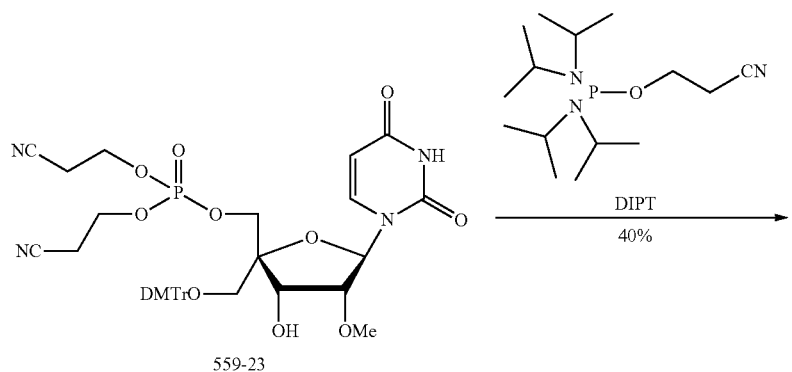
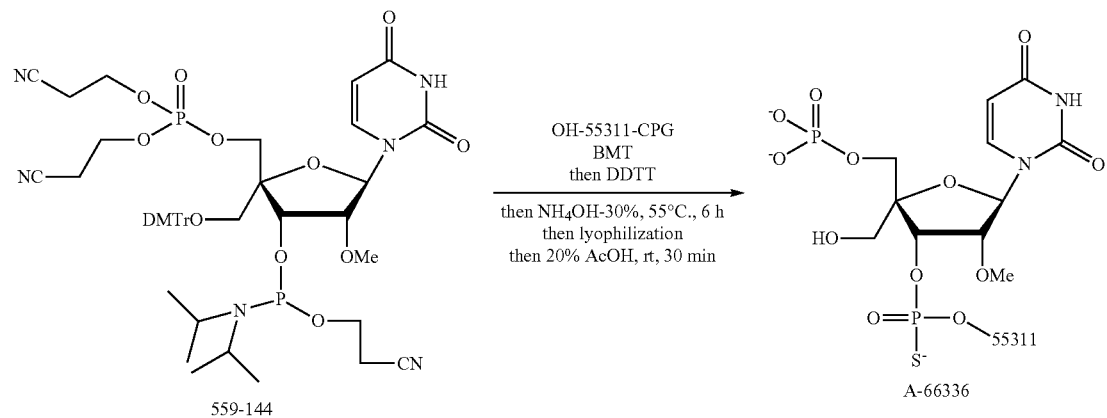
Scheme 44
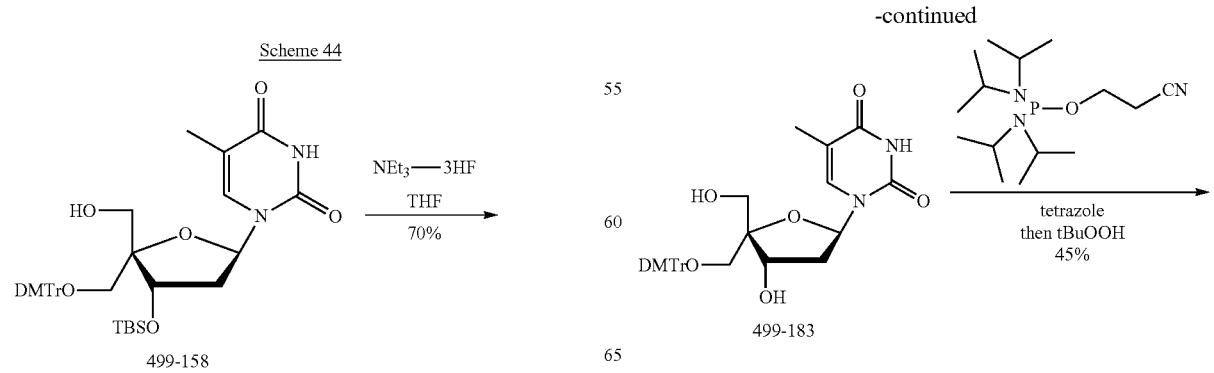

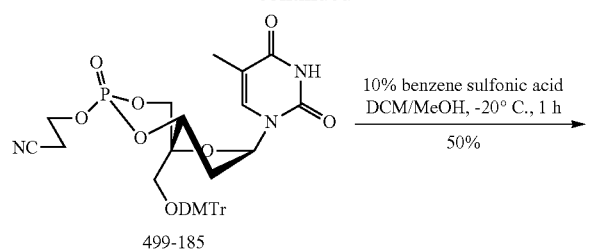
499-185
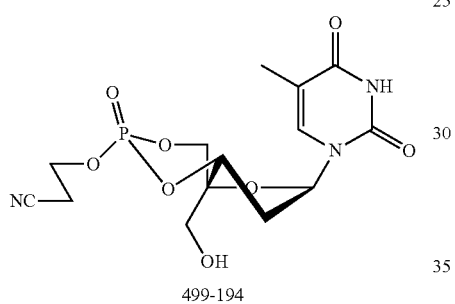
499-194
Scheme 45
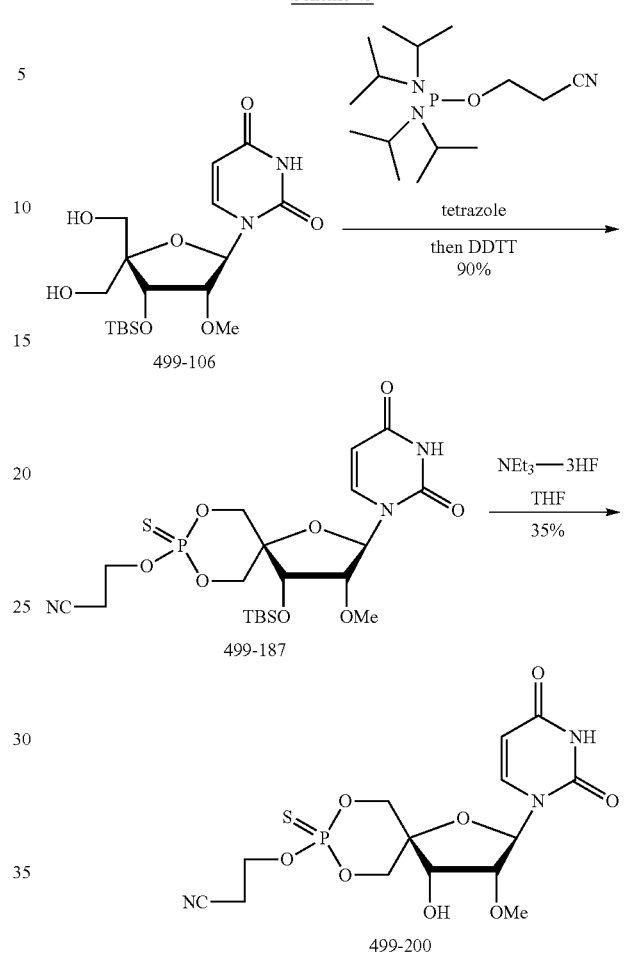
Scheme 46

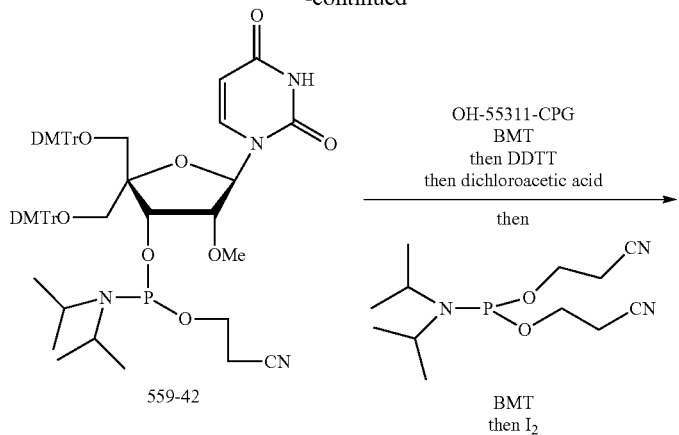
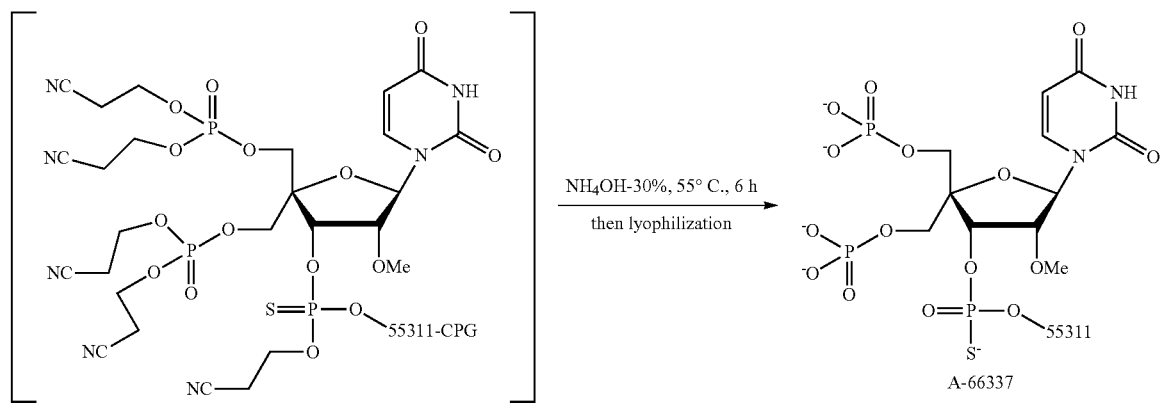
Scheme 47
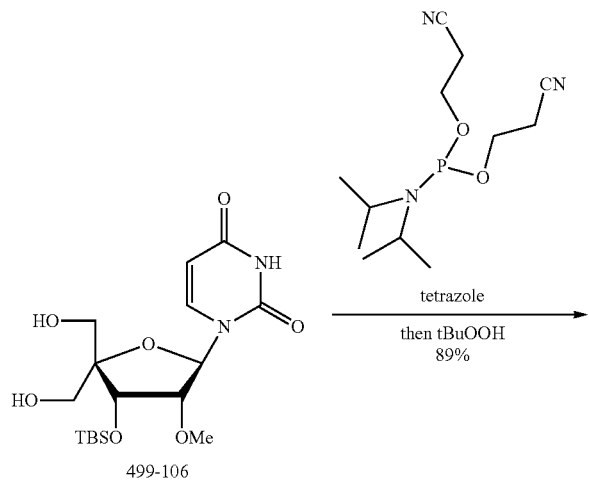

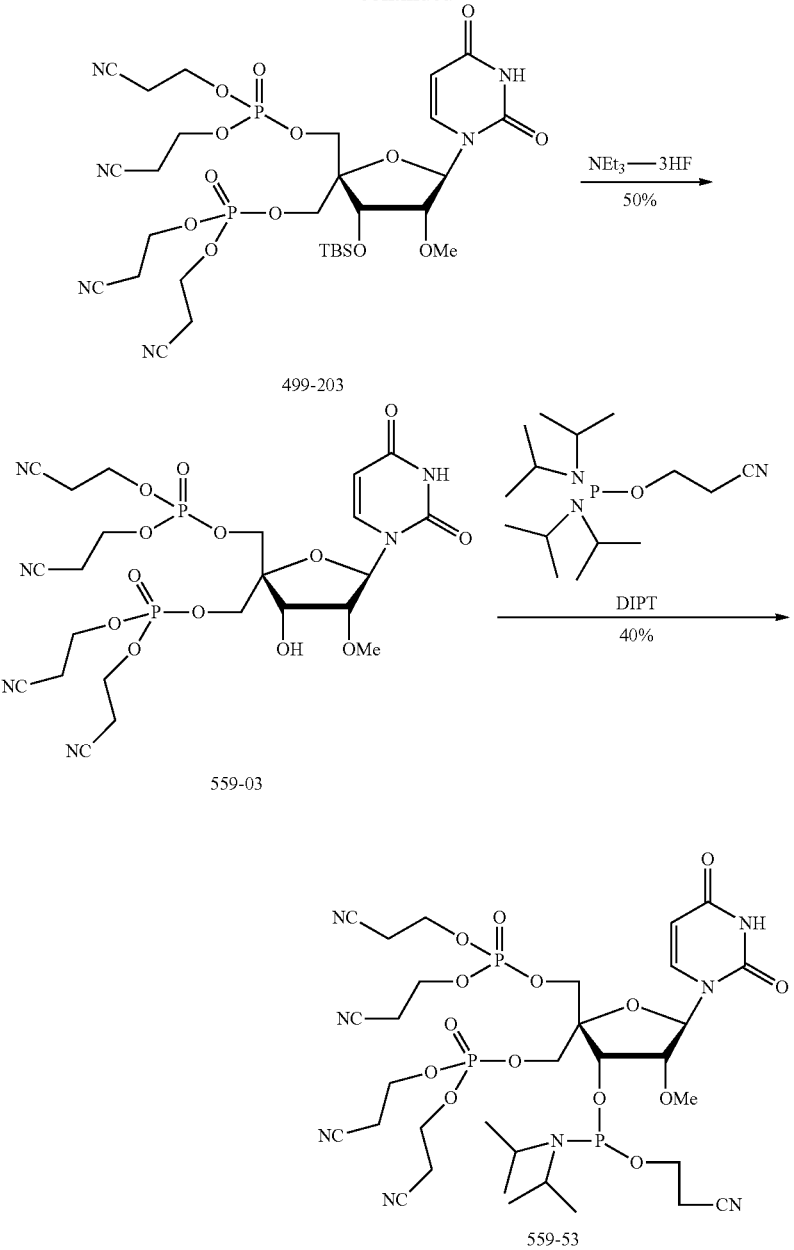
Scheme 48
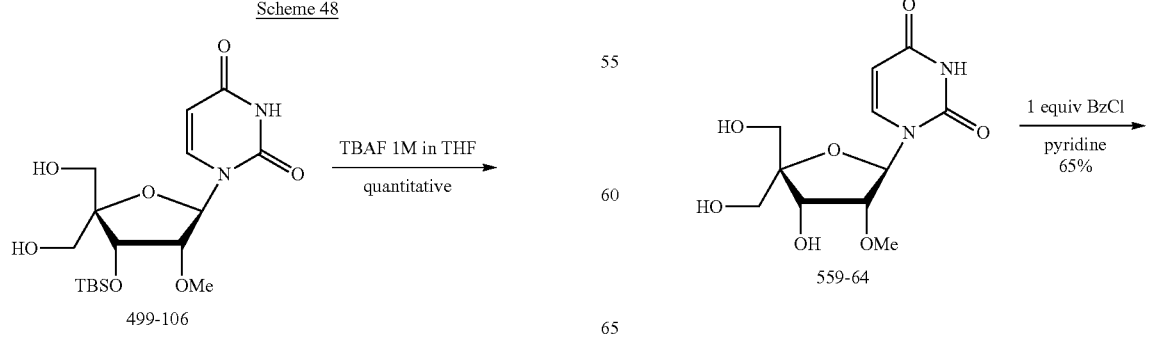

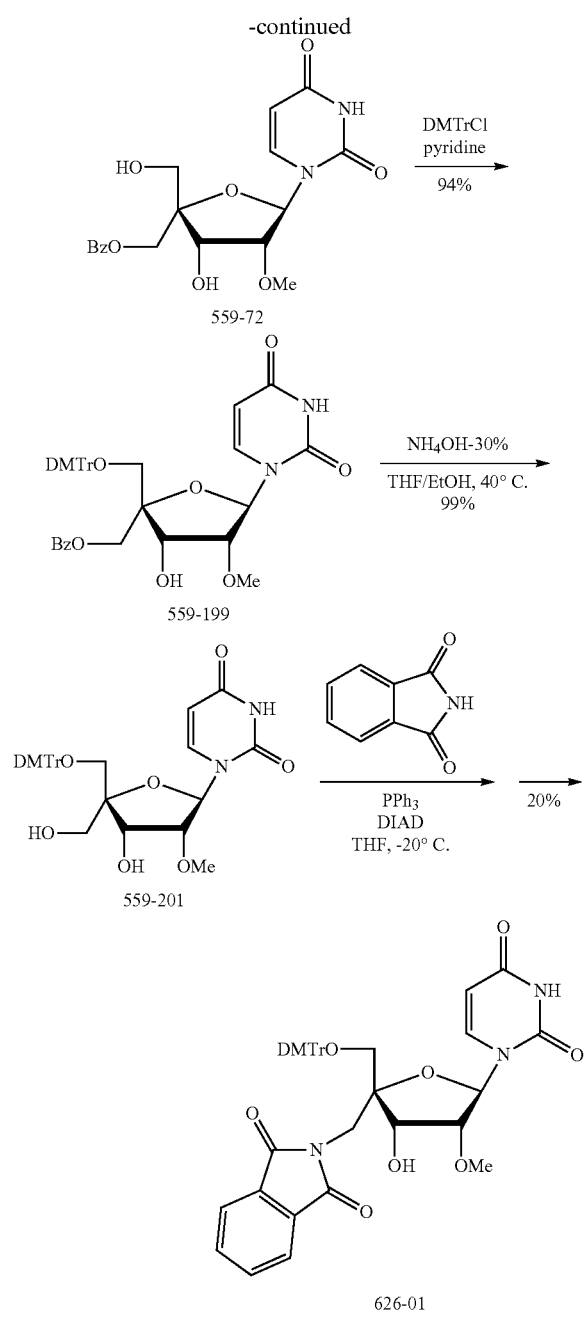

EXAMPLES

Example 1: Synthesis of 001 (Scheme 1)

Step 1 (001-1 to 001-2):

To a solution of 3'-O-tert-butyldimethylsilyl-2'-O-methyluridine (001-1) and 2-(N,N-diisopropylamino)-1,3-dithiaphospholane (prepared according to the procedure: Miller et al. *Bioorg. Med. Chem.* 2008, 16, 56-64) (1.25 equiv) in anhydrous dichloromethane is added 5-(ethylthio)tetrazole in acetonitrile (0.25 M; 1.25 equiv). The reaction mixture is stirred for 1.5 h under argon. Then DDTT (1.25 equiv) and 2,6-lutidine (1.25 equiv) are added and stirring under argon continued overnight. The mixture is evaporated and purified on silica gel to yield pure compound 001-2.

Step 2 (001-2 to 001-3):

To a mixture of compound 001-2 from Step 1 and 2-cyanoethanol (5 equiv) in acetonitrile is added DBU (1.2 equiv). After 5 min stirring at room temperature aqueous ammonia and DL-dithiothreitol (~1 equiv) are added and the mixture incubated at 45° C. for 3 h. After cooling down the mixture is treated with TRIS base and concentrated. Residue is partitioned between water and $CH_2Cl_2$. Aqueous layer is extracted with more $CH_2Cl_2$. Combined extract is dried, evaporated and purified by flash chromatography to afford pure 001-3.

Step 3 (001-3 to 001-4):

To a solution of compound 001-2 from Step 2 in THF are added 3HF-$Et_3$N (1 equiv) and $Et_3$N (2 equiv). The resulting mixture is stirred at room temperature for 1 h and filtered through a pad of silica. Filtrate is evaporated, co-evaporated with anhydrous acetonitrile and dissolved in acetonitrile. Diisopropylethylamine (2 equiv) and chloro(2-cyanoethyl) diisopropyl phosphoramidite (1.5 equiv) are added and the resulting mixture is stirred at room temperature for 2 h. After evaporation of solvents, aqueous work-up and flash chromatography purification pure phosphoramidite 001-4 is obtained.

Step 4 (001-4 to 001):

Phosphoramidite 001-4 is incorporated into ribo ON using standard automated phosphoramidite chemistry to give target 5'-dithiomonophosphate analogue 001.

Example 1a: Synthesis of 2'-mer RNA 5'-dithiophosphate A-55499 (Scheme 1a)

Example 1a is an alternative to Example 1.

0.2 M solution of 2-(N,N-diisopropylamino)-1,3-dithiaphospholane (prepared according to the procedure: Miller et al. *Bioorg. Med. Chem.* 2008, 16, 56-64) in anhydrous MeCN was used for the coupling (30 min coupling time) with 21-mer RNA on CPG employing automatic ON synthesizer. Activator was 0.25M 5-ethylthio-1H-tetrazole/MeCN. After 24 h oxidation with DDTT/Py, CPG was treated for 30 min with a mixture of 3-hydroxypropionitrile (0.5 M) and DBU (0.1 M) in MeCN, followed by 30 min treatment with a mixture of DBU and BSA (0.1 M and 0.7 M, respectively) in MeCN. Hydrolysis and cleavage from the solid support were performed by heating in conc. aq. $NH_3$/EtOH (3/1, v/v) at 50° C. for 5 h. Thus obtained modified RNA A-55499 was purified by desalting with RP-HPLC.

ES MS: 7216.7 (found), 7219.3 (calcd)

Example 2: Synthesis of 002 (Scheme 1)

The oligonucleotide 5'-trithiophosphate 002 is prepared in analogues fashion as 001 by utilizing 2-cyanoethylthiol in Step 2.

Example 3: Synthesis of 003 and 004 (Scheme 2)

5'-Deoxy-5'-mercapto-2'-O-methyluridine 3'-O-phosphoramidite 003-2 is prepared and incorporated into ribo ON according to the literature procedure (J. Matulic-Adamic et al. *Nucleosides & Nucleotides*, 1997, 16, 1933-1950). Further incorporation of bis(2-cyanoethoxy)-N,N-diisopropylaminophosphine followed by oxidizing step employing $I_2$/py/water yields 5'-deoxy-5'-thiophospahte 003. 5'-Deoxy-5'-dithiophospahte 004 is obtained by using PADS and lutidine as oxidizer.

Example 4: Synthesis of 005 and 006 (Scheme 3)

Ribo ON 5'-trihiophosphate 005 and 5'-tetrathiophosphate 006 are prepared in similar fashion as described for 003 and 004, respectively, by using bis(2-cyanoethylthio)-N,N-diisopropylaminophosphine.

Example 5: Synthesis of 007 and 008 (Scheme 4)

tert-Butyl-2-cyanoethyl-N,N-diisopropylphosphoramidite (007-1) is prepared and incorporated into 5'-ribo ON according to the literature procedure (A. Meyer et al. Tetrahedron Lett. 2006, 47, 8867-8871). Employing borane-amine complex, after acid-promoted cleavage of tert-butyl protecting group and silylation, yields 5'-boranophosphate ribo ON 007.

Thio analogue 008 is prepared in similar fashion as 007, by using tert-butyl-(2-cyanoethylthio)-N,N-diisopropylphosphoramidite (008-1).

Example 5a: Synthesis of 2'-mer RNA 5'-boranophosphate 577-152 (Scheme 4a)

Example 5a is an alternative to Example 5.

Step 1: 3'-O-(tert-Butyldimethylsilyl)-2'-O-methyluridine 5'-[bis-(1,1-dimethyl-2-cyanoethyl)-boranophosphate] (577-130)

To a solution of 3'-O-(tert-butyldimethylsilyl)-2'-O-methyluridine (550 mg, 1.48 mmol) in $CH_2Cl_2$ (10 mL) under Ar were added N,N-diisopropyl bis-(2-cyano-1,1-dimethylethyl)phosphoramidite (577-127) (605 mg, 1.25 equiv; prepared according to the procedure I. Zlatev, PhD Thesis, 2008) and 5-ethylthio-1H-tetrazole (10 mL; 0.25 M in MeCN). The resulting mixture was stirred at r. t. for 2 h. Borane-THF complex (7.5 mL, 5 equiv; 1M/THF) was added then and stirring was continued for 15 h. Mixture was concentrated to oily residue, dissolved in EtOAc (75 mL) and washed with 2% aq. $NaHCO_3$ and brine and dried ($Na_2SO_4$). Evaporated residue was purified on silica (40 g) with a gradient of MeOH (0-5%) in $CH_2Cl_2$ as an eluent to yield target compound 577-130 (430 mg, 52%) as a colorless foam.

$^{31}$P-NMR ($CD_2Cl_2$): ☐ 105.18
ESMS(-): m/z=647.2 (MHCl-1)

Step 2: 2'-O-Methyluridine 5'-[bis-(1,1-dimethyl-2-cyanoethyl)boranophosphate] (577-149)

To a solution of boranophosphate 577-130 (430 mg, 0.77 mmol) in THF was added 3HF.$Et_3$N (0.37 mL, 9 equiv) and stirred overnight at r. t. Reaction mixture was cooled to 0° C. Pyridine (1 mL) was added and then the reaction was quenched with silica. Evaporated residue was purified on silica (24 g) with a gradient of MeOH (0-10%) in $CH_2Cl_2$ as an eluent to yield target compound 577-149 (220 mg, 57%) as a white foam.

$^{31}$P-NMR ($CD_2Cl_2$): ☐ 105.31

Step 3: 5'-O—[bis-(1,1-dimethyl-2-cyanoethyl)boranophosphoryl]-2'-O-methyluridine 3'-(N,N-diisopropyl-2-cyanoethylphosphoramidite) (577-155)

To a solution of 577-149 (210 mg, 0.49 mmol) in $CH_2Cl_2$ (5 mL) under Ar were added diisopropyl-ammonium tetrazolide (127 mg, 1.5 equiv) and bis-(N,N-diisopropyl) 2-cyanoethylphosphorbisamidite (0.22 mL, 1.5 equiv). The resulting mixture was stirred at r. t. for 2 h. At this point another portion of bisamidite (0.22 mL, 1.5 equiv) was added and stirring continued for 1.5 h. Reaction mixture was filtered, concentrated and purified on silica (24 g) with a gradient of EtOAc (0-50%) in $CH_2Cl_2$ containing 1% pyridine as an eluent to yield the target phosphoramidite 577-155 (175 mg, 50%).

$^{31}$P-NMR ($CD_3CN$): ☐ 155.62, 155.35 (Rp/Sp P-amidite), 108.73 (P—$BH_3$).
ESMS(-): m/z=733.3 (MHCl-1)

Step 4: RNA 5'-boranophosphate 577-152

Phosphoramidite 577-155 (0.1 M solution in MeCN) was coupled to A-55311 on CPG using standard automated synthesis conditions with activator 5-benzylthiotetrazole (0.25M in MeCN) and oxidizer DDTT in pyridine. Solid support was treated with a mixture of DBU (0.1 M) and BSA (0.7 M) in MeCN for 40 min. prior to heating in aq. ammonia at 55° C. for 5 h. RNA 5'-boranophosphate 577-152 was purified by desalting with RP-HPLC.

MS: 7124.57 (found), 7124.88 (found)

Example 6: Synthesis of 009 (Scheme 5)

Step 1 (009-1 to 009-2):

To the mixture of 3'-O-benzyl-4'-hydroxymethyl-1',2'-β-isopropylidene-☐-D-ribofuranose (009-1) in pyridine at 0° C. is added DMTCl (1.2 equiv) and the resulting mixture stirred 2 h at room temperature. The reaction is quenched with ice-cold water and extracted with dichloromethane. Organic phase is washed with saturated aq. $NaHCO_3$, brine and dried ($Na_2SO_4$). Solvent is evaporated and residue purified on silica column. Pure product is dissolved in anhydrous DMF and NaH is added portionwise (60% in mineral oil, 1.2 equiv). Benzyl bromide (1.2 equiv) is added dropwise and the resulting mixture is stirred overnight at room temperature whereupon ice-cold water is added and the mixture extracted with EtOAc. Organic phase is dried and purified by flash chromatography. The resulting product is treated with 80% acetic acid at room temperature for 3 h, mixture evaporated and residue purified by flash chromatography to yield 3'-O-benzyl-4'-benzyloxymethyl compound 009-2.

Step 2 (009-2 to 009-3):

To an ice-cold solution of compound 009-2 and 2,6-di-tert-butyl-4-methylpyridine (1.2 equiv) in dichloromethane is added triflic anhydride (1.2 equiv) dropwise and stirred under Ar for 6 h. The reaction is quenched with cold aq. $NaHCO_3$ and extracted into dichloromethane. The organic phase is dried over MgSO4 and evaporated. Crude triflate 009-3 is used without further purification.

Step 3 (009-3 to 009-4):

To a solution of diethyl(lithiodifluotomethyl)phosphonate (prepared according to Berkowitz et al. *J. Org. Chem.* 1993, 58, 6174-6176) (3 equiv) at −78° C. in THF under Ar cold (−78° C.) triflate 009-4 in THF is added via cannula. After 1 h at −78° C. the reaction is quenched with aq. $NH_4Cl$ and diluted with EtOAc. Aqueous layer is extracted with EtOAc and combined extract dried, evaporated and purified by flash chromatography to give pure 009-4.

Step 4 (009-4 to 009-5):

Dry 009-4 is dissolved in EtOAc cooled to −15° C. and combined with cold (−15° C.) EtOAc solution of acetic anhydride, acetic acid and catalytic amount of $H_2SO_4$. After 1d at 0° C. the mixture is diluted with dichloromethane and poured into cold aq. NaHCO$_3$. Aqueous layer is extracted with dichloromethane. Combined organic extract is dried, evaporated and purified on silica gel to give pure 009-5.

Step 5 (009-5 to 009-6):

Mixture of compound 009-5, uracil (1.4 equiv) and BSA (3 equiv) in anhydrous MeCN is stirred at 80° C. under Ar for 1 h. After cooling down TMSOTf (1.5 equiv) is added, heated to 80° C. and stirred overnight under Ar. The reaction is quenched with sat. aq. NaHCO$_3$ and extracted with dichloromethane. Organic phase is dried, evaporated and purified by flash chromatography to afford nucleoside 009-6.

Step 6 (009-6 to 009-7):

Compound 009-6 is treated in MeOH with catalytic amount of K$_2$CO$_3$ for 1 h, then concentrated and residue dried by coevaporating with pyridine. Crude material is dissolved in anhydrous DMF. Imidazole (3 equiv) and TBDMSCl (2 equiv) are added and the resulting mixture stirred overnight. Aqueous work-up of the evaporated residue followed by flash chromatography purification yielded compound 009-7.

Step 7 (009-7 to 009-8):

Compound 009-7 is dissolved in ethanol and treated with 10% Pd/C under hydrogen atmosphere for 6 h. The mixture if filtered through a pad of Celite and filtrate concentrated. The evaporated residue is treated with methanolic ammonia for 1 h and then concentrated. Flash chromatography of evaporated residue yields pure compound 009-8.

Step 8 (009-8 to 009-9):

A mixture of triethylammonium salt of 009-8 in anhydrous pyridine and 1-(2,4,6-trimethylphenyl-3-nitro)-1,2,4-triazole (MSNT) (2 equiv) is stirred at 90° C. for 2 h. The mixture is cooled down, diluted with EtOAc and washed with sat. aq. NaHCO$_3$. The organic layer is dried, concentrated and purified by flash chromatography to yield Rp/Sp mixture 009-9.

Step 9 (009-9 to 009-10):

Nucleoside 009-9 is dissolved in a mixture of anhydrous dichloromethane and DIPEA and chloro-(2-cyanoethyl)-N, N-diisopropylphosphoramidite (2 equiv) is added. After 1 h at room temperature, the reaction is quenched with MeOH and the mixture diluted with EtOAc, washed with sat. aq. NaHCO$_3$, brine, dried and evaporated. Purification of the residue on silica column yields amidite 009-10 as mixture of 4 compounds.

Step 10 (009-10 to 009):

Phosphoramidite 009-10 is incorporated into ribo ON using standard automated phosphoramidite chemistry to give target 5'-dithiomonophosphate analogue 009.

Example 7a: Synthesis of 010 (Scheme 6)

Step 1 (009-1 to 010-2):

Starting from modified carbohydrate 010-1 (Waga et al. *Biosci. Biotech. Biochem.* 1993, 57, 1433-8) and following the procedure described in Example 9, Step 4, the compound 010-2 is prepared.

Step 2 (010-2 to 010-3):

Starting from compound 010-2 and following the procedure described in

Example 7b

Step 5, the compound 010-3 is prepared.

Step 3 (010-3 to 010-4):

Starting from compound 010-3 and following the procedure described in

Example 7c

Step 6, the compound 010-4 is prepared.

Step 4 (010-4 to 010-5):

Compound 010-4 is dissolved in ethanol and treated with 10% Pd/C under hydrogen atmosphere for 6 h. The mixture if filtered through a pad of Celite and filtrate concentrated. Silica gel purification of evaporated residue yields pure diol 010-5.

Step 5 (010-5 to 010-6):

To a solution of 010-5 in DMF imidazole (3 equiv) and TBDMSCl (2 equiv) are added and the resulting mixture stirred overnight. Aqueous work-up of the evaporated residue followed by flash chromatography purification yielded compound 010-6.

Step 6 (010-6 to 010-7):

Nucleoside 010-6 is dissolved in a mixture of anhydrous dichloromethane and DIPEA and chloro-(2-cyanoethyl)-N, N-diisopropylphosphoramidite (2 equiv) is added. After 3 h at room temperature, the reaction is quenched with MeOH and the mixture diluted with EtOAc, washed with sat. aq. NaHCO$_3$, brine, dried and evaporated. Purification of the residue on silica column yields amidites 010-7.

Step 7 (010-7 to 010-8):

Phosphoramidite 010-7 is incorporated into ribo ON and 5'-O-DMT cleaved by using standard automated phosphoramidite chemistry.

Step 8 (010-8 to 010-10):

Ribo ON 010-8 is converted into 5'-monophosphate and -monophosphate analogues 010-10 via H-phosphonate 010-9 by following literature conditions (A. Meyer et al. *Tetrahedron Lett.* 2006, 47, 8867-8871).

Example 8: Synthesis of 011 (Scheme 7)

Standard conditions are used to incorporate 4'-hydroxyethyluridine analogue 011-1 into ribo ON-5' end and to convert it into 4'-ethyl phosphate, thiophosphate, amide and borane esters; as described in Example 010, Steps 6-10.

Example 9: Synthesis of 012 (Scheme 8)

Step 1 (009-1 to 015-1):

To a solution of nucleoside 009-1 in pyridine is added TrCl (1.5 equiv) and the mixture stirred overnight at room temperature. Pyridine is evaporated and the residue partitioned between dichloromethane and water. Organic layer is washed with sat. aq. NaHCO$_3$, water, brine and dried. Flash chromatography purification affords alcohol 015-1.

Step 2 (015-1 to 015-3):

Starting from compound 015-1 and applying conditions from Example 9, Steps 2 and 3, compound 015-3 is prepared.

Step 3 (015-3 to 015-4):

Treatment of protected sugar 015-4 with 80% TFA in dichloromethane for 2 h yielded target alcohol 014-4 after evaporation of reaction mixture, aq. NaHCO$_3$, work-up and flash chromatography purification.

Step 4 (015-4 to 015-9):

Compound 015-4 is converted into nucleoside 015-9 by following conditions from Example 9, Steps 2 to 6.

Step 5 (015-9 to 015-10):

Compound 015-9 is dissolved in EtOH and treated with 10% Pd/C under the atmosphere of H$_2$. After 3 h the mixture is filtered and filtrate evaporated. Crude compound is purified on silica column.

Step 6 (015-10 to 015-11):
Phosphoramidite 015-11 is prepared from compound 015-10 using condition as described in Example 9, Step 9.

Step 7 (015-11 to 15):
Phosphoramidite 015-11 is incorporated into ribo RNA 5'-end using standard automated RNA synthesis chemistry. Extra TMSBr/MeCN deprotection step is included for efficient removal 5'-phosphate ethyl ester groups.

Example 10: Synthesis of 016 (Scheme 9)

Standard chemistry used in the preparation of Examples 10-12 is also used in making modified ribo-ON 016 starting from modified ribose 016-1 (prepared by literature procedure Waga et al. *Biosci. Biotech. Biochem.* 1993, 57, 1433-8).

Example 11: Synthesis of 017 (Scheme 10)

Step 1 (017-1 to 017-2):
Modified 4'-hydroxymethyluridine 017-1 is dissolved in mixture of dichloromethane and DIPEA and chloro-(2-cyanoethyl)-N,N-diisopropylphosphoramidite (3 equiv) is added. After 6 h at room temperature, the reaction is quenched with MeOH and the mixture diluted with EtOAc, washed with sat. aq. NaHCO$_3$, brine, dried and evaporated. Purification of the residue on silica column yields amidites 017-1.

Step 2 (017-2 to 017-4):
Phosphoramidite 017-2 and diethyl-2-hydroxyethylphosphonate (3 equiv) are coevaporated several times with anhydrous acetonitrile and dissolved in acetonitrile. To this solution 5-benzyltetrazole (5 equiv) is added under argon and the mixture stirred at room temperature for 3 h. At this time I$_2$/pyridine/water oxidizing solution is added. After 12 h the mixture is concentrated and purified by flash chromatography to yield phosphate 017-4.

Step 3 (017-4 to 017-5):
Phosphate 017-4 is dissolved in ethyl acetate and treated with 10% Pd/C under H$_2$ atmosphere for 6 h. The mixture is filtered through a pad of Celite, evaporated and used as such for further transformation into 3'-phosphoramidite.

Step 4 (017-5 to 017-6):
Alkohol 017-5 is converted into the corresponding 3'-phosphoramidite 017-6 following the procedure described in Step 1 of this example.

Step 5 (017-6 to 017):
Phosphoramidite 017-6 is incorporated into ribo-ON 5'-end by standard automated RNA synthesis chemistry. Phosphate ethyl protecting groups are cleaved with TMSBr/MeCN to afford after employing standard deprotection conditions modified ribo ON 017.

Example 12. Synthesis of 018 (Scheme 11)

5'-Deprotected ON 017-8 on solid support (Example 14, Step 7) is coupled with tert-butyl-2-cyanoethyl-N,N-diisopropylphosphoramidite (007-1, Scheme 4) and then product 018-1 converted to H-phosphonate analogue 018-2 according to the literature procedure (A. Meyer et al. *Tetrahedron Lett.* 2006, 47, 8867-8871). Further oxidation with I$_2$/py/water followed by deprotection yields 5'-phosphate ribo ON analogue 018a. Thiophosphate, phosphoamidate and boranophosphate analogues 018a, 018b and 018c, respectively, are made in similar fashion.

Example 13: Synthesis of 019 (Scheme 12)

Step 1 (019-1 to 019-2):
To a solution of diethyl(2-hydroxyethyl)phosphate (019-1) in dichlomethane/DIPEA mixture at 0° C. is added chloro(2-cyanoethyl)-N,N-diisopropylaminophosphoramidite. The resulting mixture is stirred under argon at room temperature for 2 h, filtered into aq. TRIS buffer (ph 7.0) and diluted with dichloromethane. Organic layer is washed with more buffer, dried and evaporated and purified on silica to afford target phosphoramidite 019-2.

Step 2 (019-2 to 019-3):
Phosphoramidate 019-2 is incorporated into RNA by standard automated RNA synthesis chemistry. Further standard oxidation and deprotection yield ethylenediphosphate 019a, ethylenethiophosphate 019b, phosphoramidate 019c and boranophosphate analogue 019d.

Example 14: Synthesis of 020 (Scheme 13)

Step 1:
To a solution of O-(dimethoxytrityl)ethylenediol in dichloromethane/DIPEA mixture under argon at 0° C. is added dropwise chloro(2-cyanoethyl)-N,N-diisopropylaminophosphoramidite. The reaction mixture is stirred at room temperature for 2 h, then filtered into aq. TRIS buffer (ph 7.0) and diluted with dichloromethane. Organic layer is washed with more buffer, dried, evaporated and purified on silica to afford target phosphoramidite 020-1.

Step 2 (020-1 to 020-4):
Phosphoramidate 020-1 is incorporated into ribo ON by standard automated RNA synthesis chemistry. Phosphite 020-2 is further oxidized to monophosphate analogue 020-3 which is detritylated for next coupling with phosphoramidite 020-1.

Step 3 (020-4 to 020):
By repeating Steps 2 to 4 another 2-hydroxyethylphosphate moiety is introduced thus yielding, after standard deprotection and cleavage from the solid support ethylenediphosphate 020.

Examples 13a: A-59258, A-59259, A-59427, A-59429, A-59428, A-59430, A-59260, A-59261, A-59262, A-59263 (Scheme 12a)

Example 13a is an alternative to Examples 12 and 13.

Step 1: N,N-diisopropyl-2-cyanoethyl-2-(dimethoxytrityloxy)ethylphosphoramidite (487-197)

A solution of O-(dimethoxytrityl)ethylenediol (2.75 g, 7.5 mmol) in CH$_2$Cl$_2$ (25 mL), DIPEA (5.2 mL, 4 equiv.) and N,N-diisopropyl chloro(2-cyanoethyl)phosphoramidite (2.5 mL, 1.5 equiv) was stirred at r. t. for 1 h. At this point the reaction was quenched with MeOH (0.5 mL). The resulting mixture was diluted with CH$_2$Cl$_2$ (100 mL), washed with 2% aq. NaHCO$_3$, brine and dried (Na$_2$SO$_4$). Evaporated residue was purified on silica (80 g) with a gradient of EtOAc (0-50%) in hexanes containing 0.5% Et$_3$N to afford target phosphoramidite 487-197 (2.12 g, 54%) as a colorless viscous oil.

$^{31}$P-NMR (CDCl$_3$): δ 148.75 (Rp/Sp)

Synthesis of A-59258, A-59259, A-59427, A-59429, A-59428, A-59430, A-59260, A-59261, A-59262, A-59263

Phosphoramidite 487-197 (0.2 M in MeCN/CH$_2$Cl$_2$, 1/1) was incorporated onto 21-mer A-55331 on CPG by standard automated RNA synthesis chemistry to yield A-59258 with I$_2$ as an oxidizer and A-59259 with DDTT in pyridine. Second phosphate moiety was introduced by using Chemical Phosphorylation Reagent from Glen Research thus yielding A-59427, A-59429, A-59428, and A-59430. By two consecutive couplings of phosphoramidite 487-197 5'-phosphate analogues A-59260, A-59261, A-59262, and A-59263 were isolated. Oligonucleotides were deprotected using standard conditions and purified by desalting with RP-HPLC.

A-59258
ES MS: 7169.68 (found), 7173.15 (calcd)

A-59259
ES MS: 7185.85 (found), 7189.21 (calcd)

A-59427
ES MS: 7250.77 (found), 7254.13 (calcd)

A-59429
ES MS: 7267.48 (found), 7270.2 (calcd)

A-59428
ES MS: 7266.66 (found), 7270.2 (calcd)

A-59430
ES MS: 7282.70 (found), 7286.26 (calcd)

A-59260
ES MS: 7297.79 (found), 7298.19 (calcd)

A-59261
ES MS: 7309.85 (found), 7314.25 (calcd)

A-59262
ES MS: 7309.86 (found), 7314.25 (calcd)

A-59263
ES MS: 7325.89 (found), 7330.32 (calcd)

Example 15: Synthesis of 021 (Scheme 14)

4'-Hydroxymethyl 3'-phosphoramidite analogue 021-1 is converted into di(ethylphosphate) ribo ON 021 in similar fashion as described for 020 in Example 17.

Example 16: Synthesis of 022 (Scheme 15)

Dimethylamino analogue 022 is prepared in a similar way as compound 022, Example 18.

Example 17: Synthesis of 023 (Scheme 16)

Step 1 (023-2 to 023-3):
5-Deoxy-ribo-phosphonate diester 023-2 (prepared according to *Collect. Czech. Chem. Commun.* 1989, 54, 1055-1066) is converted into monoester 023-3 by treatment with aq. NH$_3$ in methanol. Reaction mixture is evaporated and crude product used in the next step.

Step 2 (023-3 to 023-4):
Monoester 023-3 is dried by coevaporating with acetonitrile and dissolved in THF/DIPEA mixture. 2-Chloroethylphosphate triester 023-1 is added at 0° C. under argon and the reaction mixture stirred at room temperature. Solid is filtered, filtrate evaporated and, after aqueous work-up, purified on silica gel to yield ethylenediphoshate 023-4.

Step 3 (023-4 to 023-7):
By applying chemistry as described in Example 9, Steps 4 to 6, aglicone 023-4 is converted into modified nucleotide 023-7.

Step 4 (023-7 to 023):
By applying chemistry as described in Example 12, Steps 9 to 12, is nucleotide 023-7 incorporated into ribo-ON thus yielding ribo-ON 5'-phosphate mimic 023.

Example 18: Synthesis of 024 (Scheme 17)

Example 19: Synthesis of 025 (Scheme 18)

Example 20. Synthesis of Compound 12

Step 1:
Synthesis of 2 (Scheme 1): To a solution of 5'-O-dimethoxytrityl-2'-O-methyluridine (1) in anhydrous pyridine are added TBDMSCl (2 equiv) and imidazole (2 equiv). The reaction mixture is stirred overnight under argon. After completion, MeOH is added, and then the mixture is diluted with ethyl acetate and washed twice with saturated bicarbonate solution. The organics are dried and evaporated to dryness. The crude mixture is then diluted with dichloromethane and methanol (7:3) and cooled to −20° C. Benzenesulfonic acid (10% solution in DCM/MeOH) is added dropwise to the mixture for 1 h. The mixture is then stirred for 30 min at −20° C. Saturated bicarbonate solution is added, and then the mixture is extracted and washed twice more with bicarbonate. The organics are dried and evaporated to dryness. The crude compound is purified by flash chromatography.

Step 2:
Synthesis of 3 (Scheme 1): To a solution of 2 in anhydrous DMSO are added DCC and DCA. The mixture is stirred under argon overnight. Then oxalic acid is added dropwise for 1 h at 0° C. The mixture is diluted with ethyl acetate, stirred at 0° C. and filtered under a bed of Celite. The filtrates are recovered and washed with bicarbonate and brine. The organics are dried and evaporated to dryness. The crude residue is dissolved in dioxane and formaldenyde is added. The solution is stirred at 0° C. and then 1 N NaOH solution is added dropwise. The mixture is stirred overnight at room temperature. Formic acid is then added until neutrality. The mixture is diluted with DCM and washed with bicarbonate and brine. The aqueous layers are back extracted with ethyl acetate. The organics are collected, dried and evaporated. The crude is purified on silica gel flash chromatography affording pure compound 3 as white foam.

Step 3:
Synthesis of 4 (Scheme 1): DMTrCl (1.1 equiv) is added to a solution of compound 3 in dry pyridine. The mixture is stirred under argon for 1 h, then diluted with DCM, and washed twice with bicarbonate. After purification of the concentrated organics by silica gel chromatography, pure 4 is obtained as white foam.

Step 4:
Synthesis of 5 (Scheme 1): Sodium hydride (1.1 equiv) is added to a solution of compound 4 in anhydrous THF. BnCl is added (2 equiv) and the mixture is stirred for 2 h. The mixture is diluted with brine and ethyl acetate. After extraction, the organics are dried and evaporated to dryness. The crude residue is then treated with benzene sulfonic aced at −20° C. as described for compound 2. After purification, compound 5 is obtained as white foam.

Synthesis of 10 (Scheme 1): Compound 5 is treated with DMSO, DCC and DCA as described for compound 3. After work-up and purification, the corresponding aldehyde 10 is obtained as white foam.

Step 5:
Synthesis of 11 (Scheme 1): Aldehyde 10 is dissolved in anhydrous THF, then methyl phosphorous glide is added at −78° C. and the reaction mixture is stirred for 2 h. The mixture is diluted with ethyl acetate and washed with saturated ammonium chloride solution. The organics are dried and evaporated, then purified by silica gel chromatography affording pure 11.

Step 6:

Synthesis of 12 (Scheme 1): Compound 11 is dissolved in dioxane and 9-BBN (2 equiv) is added. The mixture is stirred overnight at room temperature. NaOH in $H_2O_2$ is added and the stirring is continued for 12 more hours. After completion of the reaction the mixture is diluted with ethyl acetate and washed with saturated ammonium chloride solution. The organic layers are dried and evaporated to dryness. The crude residue is dried by azeotropic distillation with anhydrous pyridine, then dissolved in pyridine and DMTrCl (2 equiv) is added. The mixture is stirred under argon for 2 hours, diluted with DCM and washed with saturated bicarbonate solution. The organics are collected, dried and evaporated to dryness. The crude compound is purified on silica gel, affording pure 12.

Example 21. Synthesis of Compound 22

Synthesis of 22 (Scheme 2): Compound 5 is dissolved in dry THF and 4 equiv of 1,1'-thiocarbonyldiimidazole are added. The mixture is stirred for 2 h under argon. After completion the solvents are evaporated to dryness. The residue is dissolved in dry dioxane and refluxed. 2 equiv of n-$Bu_3$SnH are added on small portions through 2 h addition under reflux. After chilling to room temperature, the mixture is diluted with ethyl acetate and extracted twice with brine. The organics are evaporated and the residue is purified on silica gel, affording pure 22.

Example 22. Synthesis of Compound 23

Catalytic hydrogenation of 11 in the presence of Pd—C followed by benzylation with Bn—Cl and NaH affords compound 23.

Example 23. Syntheses of Compounds 25 and 26

Step 1:

Synthesis of 24 (Scheme 2): Compound 18 (mixture of E and Z isomers) is dissolved in absolute ethanol and Pd/C is added. The mixture is stirred overnight under hydrogen atmosphere. The catalyst is filtered under bed of Celite. The filtrates are evaporated to dryness and then dissolved in anhydrous THF. The mixture is treated with BnCl and NaH as described for compound 5. Pure amine 24 is obtained after silica gel chromatography.

Step 2:

Synthesis of 25 (Scheme 2): Protection of compound 24 is performed after treating with trifluoroacetic anhydride (2 equiv) at room temperature for 4 h. The reaction is quenched by adding saturated bicarbonate solution. Pure 25 is obtained after extraction and silica gel chromatography.

Step 3:

Synthesis of 26 (Scheme 2): To a solution of compound 24 in anhydrous THF is added mono TFA protected thiourea. The mixture is stirred under reflux overnight, then diluted with ethyl acetate and washed with brine. Organics are dried and evaporated to dryness. The crude is purified by silica gel flash chromatography affording pure 26.

Example 24. Syntheses of Compounds 47 and 48

Step 1:

Synthesis of 45 and 46 (Scheme 3): Compounds 4, 27-43 are dried by azeotropic distillation with anhydrous acetonitrile and dissolved in dry acetonitrile. 1H tetrazole (2.5 equiv) and bis-cianoethyl-di-isopropyl phosphoramidite (1.5 equiv) are added and the mixture is stirred for 2 h at room temperature. For compounds 46: Iodine solution in water/pyridine is added and the mixture is stirred for 1 more h. For compound 45: Sulfur solution in THF/pyridine is added and the mixture is stirred for 2 hours. For both types of compounds: The mixture is diluted with ethyl acetate and washed with brine. The aqueous layers are back extracted with ethyl acetate; the organics are collected, dried and evaporated to dryness. The crude compounds are purified on flash chromatography affording pure 45 or 46 respectively.

Step 2:

Synthesis of 47 and 48 (Scheme 3): Compounds 45 and 48 respectively are dissolved in dry THF and the HF-$NEt_3$ complex (2 equiv) is added. The mixture is stirred for 30 min at room temperature. 2 equiv of $NEt_3$ are then added, the mixture is stirred for 30 more minutes and then the solvents are evaporated to dryness. The residue is filtered on a bed of silica gel and evaporated to dryness, then dried by azeotropic distillation with anhydrous acetonitrile. To a solution of each compound in dry acetonitrile are added 1H tetrazole (2.5 equiv) and chloro-cianoethyl-di-isopropyl phosphoramidite (1.5 equiv) and the mixtures are stirred for 2 h at room temperature. Pure phosphoramidites 47 and 48 are obtained after aqueous work-up and flash chromatography purification.

Example 25. Synthesis of Oligonucleotides (ON) Using Amidites 47 and 48

Pure and dry phosphoramidites 47 and 48 are incorporated into ONs 49 and 50 respectively using standard automated phosphoramidite oligonucleotide synthesis on solid support. (Matteucci and Caruthers, *J. Am. Chem. Soc.,* 1981, 103, 3185)

Example 26. Synthesis of ON 54

Step 1:

Synthesis of compound 53 (Scheme 4): Compounds 4, 27-43 are reacted with cyanoethyl-di-isopropyl-phosphorobis-amidite (1.5 equiv) and tetrazole (2.5 equiv) in anhydrous acetonitrile. After rapid aqueous work-up and filtration on silica gel, the resulting compound 51 is treated with tetrazole (2.5 equiv) and hydrogen sulfide (1 M solution in anhydrous dioxane). After aqueous work-up, the resulting hydrogenophosphonothioate diesters 52 are obtained. These compounds are subsequently oxidized with sulfur, and treated with HF-TEA and the chlorophosphoramidite, as described for compound 45.

Step 2:

Synthesis of ON 54: Phosphoramidite 53 (Scheme 4) is readily incorporated into ON 54 using standard automated oligonucleotide phosphoramidite synthesis cycles.

Example 27. Synthesis of ON 58

Starting from compounds 4, 27-43 (Scheme 4), phosphitylation with S,S-bis-cyanoethyl-di-isopropylphosphor-dithio-amidite and tetrazole is performed, affording compound 55. After oxidation using elemental sulfur, as described for compound 45, work-up and purification, compounds 56 are obtained. Subsequent removal of the TBDMS group, introduction of the 3' phosphoramidite and incorporation into ON 58 is performed as described for compound 45.

Example 28. Synthesis of ONs 63, 67, 71 and 74

Step 1.
Synthesis of 59 (Scheme 5): Compounds 4, 27-43 are first treated with p-toluenesulfonyl chloride (1.5 equiv) in dry pyridine. After aqueous work-up, the crude mixtures are dissolved in dry dioxane and hexamethyldisilathiane (HMDST, 3 equiv) is added. The reaction mixture is stirred for 3 h at room temperature. The corresponding 5'-thiolo nucleosides (59) are obtained after work-up and purification.
Step 2.
Synthesis of ONs 63, 67, 71 and 74: Starting from compounds 59, oligonucleotides 63 and 67 can be readily obtained using the depicted in Scheme 5 reactions, and oligonucleotides 71 and 74, those depicted in Scheme 6, all according to the general conditions previously described.

Example 29. Syntheses of ONs 78, 83 and 84

Synthesis of ON 78 (Scheme 7A): Compound 3 (Scheme 7A) is dissolved in dry acetonitrile, tetrazole (2.5 equiv) and cyanoethyl-di-isopropyl-phosphoro-bis-amidite (1.5 equiv) are added and the mixture is stirred under argon for 2 hours. Iodine solution is then added (as previously described). After rapid aqueous work-up and filtration on silica gel, the solvents are evaporated to dryness and the compound is treated with HF-TEA. The 2'-O-TBDMS isomers are separated and subjected to the 3' phosphitylation using chloro phosphoramidite according to previously established protocol. After silica gel chromatography purification, phosphporamidite building block 77 is incorporated into ON 78 using the standard automated procedure.
Synthesis of ONs 83 and 84 (Scheme 7A): Compound 3 is dissolved in dry acetonitrile, tetrazole (2.5 equiv) and 1.5 equiv of: S-cyanoethyl-di-isopropyl-phosphorothio-bis-amidite (for compound 80, X=S) or cyanoethyl-di-isopropyl-phosphoro-bis-amidite (for compound 79, X=O) respectively, are added and the mixture is stirred under argon for 2 hours, leading to corresponding phosphite triester compounds 75 (Scheme 7A). Each compound is then oxidized with elemental sulfur, as previously described, leading to phosphoro(di)thionate compounds 79 (X=O) and 80 (X=S). Each one of them is treated with HF-TEA, the 2'-O-TBDMS isomer is recovered pure in each case and subjected to 3'-O-phosphitylation, affording compounds 81 and 81 (Scheme 7A). Each one of them can be readily incorporated into ON 83 and 84 respectively using the standard synthesis procedures.

Example 30. Syntheses of ONs 91, 92 and 95

Synthesis of ONs 91, 92 and 95 (Scheme 7B): After deprotection of the benzyl and DMT groups of compound 12, the corresponding homo diol (85) is treated in a similar manner as its analogue diol 3, as depicted in Scheme 7A, leading to ONs 91, 92 and 95 after incorporation using automated solid support synthesis.

Example 31. Syntheses of ONs 102, 103, 106, 113, 114 and 117

Synthesis of ONs 102-3, 106, 113-4 and 117 (Schemes 8A and 8B): 4',5' diol 3 and his 4'-homo analog 85 are reacted with 3 equiv of p-toluenesulfonyl chloride in dry pyridine. After 2 h of stirring at room temperature, the mixture is diluted with ethyl acetate and neutralized by adding saturated bicarbonate solution. The bi-layer mixture is separated and the organics are washed with saturated bicarbonate, dried and evaporated to dryness. After azeotropic drying with anhydrous acetoitryle, the residue is dissolved in dry dioxane and HMDST (6 equiv) is added. The corresponding di-thiols (96) and (107) are obtained after aqueous work-up and silica gel chromatography. They are readily converted to the corresponding 3' phosphoramidites 100-1, 106, 111-2, 116, exhibiting the desired cyclic thiolophosphate moiety (Schemes 8A and 8B) according to the previously described phosphitylation-cyclization-oxidation schemes. These 3' phosphoramidite building blocks are used in ON synthesis, affording the target RNA oligomers.

Example 32. Syntheses of ONs 124, 125, 128, 135, 136 and 139

The monomer mono-thiols 118 and 129 (Schemes 9A and 9B) are obtained after tosyl activation/sulfide displacement sequences using the mono-protected diols 4 and 5 respectively, according to previously described procedure, using 1.5 equiv of TsCl and 3 equiv of HMDST. The corresponding phosphitylation/cyclization/oxidation and then 3'-deprotection/3'-phospitylation are performed in a similar manner as described in Schemes 8A and 8B for the di-thiolo analogues. Incorporation of the target 3'-phosphoramidites 122-3, 127, 133-4, 138 into the corresponding ONs is performed using standard oligonucleotide synthesis.

Example 33. Syntheses of Compounds 140 and 147

The target 6 and 7-membered ring H-phosphonate diesters 140 and 147 (Schemes 10A and 10B) respectively, are obtained from the corresponding diols 3 and 85, after cyclization using diphenyl phosphite. Each starting diol is dried by azeotropic distillation with dry pyridine, and then dissolved in pyridine. 10 equiv of diphenyl phosphite are added and the mixture is stirred overnight under argon. The reaction mixture is diluted with dichloromethane and washed twice with saturated bicarbonate. The target cyclic H-phosphonate diesters 140 and 147 are obtained after purification by silica gel flash chromatography.

Example 34. Syntheses of Compounds 185 and 93

The target 6 and 7-membered ring H-phosphonothioate diesters 185 and 193 respectively, are obtained from the corresponding diols 3 and 85, after cyclization using diphenyl thiophosphite, in a similar manner as the corresponding cyclic H-phosphonates (Schemes 10A and 10B). Each starting diol is dried by azeotropic distillation with dry pyridine, and then dissolved in pyridine. 10 equiv of diphenyl thiophosphite are added and the mixture is stirred overnight under argon. The reaction mixture is diluted with dichloromethane and washed twice with saturated bicarbonate. The target cyclic H-phosphonothioate diesters 185 and 193 are obtained after purification by silica gel flash chromatography.

Example 35. Syntheses of ONs 143, 146, 150, 153, 191, 192, 196, 199

Cyclic H-phosphonates 140 and 147, and their phosphonothioate analogues 185 and 193 are readily oxidized by anhydrous carbon tetrachloride in presence of either borane, leading to the corresponding borano(thio)phosphates 141, 148, 186 and 194; or ammonia or primary amines, leading to the corresponding phosphor(thio)amidates 144, 151, 187 and 197. These compounds are subjected to the previously established 3'-deprotection/3'-phosphitylation procedures, affording the corresponding 3'-phosphoramidite building blocks, which are further incorporated into the target RNA oligonucleotides using the standard oligonucleotide synthesis procedures.

Example 36. Syntheses of ONs 302 and 305

Oligonucleotides exhibiting 5' terminal cyclic phosphoramidate monoesters are obtained starting from the appropriate C-4'-branched azido or amino alkyl monomers 8 and 24 respectively (Schemes 13A-B). After removal of the 5'-O-benzyl protection and/or concomitant reduction, the resulting crude intermediates are reacted with diphenyl phosphite in anhydrous pyridine for 1 h, and then hydrolyzed by adding water/triethylamine and stirring for 30 min. The reaction mixtures are washed twice with bicarbonate and the crudes are purified by silica gel chromatography. The corresponding 5'-H-phosphonate monoesters (200 and 303) are dissolved in a mixture of dry acetonitrile and trimethylsilyl chloride Anhydrous $CCl_4$ (25 equiv) is then added and to the mixture is stirred for 4 hours at room temperature. The solvents are evaporated to dryness and coevaporated three times with dry acetonitrile. The typical 3'-deprotection/3'-phosphitylation steps are then performed as previously described and then the pure and dried 3'-phosphoramidite building blocks 301 and 304 are incorporated into the target oligonucleotides using standard oligonucleotide synthesis.

Example 37. Syntheses of ONs 309 and 312

Oligonucleotides exhibiting 5' terminal cyclic phosphonate moieties are prepared starting from the appropriate 5'-O-benzyl protected 4'-C-hydroxyalkyl nucleosides 5 and 307. In the first step, bromination of the primary hydroxyl group is performed using triphenylphosphine (2 equiv) and bromine (5 equiv). After aqueous work-up, the crudes are treated with 2,3-dichloro-5,6-dicyanobenzoquinone (DDQ, 3 equiv), and after work-up, purification on silica gel chromatography affords nucleosides 306 and 310, which are further reacted with O-benzyl-β-cyanoethyl-di-isopropyl-phosphoramidite (1.5 equiv) in presence of tetrazole (2.5 equiv), in anhydrous acetonitrile. The resulting crude 5' phosphite triesters are heated for 24 hours in refluxing acetonitrile affording the cyclic phosphonates according to the Arbuzov reaction. The latter are worked-up, and subjected to the typical 3'-deprotection/3'-phosphitylation procedure. The resulting building blocks 308 and 311 are readily incorporated into the target oligonucleotides using standard oligonucleotide synthesis.

Example 38. Syntheses of ON 320

The various 4'-C-branched compounds 4, 27-43 are transformed to the corresponding 5' O-aryl amino acid phosphoramidate conjugates (318) according to the procedures described by McGuigan et al. (*J. Med. Chem.*, 2006, 49, 452). The previously described 3'-deprotection/3'-phosphitylation procedure is then performed and the corresponding 3'-phosphoramidite building blocks 319 are obtained. They are further incorporated into the target oligonucleotides using standard oligonucleotide synthesis.

Example 39. Syntheses of ON 323

Compounds 4, 27-43 are transformed to the corresponding 5'-Hep-Direct alpha-aryl variously substituted (thio- or borano-) phosphate triester (321, Scheme 16), according to the synthetic procedures described by Erion et al. (*J. Am. Chem. Soc.*, 2004, 126, 5154). The standard 3'-deprotection/3'-phosphitylation procedure is then performed and the corresponding 3'-phosphoramidite building blocks 322 are obtained. They are further incorporated into the target oligonucleotides using standard oligonucleotide synthesis.

Example 40. Syntheses of ON 326

Compounds 4, 27-43 are dissolved in dry acetonitrile and tetrazole (2.5 equiv) followed by O-cyanoethyl-O-octadecanyl-di-isopropyl phosphoramidite (1.5 equiv) are added. The reaction mixture is stirred for 2 h under argon at room temperature. Tert-butylhydroperoxide (TBHP, 4 equiv) is then added and the mixture is stirred for 1 more hour. After aqueous work-up and silica gel chromatography, the obtained compound 324 is subjected to the standard 3'-deprotection/3'-phosphitylation procedure affording the corresponding 3'-phosphoramidite building block 325, which is further incorporated into the target oligonucleotides using standard oligonucleotide synthesis.

Example 41a. Syntheses of ON 330

Compounds 4, 27-43 are dissolved in dry acetonitrile and tetrazole (2.5 equiv) followed by the appropriate O-benzyl-O-(1-aryl-4-bromobutyl)-di-isopropyl phosphoramidite (1.5 equiv) are added. The reaction mixture is stirred for 2 h under argon at room temperature. The corresponding 5'-phosphite triester 327 is then heated in THF affording the Arbuzov phosphonate 328. The latter is subjected to the standard 3'-deprotection/3'-phosphitylation procedure affording the corresponding 3'-phosphoramidite building block 329, which is further incorporated into the target oligonucleotides using standard oligonucleotide synthesis.

Example 41b. Syntheses of ON 334

Compounds 4, 27-43 are dissolved in dry acetonitrile and tetrazole (2.5 equiv) followed by the appropriate bis-ethyl-di-isopropyl phosphoramidite (1.5 equiv) are added. The reaction mixture is stirred for 2 h under argon at room temperature. The corresponding 5'-phosphite triester 331 is reacted with the appropriate 0-formyl aldehyde, in an Abramov type reaction, according to the procedure described by Harvey et al. (*J. Org. Chem.*, 1997, 62, 6722). The isolated Abramov adduct 332 is subjected to the standard 3'-deprotection/3'-phosphitylation procedure affording the corresponding 3'-phosphoramidite building block 333, which is further incorporated into the target oligonucleotides using standard oligonucleotide synthesis.

Example 42. Synthesis of Backbone Phosphoramidate Oligonucleotides, Exhibiting the Above-Mentioned 5'-Terminal Modifications Modifications of the phosphate bridge between position 1 and 2 (5' end): The 3'-H-phosphonate monoesters of previously mentioned 5' modified nucleosides is prepared using diphenyl phosphite, followed by aqueous hydrolysis, bicarbonate wash and silica gel chromatography. These compounds are obtained as their triethylammonium salts and are readily used in standard oligonucleotide synthesis, affording the corresponding oligonucleotides, exhibiting an H-phosphonate diester bridge on the appropriate position (Scheme 18).

Modifications of the phosphate bridge between position 20 and 21 (3' end): Commercially available 3'-H-phosphonate monoester building block of the corresponding nucleoside are used in standard oligonucleotide synthesis, affording the corresponding oligonucleotides, exhibiting an H-phosphonate diester bridge on the appropriate position (Scheme 18).

The above described H-phosphonate diester linkages are readily oxidized by anhydrous carbon tetrachloride in dry pyridine in the presence of an appropriate primary amine leading to the corresponding phosphoramidate diester linkage (Scheme 18). As an example, cationic backbone modifications can be introduced (compounds 335 and 347), formed by oxidation in presence of N,N-dimethylaminopropylamine; amphiphilic heteroaromatic modifications (336, 348), formed by oxidation in presence of histamine; anionic modifications (337, 349), formed by oxidation in presence of (poly-)carboxy-alkylamines; or likewise using hydroxyalkylamines (341, 353), alkoxyalkylamines (344, 356), thioloalkylamines (342, 354), variously substituted arylalkylamines (346, 358) and others (Scheme 18).

Example 43. Syntheses of ONs 361 and 364

2'-α-C-fluoro-2'-β-C-methyl uridine and 2'-α-C-fluoro-2'-β-C-methyl cytidine are prepared according to the procedure described by Sofia et al. (WO2008121634A2 20081009). 2'-α-C-fluoro-2'-β-C-methyl uridine is dried by azeotropic distillation with anhydrous pyridine and dissolved in anhydrous pyridine. 1.5 equiv of DMTrCl are added and the mixture is stirred under argon for 2 h. After completion, the reaction mixture is quenched with methanol, diluted with dichloromethane and washed twice with saturated bicarbonate solution. The organics are dried and evaporated to dryness; the crude residue is purified by silica gel chromatography affording pure 359. 2'-α-C-fluoro-2'-β-C-methyl cytidine is dissolved in anhydrous DMF and 1.1 equiv of benzoic anhydride are added and the mixture is stirred overnight under argon. The solvents are evaporated to dryness, the residue is coevaporated three times with anhydrous pyridine, than dissolved in dry pyridine and 1.5 equiv of DMTrCl are added and the mixture is stirred under argon for 2 h. After completion, the reaction mixture is quenched with methanol, diluted with dichloromethane and washed twice with saturated bicarbonate solution. The organics are dried and evaporated to dryness; the crude residue is purified by silica gel chromatography affording pure 362.

The suitably protected nucleosides 359 and 362 are phosphitylated using cyanoethyl-chloro-di-isopropyl-phosphoramidite, affording 3'-phosphoramidite building blocks 360 and 363, which are further incorporated into the target oligonucleotides using standard oligonucleotide synthesis.

Example 44. Syntheses of ON 367

2'-β-C-methyl nucleosides (Couturier et al., *Tetrahedron*, 2007, 46, 11260) are protected on the base moieties according to the general procedures published by Ti, Gaffney and Jones (*J. Am. Chem. Soc.*, 1982, 104, 1316). After introduction of the 5' DMTr group as described for compound 359, 2'-phosphitylation using cyanoethyl-chloro-di-isopropyl-phosphoramidite, afforded the 2'-phosphoramidite building blocks 366, which are further incorporated into the target 2'-5' linked oligonucleotides (367) using standard oligonucleotide synthesis.

Example 45. Syntheses of ONs 370 and 373

2'-α-C-fluoro and 2-β-C-fluoro nucleosides (Woo et al., *Bioorg. Med. Chem. Lett*, 2003, 13, 817) are used for the preparation of the corresponding 2'-phosphoramidite building blocks 369 and 372 according to the procedures described for compound 366 (Scheme 19). 369 and 372 are further incorporated into the target 2'-5' linked oligonucleotides (370 and 373) using standard oligonucleotide synthesis.

Example 46. Syntheses of ONs 374 and 376

2'-β-C-methyl uridine (Pierra et al., *J. Med. Chem.*, 2006, 49, 6614) is dissolved in anhydrous pyridine and reacted with DMTrCl as previously described. After aqueous workup, the crude nucleoside is dried by azeotropic distillation with anhydrous acetonitrile, dissolved in anhydrous DMF and reacted with 2 equiv of NaH and 5 equiv of methyl iodide. After 2 h stirring at room temperature, the reaction mixture is diluted with cold ethyl acetate and quenched with absolute ethanol. It is then washed with a saturated ammonium chloride solution; the organics are dried and evaporated to dryness. The crude nucleoside is purified by silica gel chromatography, affording pure 374.

374 is further phosphitylated using cyanoethyl-chloro-di-isopropyl-phosphoramidite, affording 3'-phosphoramidite building block 375, which is incorporated into the target oligonucleotide 376 using standard oligonucleotide synthesis.

Example 47a. Syntheses of ONs 377 and 379

2'-β-C-methyl cytidine (Pierra et al., *J. Med. Chem.*, 2006, 49, 6614) is dissolved in anhydrous pyridine and reacted with DMTrCl as previously described. After aqueous workup, the crude nucleoside is dried by azeotropic distillation with anhydrous acetonitrile, dissolved in anhydrous DMF and reacted with 2 equiv of NaH and 5 equiv of methoxyethyl chloride. After 2 h stirring at room temperature, the reaction mixture is diluted with cold ethyl acetate and quenched with absolute ethanol. It is then washed with a saturated ammonium chloride solution; the organics are dried and evaporated to dryness. The residue is then dissolved in dry DMF and reacted overnight with 1.1 equiv of benzoic anhydride. The solvents are evaporated to dryness and the crude nucleoside is purified by silica gel chromatography, affording pure 377.

377 is further phosphitylated using cyanoethyl-chloro-di-isopropyl-phosphoramidite, affording 3'-phosphoramidite building block 378, which is incorporated into the target oligonucleotide 379 using standard oligonucleotide synthesis.

Example 47b. Syntheses of ON 388

The 1-alkoxy-eth-1-yl group is a convenient protection for the 2'-hydroxy group of 2'-β-C-methyl nucleosides during oligonucleotide synthesis (Pontiggia et al., *Nucl. Acid Res. Symp. Ser.*, 2008, 52, 521). It is introduced by means of the corresponding alkyl chloride in similar manner as for compound 377. The corresponding 3'-phosphoramidite building block 387 is incorporated into the target oligonucleotide 388 using standard oligonucleotide synthesis.

Example 47c. Syntheses of ONs 382 and 385

2'-O-alkyl phosphoramidite building blocks exhibiting a 2,6-diamino purine moiety (381, 384) are prepared according to the alkylation procedures previously described. These 3'-phosphoramidite building blocks are incorporated into the target oligonucleotides 382 and 385 using standard oligonucleotide synthesis.

Example 48: Synthesis of RNA 5'-boranomethylphosphate A-69860 (Scheme 39)

Step 1: 3'-O-tert-Butyldimethylsilyl-2'-O-methyluridine 5'-boranodimethylphosphate (577-15)

3'-O-tert-Butyldimethylsilyl-2'-O-methyluridine (1.12 g, 3 mmol) and triethylammonium dimethylboranophosphate (2.03 g, 3 equiv; prepared according to the procedure: M. Shimizu et al., *J. Org. Chem.* 2004, 69, 5261-5268) were dried by coevaporation with pyridine and toluene and finally dissolved in THF (30 mL). To this solution were added DIPEA (5.1 mL, 10 equiv), 3-nitro-1,2,4-triazole (1.71 g, 5 equiv) and N,N-bis-(2-oxo-3-oxazolidinyl)phosphonic chloride (3.82 g, 5 equiv). The mixture was stirred at r. t. for 1 h, then diluted with $CH_2Cl_2$ (100 mL) and washed with sat. aq. $NaHCO_3$ (3×100 mL). Aq. washings were back-extracted with $CH_2Cl_2$ (2×100 mL) and combined extracts dried ($Na_2SO_4$). Evaporated residue was purified on silica (80 g) using a gradient of EtOAc (0-50%) in $CH_2Cl_2$ as an eluent to yield the target compound 026-2 (1.23 g, 30%) as a white foam.

Step 2: 2'-O-Methyluridine 5'-boranodimethylphosphate (577-34)

Into an ice-cold solution of boranophosphotriester 026-2 (0.56 g, 0.8 mmol) in THF (12 mL) was added TBAF (2.36 mL, 2 equiv; 1.0 M in THF) and the resulting mixture stirred at 0° C. for 20 min. At this point the reaction was quenched with silica and the mixture evaporated to dryness. Purification on silica (24 g) using a gradient of MeOH (0-5%) in $CH_2Cl_2$ as an eluent afforded the target compound 026-3 (0.38 g, 88%) as a white foam.

Step 3: 2'-O-Methyl-5'-O-(boranodimethylphosphoryl)uridine 3'-[N,N-diisopropyl-(2-cyanoethyl)-phosphoramidite (577-36)

Compound 577-34 (330 mg, 0.9 mmol), rendered anhydrous by evaporation with pyridine and toluene, was dissolved in $CH_2Cl_2$ (10 mL). To this solution were added $Et_3N$ (0.38 mL, 3 equiv) and N,N-diisopropyl chloro(2-cyanoethyl)phosphoramidite (300 □L, 1.5 equiv) and the resulting mixture stirred at r. t. for 1 h. At this point the solution was diluted with $CH_2Cl_2$ (50 mL) and washed with 2% aq. $NaHCO_3$, brine and dried ($Na_2SO_4$). Evaporated residue was purified on silica (12 g) using a gradient of EtOAc (0-50%) in $CH_2Cl_2$ as an eluent to yield the target phosphoramidite 577-36 (280 mg, 55%) as a crisp foam.

$^{31}$P-NMR ($CDCl_3$): δ 150.91, 150.43 (Rp/Sp P-amidite), 119.65 (P—$BH_3$).

Step 4: RNA 5'-boranomethylphosphate A-69860

Phosphoramidite 577-36 (0.2 M in MeCN) was coupled onto 5'-end of A-55311 on CPG using standard automatic synthesis conditions with 5-ethylthio-1H-tetrazole as activator and DDTT/pyridine as oxidizer. RNA on CPG was treated with aq. $NH_3$ at 55° C. for 5 h and finally purified by desalting with RP-HPLC.

ES MS: 7138.1 (found), 7139.95 (calcd)

Example 49: Synthesis of Oligonucleotides A-57009 and A-57010 (Scheme 40)

Step 1:

4'-hydroxymethyl-2'-deoxy-3'-O-tert-butyl-dimethylsilyl Thymidine (499-09) was synthesized according to the method previously described by Jones et al. *J. Org. Chem.*, 1979, 44, 1309. Compound 499-09 was obtained in a 30% yield starting from commercially available 2'-deoxy Thymidine. Compound 499-09 (1.1 mmol) was co-evaporated with anhydrous acetonitrile two times, then dissolved in acetonitrile (33 mL), 13 mL of 0.45 M 1-H tetrazole solution (5.5 mmol) was added, followed by 1.7 mmol of cyanoethyl-tetra-isopropyl-phosphorodiamidite. The reaction mixture was stirred under argon for 30 min. Water was then added to the mixture (0.1 mL), stirred for 10 minutes, then 5.5 M solution of tert-butyl hydroperoxide (2.5 mL, 11 mmol) was added and the mixture stirred for 1 hour. The reaction mixture was diluted with dichloromethane and washed twice with brine. The organics were dried with sodium sulfate, filtered and evaporated to dryness. The crude product was purified by silica gel flash chromatography providing pure 499-37 (521 mg, 94%).

$^{31}$P NMR δ: ($CDCl_3$, −7.8; −8.9 ppm); MS: 502 $(M+H)^+$.

Step 2:

Compound 499-37 (1.53 mmol) was dissolved in 16 mL of anhydrous THF and 1.3 mL of 18.5 M triethylamine trihydrofluoride (23 mmol) were added and the mixture was stirred overnight. Silica gel was poured in the reaction flask then packed into a sample cartridge and eluted using flash chromatography with dichloromethane and 5% methanol. Pure 499-48 was recovered in 50% yield.

$^{31}$P NMR δ: (DMSO-$d^6$, −9.2 ppm); MS: 388 $(M+H)^+$.

Step 3:

499-48 was 3'-phosphitylated using the following protocol: starting nucleoside (0.25 mmol) was co-evaporated three times with anhydrous acetonitrile, then dissolved in 6.5 mL of dry acetonitrile. 90 mg of di-isopropylammonium tetrazolide (0.5 mmol) were added, followed by a first addition of 0.38 mmol of cyanoethyl-tetra-isopropyl-phosphorodiamidite. The reaction mixture was stirred for 1.5 hours, and then a second addition of cyanoethyl-tetra-isopropyl-phosphorodiamidite (0.38 mmol) was made. The mixture was stirred for additional 1.5 hours. The reaction mixture was diluted with neutralized ethyl acetate containing 1% pyridine and washed twice with brine. The aqueous layers were back-extracted with ethyl acetate, dried with sodium sulfate, filtered and evaporated to dryness. The crude product was purified by silica gel flash chromatography providing pure 499-77 (90 mg, 60%).

$^{31}$P NMR δ: ($CD_3CN$, 155.7; 154.8; −3.9; −4.0 ppm).

Step 4:

Oligonucleotide synthesis providing A-57009 and A-57010 was manually performed as follows: 1 μmol of oligonucleotide 55311 (Scheme 1) bound on CPG was introduced into a dry Twist® synthesis column from Glen Research. Phosphoramidite 499-77 (50 μmol) was dissolved in 0.3 mL of anhydrous acetonitrile and pushed through the synthesis column using a 1 mL plastic syringe attached to the bottom end of the column. A second 1 mL plastic syringe containing 0.5 mL of 0.25 M benzylthiotetrazole solution was attached to the bottom end of the synthesis column, and then the two solutions were pushed through the column and gently mixed. The mixture was kept in contact with the CPG bound oligonucleotide for 30 min. The column was emptied, the support washed with anhydrous acetonitrile and dried. The dried support was then divided in two batches: the first batch was treated with oxidizing iodine solution (Glen) the second one with home-made DDTT solution saturated in pyridine. Each batch was treated with aqueous ammonia for 6 hours at 55° C. After filtration and lyophilization, the target oligonucleotides were obtained.

A-57009: MS: Calculated 7108.03/Found 7105.76.

A-57010: MS: Calculated 7124.10/Found 7121.98.

Example 50. Synthesis of Oligonucleotides A-57007 and A-57008 (Scheme 41)

The reaction sequence leading to oligonucleotides A-57007 and A-57008 was similar to the one employed for the synthesis of A-57009 and A-57010.

Step 1:

4'-hydroxymethyl-2'-O-methyl-3'-O-tert-butyl-dimethyl-silyl Uridine (499-106) was obtained in a 30% yield starting from commercially available 2'-O-methyl Uridine according the previously published procedure. The cyclic phosphate 499-124 was then prepared using the phosphitylation/oxidation sequence used for the preparation of 499-37, and 499-124 was prepared in 67% yield.

$^{31}$P NMR δ: (CDCl$_3$, −7.3; −9.3 ppm), MS: 518 (M+H)$^+$.

Step 2:

The 3'-O-TBS group was then deprotected using identical procedure as the one used for the preparation of 499-48, affording the corresponding analog 499-132 in 40% yield.

$^{31}$P NMR δ: (CD$_3$CN, −4.5 ppm); MS: 404 (M+H)$^+$.

Step 3:

499-132 was phosphitylated on the 3'-position using the phosphitylation protocol described for the synthesis of phosphoramidite 499-77. The 3'-phosphoramidite 499-154 was prepared in 54% yield.

$^{31}$P NMR δ: (CD$_3$CN, 156.5; 155.8; −4.2; −4.4 ppm).

Step 4:

Oligonucleotide synthesis providing A-57007 and A-57008 was manually performed as previously described for oligonucleotides A-57009 and A-57010. Phosphoramidite 499-154 (50 μmol) was dissolved in 0.3 mL of anhydrous acetonitrile and pushed through the synthesis column using a 1 mL plastic syringe attached to the bottom end of the column. A second 1 mL plastic syringe containing 0.5 mL of 0.25 M benzylthiotetrazole solution was attached to the bottom end of the synthesis column, and then the two solutions were pushed through the column and gently mixed. The mixture was kept in contact with the CPG bound oligonucleotide for 30 min. The column was emptied, the support washed with anhydrous acetonitrile and dried. The dried support was then divided in two batches: the first batch was treated with oxidizing iodine solution (Glen) the second one with home-made DDTT solution saturated in pyridine. Each batch was treated with aqueous ammonia for 6 hours at 55° C. After filtration and lyophilization, the target oligonucleotides were obtained.

A-57007: MS: Calculated 7124.03/Found 7121.67.

A-57008: MS: Calculated 7140.10/Found 7137.72.

Example 51. Synthesis of Nucleoside 499-198 (Scheme 42)

Step 1:

5"-mono-O-DMTr nucleoside 499-158 was prepared from diol 499-09 according to the procedures published by Yang et al. *Tetrahedron Lett.*, 1992, 33, 41 and *Tetrahedron Lett.*, 1992, 33, 37. 499-158 was obtained in 65% yield. 499-158 (0.3 mmol) was dissolved in anhydrous acetonitrile (9 mL) and phosphitylated on the 5'-position using di-cyanoethyl-di-isopropyl phosphoramidite (0.45 mmol) and 1-H tetrazole solution (0.9 mmol). The mixture was stirred under argon at room temperature for 1.5 hours. Water was added, the solution was stirred for 10 additional minutes, and then TBHP solution (0.7 mL, 3 mmol) was added. The mixture was stirred for 30 min until oxidation was completed. The reaction mixture was diluted with dichloromethane and washed twice with brine. The organics were dried with sodium sulfate, filtered and evaporated to dryness. The crude product was purified by silica gel flash chromatography providing pure 499-181 (270 mg, 90%).

$^{31}$P NMR δ: (CDCl$_3$, 2.3 ppm).

Step 2:

Compound 499-181 (0.25 mmol) was dissolved in 2.5 mL of anhydrous THF and 0.3 mL of 18.5 M triethylamine trihydrofluoride (5 mmol) were added and the mixture was stirred overnight. Silica gel was poured in the reaction flask then packed into a sample cartridge and eluted using flash chromatography with dichloromethane and 5% methanol. Pure 499-198 was recovered in a 58% yield.

$^{31}$P NMR δ: (CD$_3$CN, 3.0 ppm).

Example 52. Synthesis of oligonucleotide A-66336 (Scheme 43)

Step 1:

5"-mono-O-DMTr nucleoside 499-205 was prepared from diol 499-106 in a 68% yield as previously discussed. 0.8 mmol of 499-205 were then dissolved in 16 mL of anhydrous THF and 1.6 mL (1.6 mmol) of 1 M TBAF solution in THF were added. The mixture was stirred at room temperature for 20 hours until deprotection of the TBS group was complete. The solvents were then evaporated to dryness; the residue was dissolved in dichloromethane and purified by silica gel flash chromatography, affording pure 559-24 in a 99% yield.

MS: 591 (M+H)$^+$; 303 (DMTr)$^+$.

Step 2:

Nucleoside 559-24 (0.6 mmol) was selectively phosphitylated on the primary 5'-OH position using a protocol described by Zlatev et al. *Tetrahedron Lett.*, 2006, 47, 8379. 1.8 g (6 mmol) of poly-vinyl-pyridinium tosylate and a three-step addition of di-cyanoethyl phosphoramidite (0.3+ 0.15+0.15 mmol) were used. The selectivity of the reaction was monitored by RP-HPLC and 76% selectivity with 99% conversion of starting material was achieved. Following completion of the phosphitylation reaction, water was added, the mixture was shaken for 5 min, and then the PVP-tosylate resin was filtered off and well rinsed with dichloromethane. The filtrates were concentrated to half volume, and 1 mL of TBHP was added and the solution stirred for 30 min. The solvents were evaporated to dryness; the residue was dissolved in dichloromethane and washed twice with brine. The organics were dried with sodium sulfate, filtered and evaporated to dryness. The crude product was purified by silica gel flash chromatography providing pure 559-23 (260 mg, 56%).

$^{31}$P NMR δ: (CD$_3$CN, 3.1 ppm).

Step 3:

559-23 was phosphitylated on the 3'-position using the phosphitylation protocol described previously. The 3'-phosphoramidite 559-144 was prepared in 44% yield and lyophilized from dioxane for long term storage.

$^{31}$P NMR δ: (CD$_3$CN, 155.8; 155.3; 3.1; 3.0 ppm).

Step 4:

Phosphoramidite 559-144 (50 μmol) was dissolved in 0.3 mL of anhydrous acetonitrile and pushed through the synthesis column using a 1 mL plastic syringe attached to the bottom end of the column containing CPG bound 55311 oligonucleotide. A second 1 mL plastic syringe containing 0.5 mL of 0.25 M benzylthiotetrazole solution was attached to the bottom end of the synthesis column, and then the two solutions were pushed through the column and gently mixed. The mixture was kept in contact with the CPG bound oligonucleotide for 30 min. The column was emptied, the support washed with anhydrous acetonitrile and dried. The dried support was treated with home-made DDTT solution saturated in pyridine. The solid support was then treated with aqueous ammonia for 6 hours at 55° C. After filtration and lyophilization, the residue was dissolved in 20% AcOH (2 mL) and shaken for 30 min. The mixture was extracted five times with diethyl ether, and then desalted on a NAP-25 column (Pharmacia). After lyophilization the target oligonucleotide A-66336 was obtained.

MS: Calculated 7158.85/Found 7156.06.

Example 53. Synthesis of 5'-3' Cyclic Phosphate 499-194 (Scheme 44)

Step 1:

5"-mono-O-DMTr nucleoside 499-158 (0.23 mmol) was dissolved in anhydrous THF (2.2 mL), anhydrous triethylamine 0.03 mL was added, followed by 0.3 mL (5 mmol) of 18.5 M triethylamine trihydrofluoride. The reaction mixture was stirred at room temperature for 24 hours. Silica gel was poured in the reaction flask then packed into a sample cartridge and eluted using flash chromatography with dichloromethane and 5% methanol. Pure 499-158 was recovered in 70% yield.

MS: 574 (M+H)$^+$, 303 (DMTr)$^+$.

Step 2:

The 5'-3' cyclic phosphate 499-185 was obtained using the procedure described previously for the syntheses of 499-37 and 499-124. After aqueous work-up and flash chromatography purification, 499-185 was obtained in a 45% yield.

$^{31}$P NMR δ: (CD$_3$CN, −0.1; −2.5 ppm).

Step 3:

499-185 (0.1 mmol) was dissolved in 1 mL of dichloromethane/methanol 7:3 (v/v) mixture and the mixture was cooled at −20° C. 50 mg of benzene-sulfonic acid (0.3 mmol), dissolved in 0.5 mL of the dichloromethane/methanol mixture were added dropwise to the reaction flask. The mixture was stirred for 1.5 hours. Pyridine was added at the end of reaction until the orange color has disappeared. Then silica was poured to the reaction flask and all solvents were evaporated to dryness. The dry silica was packed into a sample cartridge and eluted using flash chromatography with dichloromethane and 5% methanol. Pure 499-194 was recovered in 50% yield.

$^{31}$P NMR δ: (CD$_3$CN, 0.8; −2.0 ppm).

Example 54. Synthesis of 5'-5'' cyclic thio-phosphate 499-200 (Scheme 45)

Step 1:

Diol 499-106 (0.1 mmol) was dissolved in 3 mL of anhydrous acetonitrile, 0.5 mmol of tetrazole solution were added, followed by 0.15 mmol of di-cyanoethyl phosphoramidite. After stirring the mixture for 1 hour at room temperature, 2 mL of saturated DDTT solution in pyridine is added and the mixture stirred for one additional hour. Solvents were evaporated to dryness; the residue was dissolved in dichloromethane and washed twice with brine. The organics were dried with sodium sulfate, filtered and evaporated to dryness. The crude product was purified by silica gel flash chromatography providing pure 499-187 (60 mg, 90%).

$^{31}$P NMR δ: (CD$_3$CN, 62.1; 59.6 ppm).

Step 2:

The 3'-TBS group in the cyclic thio-phosphate 499-187 was deprotected as previously described for 499-124. 499-200 was obtained in 35% yield after flash chromatography purification.

$^{31}$P NMR δ: (CD$_3$CN, 64.7 ppm).

Example 55. Synthesis of Oligonucleotide A-66337 (Scheme 46)

Step 1:

Diol 499-106 (0.32 mmol) was co-evaporated three times with anhydrous pyridine, dissolved in 3.5 mL of dry pyridine, and then 0.95 mmol of DMTr-Cl were added and the mixture was stirred at room temperature for 24 hours. After completion of the reaction, the mixture was diluted with dichloromethane, washed twice with saturated sodium bicarbonate, and the aqueous layers were back-extracted with dichloromethane. The organics were dried with sodium sulfate, filtered and evaporated to dryness. The crude product was purified by silica gel flash chromatography providing pure 559-12 (300 mg, 93%).

Step 2:

The bis-DMTr nucleoside 559-12 (0.22 mmol) was dissolved in anhydrous THF (4.5 mL) and 0.33 mmol of 1 M TBAF solution (0.33 mL) were added to the mixture and the solution was stirred overnight at room temperature. The solvents were removed under reduced pressure, the residue was dissolved in dichloromethane and was purified by silica gel flash chromatography providing pure 559-14 (140 mg, 70%).

Step 3:

Nucleoside 559-14 was phosphotylated on its 3'-position using the standard phosphitylation method described for 559-23. 3'-Phosphoramidite 559-42 was obtained in 75% yield (820 mg).

$^{31}$P NMR δ: (CD$_3$CN, 64.7 ppm).

Step 4:

Phosphoramidite 559-42 (50 μmol) was dissolved in 0.3 mL of anhydrous acetonitrile and pushed through the synthesis column using a 1 mL plastic syringe attached to the bottom end of the column containing CPG bound 55311 oligonucleotide. A second 1 mL plastic syringe containing 0.5 mL of 0.25 M benzylthiotetrazole solution was attached to the bottom end of the synthesis column, and then the two solutions were pushed through the column and gently mixed. The mixture was kept in contact with the CPG bound oligonucleotide for 30 min. The column was emptied, the support washed with anhydrous acetonitrile and dried. The dried support was treated with home-made DDTT solution saturated in pyridine. The column containing the solid support was then washed by 5% dichloroacetic acid in dichloromethane and after washing the solid support was rinsed with dry acetonitrile and dried. A 0.3 M solution of di-cyanoethylphosphoramidite in acetonitrile was premixed with benzylthiotetrazole and then left to react with the solid support for 1 hour. After rinsing the support with acetonitrile, oxidizing iodine solution was applied for 30 min. After washing, the solid support was treated with aqueous ammonia for 6 hours at 55° C. After filtration and lyophilization, the target oligonucleotide A-66337 was obtained.

MS: Calculated 7238.82/Found 7236.44.

Example 56. Synthesis of Phosphoramidite 559-53 (Scheme 47)

Step 1:

Diol 499-106 (0.55 mmol) was co-evaporated three times with anhydrous acetonitrile, and then dissolved in 5 mL of dry acetonitrile. 6.6 mL (3 mmol) of tetrazole solution were added, followed by the addition of 1.5 mmol of di-cyanoethyl phosphoramidite. The solution was stirred for 40 min and after completion of the reaction, water was added and the solution was stirred for additional 5 minutes. 2 mL of 5.5 M TBHP (10 mmol) were finally added and the reaction mixture was stirred for 1 hour. The solvents were evaporated to dryness; the residue was dissolved in dichloromethane and washed twice with brine. The organics were dried with sodium sulfate, filtered and evaporated to dryness. The crude product was purified by silica gel flash chromatography providing pure 499-203 (348 mg, 89%).

$^{31}$P NMR δ: (CD$_3$CN, 3.64; 3.06 ppm).

Step 2:

The 3'-TBS group in 499-203 was removed using NEt$_3$-3HF as previously described. The corresponding nucleoside 559-03 was obtained in 50% yield.

$^{31}$P NMR δ: (CD$_3$CN, 3.3; 3.1 ppm).

MS: 683 (M+Na)$^+$.

Step 3:

Phosphoramidite 559-53 was prepared according to the phosphitylation procedure used for the preparation of 559-144. 559-53 was obtained in 40% yield.

$^{31}$P NMR δ: (CD$_3$CN, 159.8; 3.1; 2.9 ppm).

Example 57. Synthesis of 4'-Phtalimidomethyl Nucleoside 626-01 (Scheme 48)

Step 1.

Diol 499-106 (0.25 mmol) was dissolved in 5 mL of anhydrous THF and 0.5 mL (0.5 mmol) of 1 M TBAF solution were added. The mixture was stirred at room temperature overnight. The solvents were evaporated to dryness; the residue was dissolved in dichloromethane and purified using silica gel flash chromatography affording pure 559-64 (quantitative yield).

Step 2.

Triol 559-64 was selectively benzoylated on its 4'-hydroxymethyl position according to the procedure described by Wang et al., Tetrahedron Lett., 1996, 37, 6515. The corresponding mono benzoyl compound 559-72 was obtained in 65% yield.

MS: 393 (M+H)$^+$.

Step 3.

Compound 559-72 (1 mmol) was co-evaporated twice with anhydrous pyridine, and then dissolved in dry pyridine (15 mL). 510 mg (1.5 mmol) of DMTr-Cl were added to the mixture and the resulting solution was stirred overnight at room temperature. After completion, the reaction mixture was concentrated to half volume, diluted with dichloromethane and washed twice with saturated bicarbonate solution. The aqueous layers were back-extracted with dichloromethane. The organics were dried with sodium sulfate, filtered and evaporated to dryness. The crude product was purified by silica gel flash chromatography providing pure 559-199 (650 mg, 94%).

Step 4.

Compound 559-199 (0.9 mmol) was dissolved in 3 mL of THF/EtOH mixture and 5 mL of 30% ammonia was added. The flask was hermetically sealed and the mixture was stirred at 40° C. overnight. The solvents were evaporated to dryness; the residue was co-evaporated twice with acetonitrile then purified by flash chromatography. Pure 559-201 was obtained in 99% yield.

Step 5.

Nucleoside 559-201 (0.9 mmol) was involved in a Mitsonobu reaction for phtalimide coupling according to the procedure described by Heidler et al., Bioorg. Med. Chem., 2009, 17, 1428. The 4'-phtalimidomethyl nucleoside 626-01 was obtained with 20% yield.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

We claim:

1. A nucleoside represented by formula (IV):

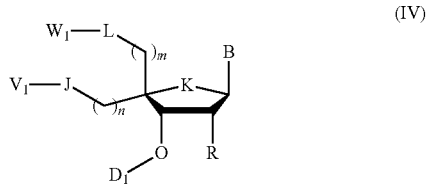

or isomers thereof, wherein:
D$_1$ is H, a hydroxyl protecting group, a solid support, or a reactive phosphorus group;
K is O, S, NR', or optionally substituted alkyl;
B is selected from the group consisting of hydrogen, unsubstituted or substituted aliphatic, a natural nucleobase, a modified nucleobase, and a universal nucleobase;
R is H, OH, SH, halogen, optionally substituted alkyl, optionally substituted alkenyl, optionally substituted alkynyl, optionally substituted alkoxy, optionally substituted alkylthio, optionally substituted alkylamino, or optionally substituted dialkylamino;
L and J are independently absent or selected from the group consisting of S, O, NR', alkylene, alkenylene, and alkynylene;
R' is hydrogen, acyl, aliphatic or substituted aliphatic; and
W$_1$ and V$_1$ are each independently selected from the group consisting of a boronic group B(OH)$_2$, and

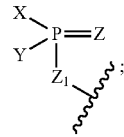

or alternatively, $W_1$ and $V_1$, taken together with the atoms to which they are bonded, form a phosphorous-atom-containing heterocyclic ring;

Z is O, S or NR';

$Z_1$ is O or S,

X and Y are each independently selected from the group consisting of H, O⁻, OH, SH, SM, OM, borane (BH₃), optionally substituted alkyl, optionally substituted alkoxy, optionally substituted alkylthio, optionally substituted alkylamino, and optionally substituted dialkylamino; or X and Y, taken together with the atoms to which they are bonded, form

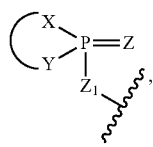

wherein

is an optionally substituted $C_2$-$C_8$ alkylene;

M is a metal counter ion with an overall charge of +1; and m and n are independently 1-10.

2. The nucleoside of claim 1, wherein $V_1$ and $W_1$ are taken together with the atom to which they are bonded to form a nucleoside represented by formula (V):

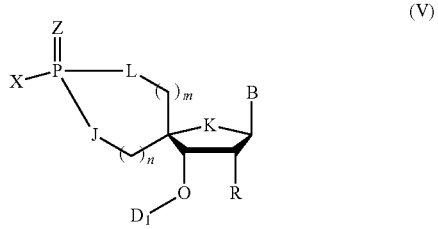

or isomers thereof, wherein:

$D_1$ is H, a hydroxyl protecting group, a solid support, or a reactive phosphorus group;

K is O, S, NR', or an optionally substituted alkyl;

B is selected from the group consisting of hydrogen, unsubstituted or substituted aliphatic, a natural nucleobase, a modified nucleobase, and a universal nucleobase;

X is H, OH, OM, SH, SM, optionally substituted alkyl, optionally substituted alkoxy, optionally substituted alkylthio, optionally substituted alkylamino, or optionally substituted dialkylamino, where M is a metal counter ion;

Z is O, S, or NR';

R is H, OH, SH, halogen, optionally substituted alkyl, optionally substituted alkenyl, optionally substituted alkynyl, optionally substituted alkoxy, optionally substituted alkylthio, optionally substituted alkylamino, or optionally substituted dialkylamino;

R' is hydrogen, acyl, or unsubstituted or substituted aliphatic;

L and J are each independently absent or selected from the group consisting of S, O, NR', alkylene, alkenylene, and alkynylene; and m and n are each independently 1-10.

3. An oligonucleotide comprising a nucleoside represented by formula (IVa):

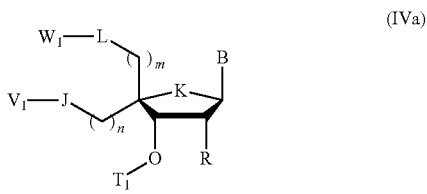

or isomers thereof, wherein:

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino, or an internucleoside linking group attaching the nucleoside to the oligonucleotide;

$T_1$ is hydroxyl, a protected hydroxyl, a linked conjugate group or an internucleoside linking group attaching the nucleoside to the oligonucleotide, wherein at least one of $T_1$ and R is an internucleoside linking group attaching the nucleoside to the oligonucleotide;

K is independently for each occurrence O, S, NR', or optionally substituted alkyl;

each B is selected from the group consisting of hydrogen, unsubstituted or substituted aliphatic, a natural nucleobase, a modified nucleobase, and a universal nucleobase;

L and J are each independently absent or selected from the group consisting of S, O, NR', alkylene, alkenylene, and alkynylene;

$W_1$ and $V_1$ are independently selected from the group consisting of a boronic group (B(OH)₂), and

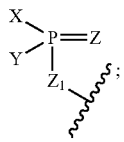

or alternatively, $W_1$ and $V_1$, taken together with the atoms to which they are bonded, form a phosphorous-atom-containing heterocyclic ring;

Z is O, S, or NR';

$Z_1$ is O or S;

R' is hydrogen, acyl, or unsubstituted or substituted aliphatic;

X and Y are each independently selected from the group consisting of H, O⁻, OH, SH, SM, OM, borane (BH₃), optionally substituted alkyl, optionally substituted alkoxy, optionally substituted alkylthip, optionally substituted alkylamino, and optionally substituted dialkylamino; or X and Y, taken together with the atoms to which they are bonded, form

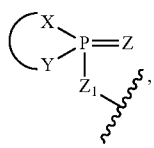

where

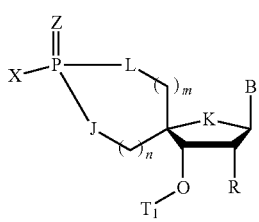

is an optionally substituted $C_2$-$C_8$ alkylene;

M is a metal counter ion; and m and n are each independently 1-10.

4. The oligonucleotide of claim 3, wherein the nucleoside is represented by formula (Va):

(Va)

or isomers thereof, wherein:

R is H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino, or an internucleoside linking group attaching the nucleoside to the oligonucleotide;

$T_1$ is hydroxyl, a protected hydroxyl, a linked conjugate group or an internucleoside linking group attaching the nucleoside to the oligonucleotide, wherein at least one of Ti and R is an internucleoside linking group attaching the nucleoside to the oligonucleotide;

K is independently for each occurrence O, S, NR', or optionally substituted alkyl;

each B is selected from the group consisting of hydrogen, unsubstituted or substituted aliphatic, a natural nucleobase, a modified nucleobase, and a universal nucleobase;

X is H, OH, OM, SH, SM, optionally substituted alkyl, optionally substituted alkoxy, optionally substituted alkylthio, optionally substituted alkylamino, or optionally substituted dialkylamino, where M is a metal counter ion;

Z is O, S, or NR';

R' is hydrogen, acyl, or unsubstituted or substituted aliphatic;

L and J are each independently absent or selected from the group consisting of S, O, NR', alkylene, alkenylene, and alkynylene; and m and n are each independently 1-10.

5. The oligonucleotide of claim 3, wherein said oligonucleotide comprises at least one non-phosphodiester backbone linkage.

6. The oligonucleotide of claim 5, wherein the non-phosphodiester of at least one of said non-phosphodiester backbone linkages is selected from a group consisting of phosphorothioate, phosphorodithioate, alkyl-phosphonate, and phosphoramidate.

7. The oligonucleotide of claim 5, wherein at least one of the non-phosphodiester backbone linkages is placed between the first two nucleosides at the 5'-end and/or between the first two nucleosides at the 3'-end.

8. The oligonucleotide of claim 3, wherein said oligonucleotide comprises at least one ligand conjugate.

9. The oligonucleotide of claim 3, wherein said oligonucleotide is a double-stranded oligonucleotide comprising a first strand and a second strand.

10. The oligonucleotide of claim 9, wherein the nucleoside is present either in the first strand or the second strand of the oligonucleotide.

11. The oligonucleotide of claim 10, wherein said first strand is the sense strand.

12. The oligonucleotide of claim 10, wherein said second strand is the antisense strand.

13. The oligonucleotide of claim 9, wherein the nucleoside is present in both strands of the oligonucleotide.

14. The oligonucleotide of claim 3, wherein said oligonucleotide has a hairpin structure.

15. The oligonucleotide of claim 3, wherein said oligonucleotide is an antisense or a siRNA.

16. The oligonucleotide of claim 15, wherein said oligonucleotide is a single-stranded siRNA.

17. A pharmaceutical composition, comprising the oligonucleotide of claim 3 and a pharmaceutically acceptable excipient.

* * * * *

UNITED STATES PATENT AND TRADEMARK OFFICE
CERTIFICATE OF CORRECTION

| | |
|---|---|
| PATENT NO. | : 10,131,908 B2 |
| APPLICATION NO. | : 14/551714 |
| DATED | : November 20, 2018 |
| INVENTOR(S) | : Muthiah Manoharan et al. |

It is certified that error appears in the above-identified patent and that said Letters Patent is hereby corrected as shown below:

In the Claims

In Claim 4, Column 195, in Line 42, delete "$T_i$" and insert in its place --$T_1$--.

Signed and Sealed this
Twenty-third Day of April, 2024

*Katherine Kelly Vidal*
Katherine Kelly Vidal
*Director of the United States Patent and Trademark Office*